(12) United States Patent
Wu et al.

(10) Patent No.: US 12,097,086 B2
(45) Date of Patent: Sep. 24, 2024

(54) PALATAL EXPANDERS AND METHODS OF DESIGNING PALATAL EXPANDERS

(71) Applicant: Align Technology, Inc., San Jose, CA (US)

(72) Inventors: Fuming Wu, Pleasanton, CA (US); Ryan Kimura, San Jose, CA (US); Jeremy Riley, Mountain View, CA (US); Yaser Shanjani, Milpitas, CA (US); Norman Su, San Jose, CA (US); Jun Sato, San Jose, CA (US); Bastien Pesenti, San Jose, CA (US); John Y. Morton, Palo Alto, CA (US); Jihua Cheng, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 18/346,176

(22) Filed: Jun. 30, 2023

(65) Prior Publication Data

US 2023/0404714 A1    Dec. 21, 2023

Related U.S. Application Data

(60) Continuation of application No. 18/158,451, filed on Jan. 23, 2023, which is a continuation of application
(Continued)

(51) Int. Cl.
*A61C 7/10* (2006.01)
*A61C 7/00* (2006.01)
*A61C 9/00* (2006.01)
*A61C 13/00* (2006.01)
*G16H 40/63* (2018.01)
*G16H 40/67* (2018.01)
(Continued)

(52) U.S. Cl.
CPC .............. *A61C 7/10* (2013.01); *A61C 7/002* (2013.01); *A61C 9/004* (2013.01); *A61C 13/0004* (2013.01); *G16H 40/63* (2018.01); *G16H 40/67* (2018.01); *G16H 50/50* (2018.01); *G06T 17/00* (2013.01)

(58) Field of Classification Search
CPC .. A61C 7/00; A61C 7/002; A61C 7/08; A61C 7/10; A61C 7/36
See application file for complete search history.

(56) References Cited

U.S. PATENT DOCUMENTS 3,792,529 A * 2/1974 Goshgarian .............. A61C 7/20
433/7
4,793,803 A * 12/1988 Martz ...................... A61C 7/08
433/6
(Continued)

FOREIGN PATENT DOCUMENTS

EP           1987799      *  6/2008
WO       2017105117 A2     6/2017

*Primary Examiner* — Edward Moran
*Assistant Examiner* — Matthew P Saunders
(74) *Attorney, Agent, or Firm* — Shay Glenn LLP

(57) ABSTRACT

A series of palatal expanders and methods of designing palatal expanders, including rapid palatal expanders, where outer occlusal surfaces of a palatal expander are shaped to conform to a geometry of corresponding teeth surfaces of the patient's lower jaw to provide occlusion between occlusal surfaces and the corresponding teeth surfaces.

15 Claims, 29 Drawing Sheets

Related U.S. Application Data

No. 17/100,784, filed on Nov. 20, 2020, now Pat. No. 11,576,754, which is a division of application No. 15/831,262, filed on Dec. 4, 2017, now Pat. No. 10,993,783.

(60) Provisional application No. 62/429,696, filed on Dec. 2, 2016.

(51) Int. Cl.
*G16H 50/50* (2018.01)
*G06T 17/00* (2006.01)

(56) References Cited

U.S. PATENT DOCUMENTS

| | | | | |
|---|---|---|---|---|
| 4,919,612 A * | 4/1990 | Bergersen | | A61C 7/08 433/24 |
| 5,167,499 A * | 12/1992 | Arndt | | A61C 7/00 433/7 |
| 5,242,304 A * | 9/1993 | Truax | | A61C 13/225 433/7 |
| 5,312,247 A * | 5/1994 | Sachdeva | | A61C 7/10 433/7 |
| 6,257,239 B1 * | 7/2001 | Kittelsen | | A63B 71/085 128/859 |
| 6,491,519 B1 * | 12/2002 | Clark | | A61C 7/282 433/18 |
| 2002/0192617 A1 * | 12/2002 | Phan | | A61C 19/003 433/18 |
| 2004/0013993 A1 * | 1/2004 | Ito | | A61C 7/00 433/18 |
| 2007/0178421 A1 * | 8/2007 | McSurdy, Jr. | | A61C 7/10 433/7 |
| 2014/0326253 A1 * | 11/2014 | Baratier | | A61F 5/566 382/128 |
| 2015/0079531 A1 * | 3/2015 | Heine | | A61C 7/08 433/19 |
| 2015/0238280 A1 * | 8/2015 | Wu | | A61C 7/36 433/24 |

\* cited by examiner

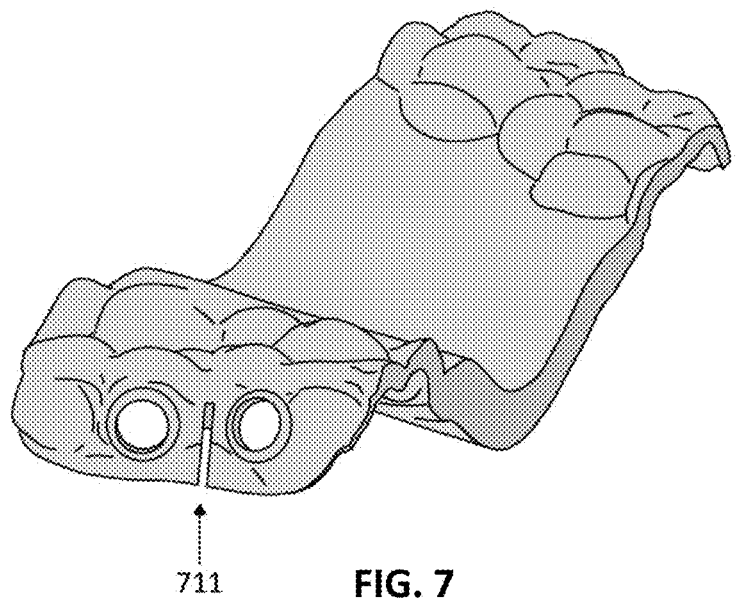
FIG. 7
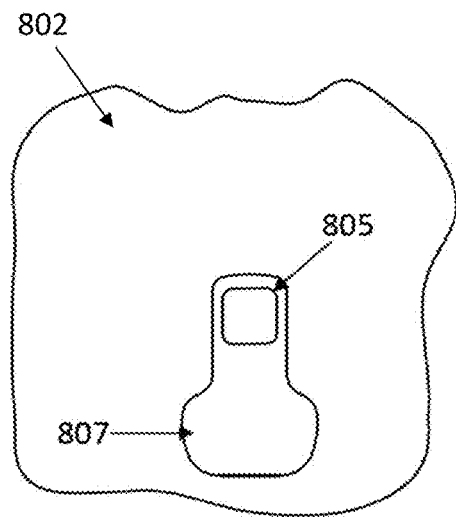
FIG. 8A
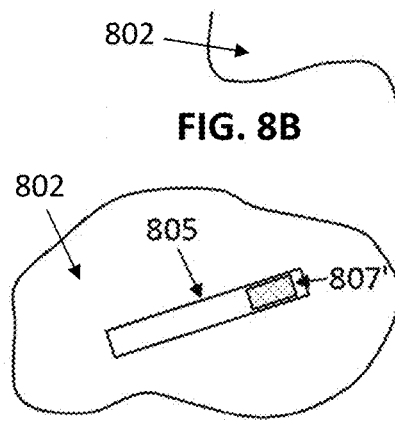
FIG. 8B
FIG. 8C
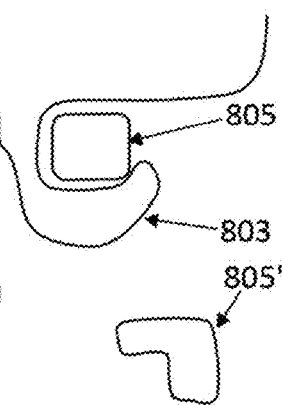
FIG. 8D
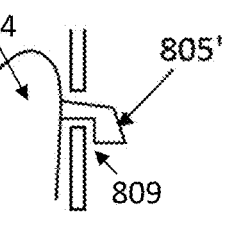
FIG. 8E
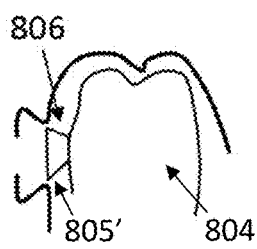
FIG. 8F
FIG. 8G
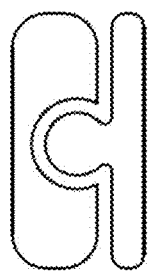
FIG. 8H Tipping of teeth

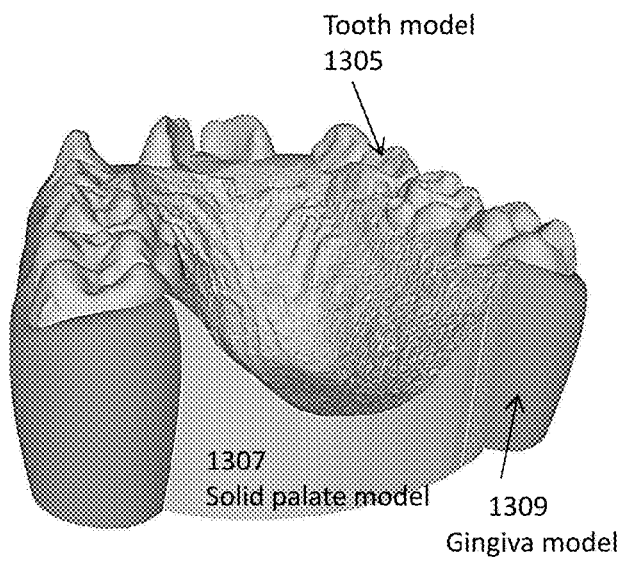
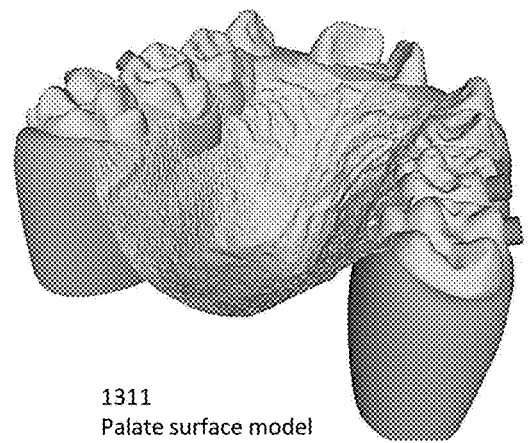
FIG. 13C      FIG. 13D
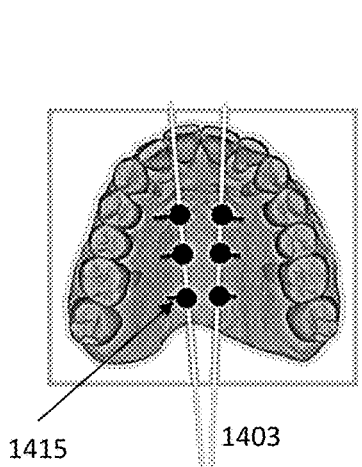
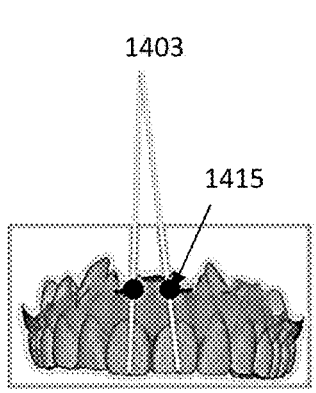
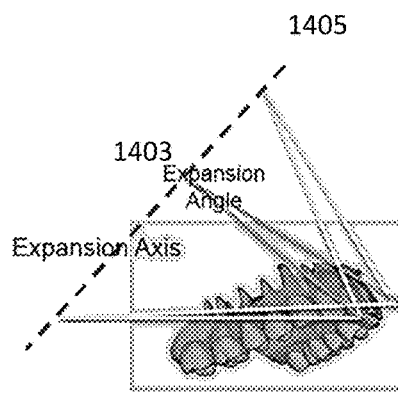
Palatal Expansion: The movement of central control points based on rotation angle
Palatal Expansion: The movement of central control points based on rotation angle
Expansion axis and angle
FIG. 14A      FIG. 14B      FIG. 14C

Expansion angle

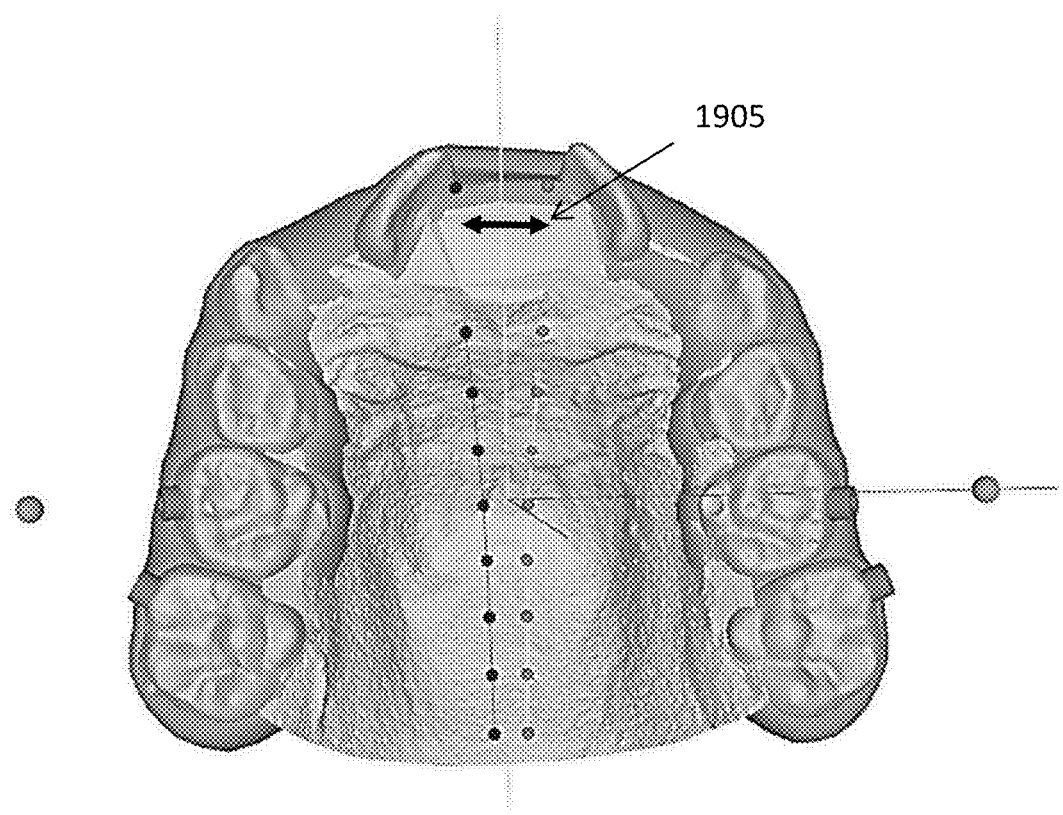
FIG. 19B
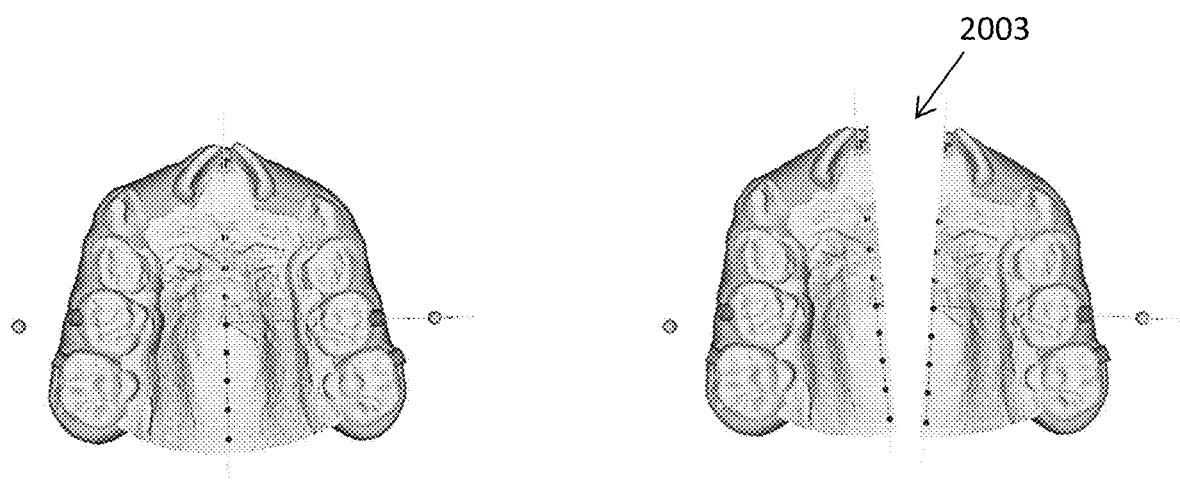
FIG. 20A        FIG. 20B

FIG. 21A
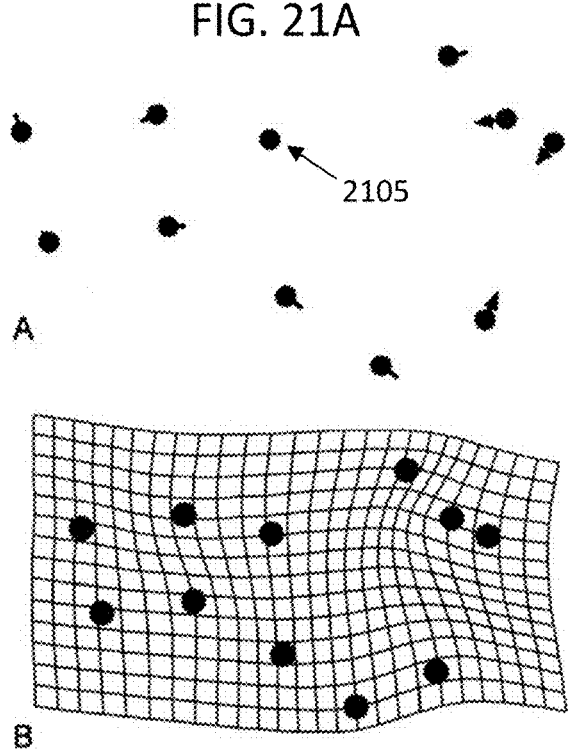
2105
FIG. 21B
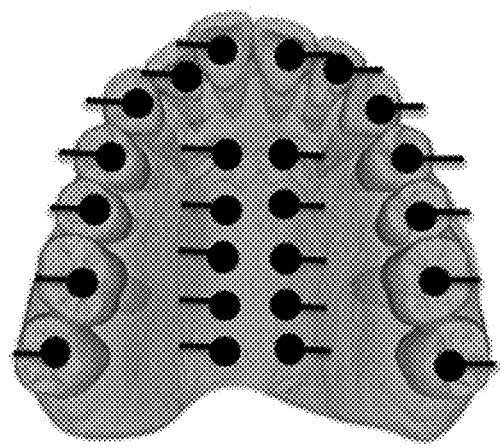
FIG. 21C
Control Points for
Palatal Expansion
Add control points near
central plane
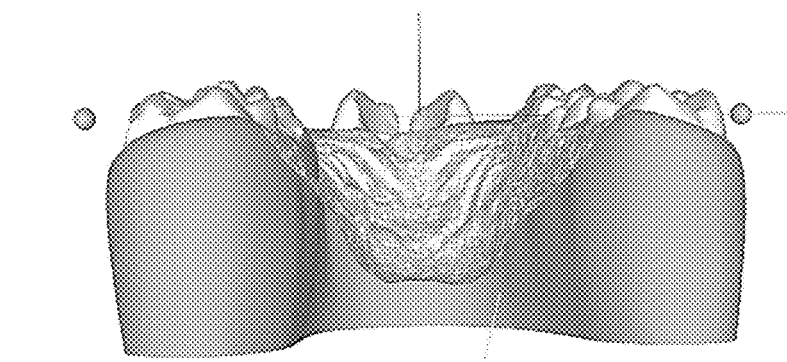
FIG. 22A
2201
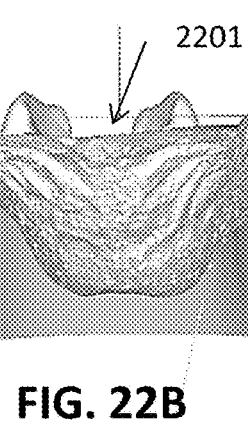
FIG. 22B

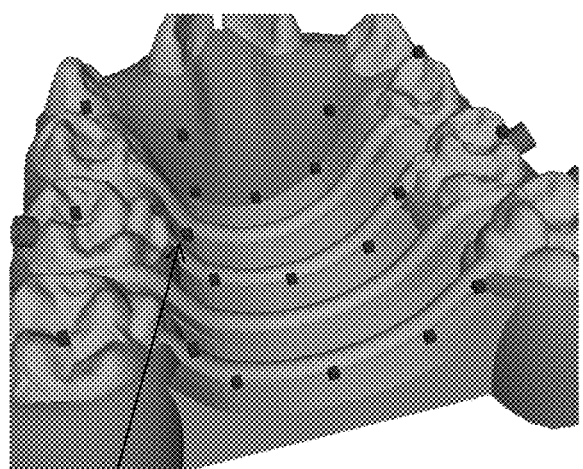
FIG. 24A
2403
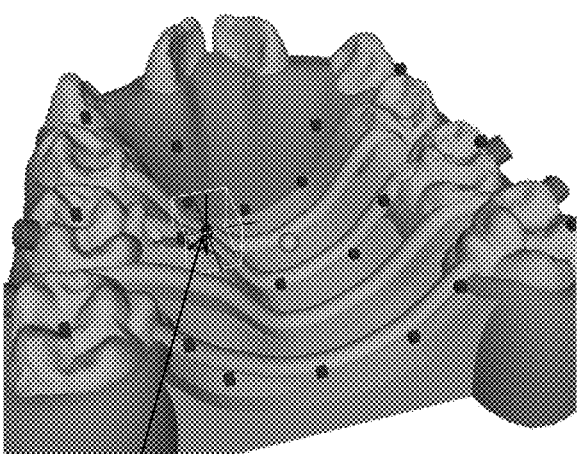
FIG. 24B
2403
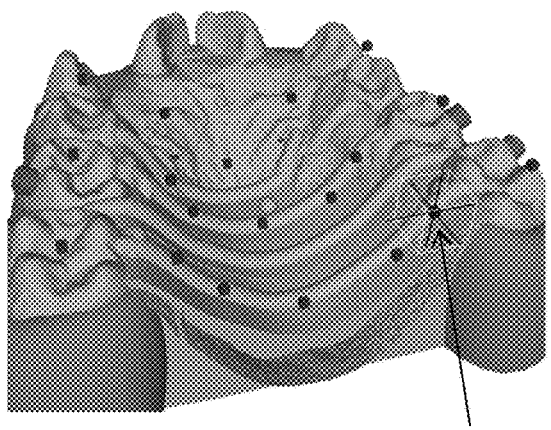
FIG. 24C  2403'
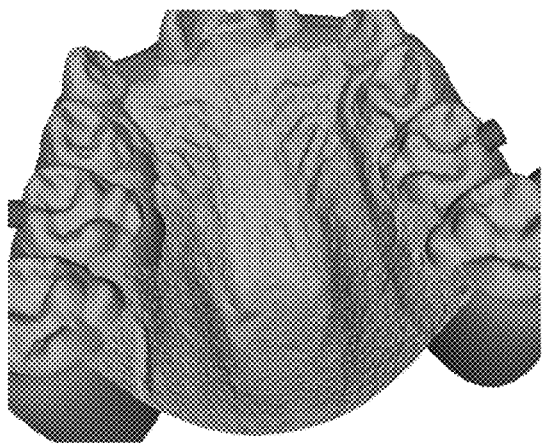
FIG. 25A
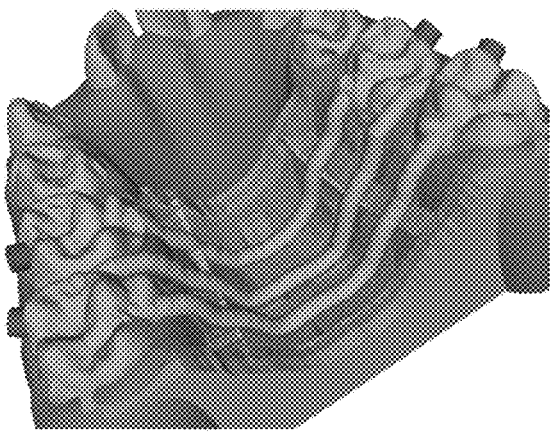
FIG. 25B

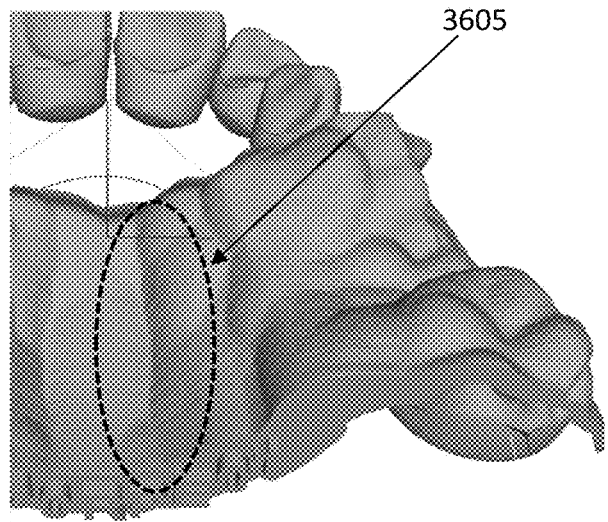 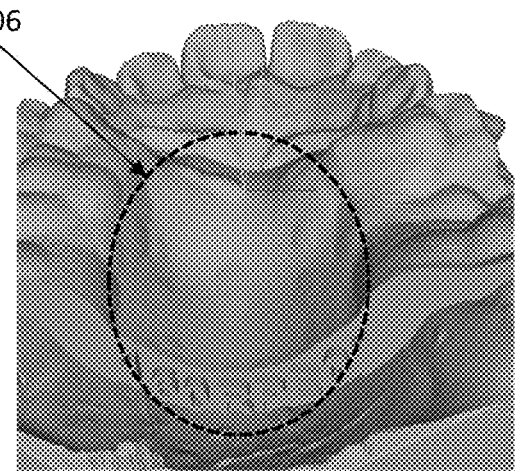
FIG. 36A          FIG. 36B
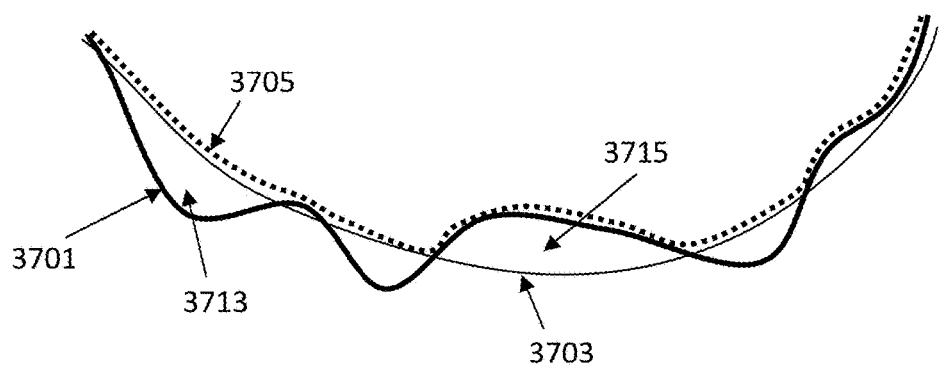
FIG. 37

PALATAL EXPANDERS AND METHODS OF DESIGNING PALATAL EXPANDERS

CROSS REFERENCE TO RELATED APPLICATIONS

This patent application is a continuation of U.S. patent application Ser. No. 18,158,451, filed Jan. 23, 2023, titled "SERIES OF PALATIAL EXPANDERS FOR CONTROLLING CROWN TIPPING," which is a continuation of U.S. patent application Ser. No. 17/100,784, filed Nov. 20, 2020, titled "METHODS AND APPARATUSES FOR CUSTOMIZING A RAPID PALATAL EXPANDER," now U.S. patent application Ser. No. 11,576,754, which is a divisional of U.S. patent application Ser. No. 15/831,262, filed Dec. 4, 2017, titled "METHODS AND APPARATUSES FOR CUSTOMIZING A RAPID PALATAL EXPANDER," now U.S. Pat. No. 10,993,783, which claims priority to U.S. Provisional Patent Application No. 62/429,696, titled "METHODS AND APPARATUSES FOR CUSTOMIZING A RAPID PALATAL EXPANDER" and filed Dec. 2, 2016, herein incorporated by reference in its entirety. This application may also be related to U.S. patent application Ser. No. 15/831,159 titled "PALATAL EXPANDERS AND METHODS OF EXPANDING A PALATE" by Shanjani et al., filed Dec. 4, 2017, which is also incorporated by reference in its entirety herein.

This application may also be related to U.S. Patent Application Publication No. 2016/0081768 (titled "ARCH EXPANDING APPLIANCE") and U.S. Patent Application Publication No. 2016/0081769 (titled "ARCH ADJUSTMENT APPLIANCE"), each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are palatal expanders, methods of making and methods of using them. For example, described herein are series' of palatal expanders that are ordered to provide incremental palatal expansion (including rapid or gradual palatal expansion) and methods of fabricating series of palatal expanders that are customized to a patient.

BACKGROUND

A variety of orthodontic problems are linked with a narrow palate. In certain circumstances the maxilla the size to accommodate the upper teeth. In other cases there is room for the upper teeth but the palate is so narrow that speech is impaired or made difficult. In other cases the palate is so high that it cuts down on the amount of air that can pass through the nose, so that deep breathing, without opening the mouth, is almost impossible. In all of these cases, palate expansion, that is separating and spreading the maxilla, may be helpful.

The palatal expansion device which is most commonly used in the prior art is affixed to the upper posterior molars usually with cement. A screw or other mechanism is employed to deliver a horizontal stretching force to the molars to stretch the palatal cartilage. In many cases, a large horizontal force is delivered by the orthodontist upon placement. This can cause extreme discomfort including headaches, nasal discomfort and pain. In other cases the screw or other mechanism is employed incrementally one or more times a day. While this incremental approach eases some of the discomfort such devices, the incidence of discomfort remains high. Moreover, the devices are awkward and bulky, largely due to the mechanism. This bulkiness can cause difficulty with speech, swallowing and breathing. The screw or other mechanism can be difficult to operate and often involves use of a key which can be accidentally lost or swallowed. In addition these devices tend to accumulate plaque.

Other problems encountered are that prior art devices tend to tilt the teeth buccally (i.e., to angle toward the checks) rather than stretch the palate. Palatal expansion is most favorable if movement of the teeth that engage the expansion device is minimized in relative to the jaw (which is moved in the palatal expansion process).

Described herein are methods and apparatuses that may address these concerns.

SUMMARY OF THE DISCLOSURE

Apparatuses (including devices and systems) and method for progressively expanding the palate of a patient may include palatal expanders that are fabricated from a model, including in particular a digital model, of a patient's mouth, including the patient's dentation (e.g., teeth), gingiva and palate.

Provided are methods and apparatuses (including systems and devices) for progressive palatal expansion. For example described herein are systems for palatal expansion that may include a series of incremental expanders including a first incremental expander having a geometry selected to expand the palate, one or more intermediate expanders having geometries selected to progressively expand the palate to a target desired breadth. A final expander may be used to retain the palatal expansion in the patient over a post-treatment period, and/or may be used to begin or prepare the patient for further dental alignment, including alignment of the patient's teeth. In particular, described herein are methods and apparatuses for forming a series of palatal expanders that are customized to a patient's oral cavity.

Any of the methods or apparatuses for forming a series of palatal expanders described herein may personalize the series of palatal expanders by modeling both the movement of the palate (and accurately estimating the new surface of the palate as it expands) and optionally in some variations, the movement of teeth within the patient's jaw bone, and use this modeling to design the series of palatal expanders. For example an apparatus or method for forming a series of expanders may be configured to include: receiving a digital model of the patient's oral cavity in an initial position; adjusting the digital model from the initial position to a final position in which the palate is expanded by morphing the digital model to reflect an orthopedic expansion of the patient's midline suture (and optionally an orthodontic movement of the patient's teeth within the patient's jaw); generating a palatal expander model corresponding to each intermediate position of a plurality of intermediate positions of the digital model between the initial position and the final position, wherein the plurality of intermediate positions are based on one or more of: a stiffness of the palatal expander, and a limit on an increment of change in at least one of the patient's palate and teeth; and fabricating a series of palatal expanders from the palatal expander model corresponding to each intermediate position of a plurality of intermediate positions.

A method and apparatuses for forming a series of palatal expanders may include: receiving a digital model of the patient's oral cavity in an initial position, wherein the digital model comprises a digital model of the patient's teeth, gingiva and palate; adjusting the digital model from the initial position to a final position in which the palate is expanded by morphing the digital model to reflect an orthopedic expansion of the patient's midline suture and an orthodontic movement of the teeth within the patient's jaw; generating a palatal expander model corresponding to each intermediate position of a plurality of intermediate positions of the digital model between the initial position and the final position, wherein the plurality of intermediate positions are based on: a stiffness of the palatal expander, and a limit on an increment of change in at least one of the patient's palate and teeth, wherein the increment of change comprises one or more of: a rate of expansion between the molars, an amount of force applied to the patient's oral cavity, a rate of dental movement of the patient's teeth, and a rate if change of an angle between a left and a right portion of the palate; and fabricating a series of palatal expanders from the palatal expander model corresponding to each intermediate position of a plurality of intermediate positions.

For example any of the methods or apparatuses described herein may be configured to form a series of palatal expanders by: receiving a digital model of the patient's oral cavity in an initial position (the digital model may comprise one or more of: a digital model of the patient's teeth, gingiva, palate, and the patient's lower jaw); optionally, segmenting the digital model of the patient's oral cavity into a palate model and/or a tooth model and/or a gingiva model; adjusting the digital model from the initial position to a final position in which the palate is expanded by morphing the digital model to reflect an orthopedic expansion of the patient's midline suture and an orthodontic movement of the teeth within the patient's jaw (e.g., based on an expansion axis); and generating a palatal expander model (e.g., digital palatal expander model) corresponding to each of a plurality of intermediate positions of the digital model between the initial position and the final position, wherein the plurality of intermediate positions are based on: a stiffness of the palatal expander and a limit on an increment of change in at least one of the patient's palate and teeth. For example, the increment of change may be one or more of: a rate of expansion between the molars (e.g., of about 0.25 mm per intermediate position or day); an amount of force applied to the patient's oral cavity (e.g., between the molars, of between about 8 N to 160 N, etc.); a rate of dental movement of the patient's teeth (e.g., of about 0.1 mm/day, about 0.09 mm/day, about 0.08 mm/day, about 0.07 mm/day, about 0.06 mm/day, about 0.05 mm/day, about 0.04 mm/day, about 0.035 mm/day, about 0.03 mm/day, etc.); and a rate of change of an angle between a left and a right portion of the palate (e.g., of about 1 degree/day).

Any of the method and apparatuses described herein for forming a series of palatal expanders may be configured to estimate or model the movement of different portions of the palate (e.g., a right side and a left side of the palate) in relation to an expansion axis in a mid-plane of the patient's face (e.g., extending between the patient's nose and a back of the patient's upper jaw). For example, a method for forming a series of palatal expanders may include: receiving a digital model of the patient's oral cavity in an initial position, wherein the digital model comprises a digital model of the patient's teeth, gingiva and palate; adjusting the digital model from the initial position to a final position in which the palate is expanded by morphing the digital model to reflect an orthopedic expansion of the patient's midline suture and an orthodontic movement of the teeth within the patient's jaw based on rotation about an expansion axis in a mid-plane of the patient's face extending between the patient's nose and a back of the patient's upper jaw; generating a palatal expander model corresponding to each intermediate position of a plurality of intermediate positions of the digital model between the initial position and the final position; and fabricating a series of palatal expanders from the palatal expander model corresponding to each intermediate position of a plurality of intermediate positions.

Typically, expanders have been described as pre-formed devices having a first molar-engaging region adapted to engage upper molars on a first side of the upper jaw, a second molar-engaging region adapted to engage upper molars on a second side of the upper jaw and palatal region with a geometry selected to fit against the shape of the palate while providing pressure to incrementally expand the palate. Each of the expanders in a series of expanders may comprise two molar regions, one on each side, each with one or more cavities, each cavity being adapted to fit over one of the patient's molars. In an especially preferred embodiment each molar region comprises two cavities, such that each molar region fits over two posterior molars or premolars. Each expander may further comprise a palatal region, which separates the two molar regions and fits against the patient's palate. Typically, the distance between the molar regions in the series of expanders is sequentially greater.

The palatal region of the device may provide force to stretch or expand the mid-palatal region. Although energy-enhancing features may be placed in this region (e.g., springs and thermally active materials), in addition, this region may include on or more adaptations, such as struts, supports, cross-beams, ribs, gaps/windows, attachments, and the like which may distribute the forces applied in a more nuanced manner than previously described. For example, these devices may be configured so that the forces applied are distributed in a predetermined and/or desired pattern by arranging one or more points of contact between the palatal expander and the patient's mouth (e.g., in the gingiva and/or preferably along an upper or lower lateral portion of the patient's teeth, including their molars). The curvature (e.g., concavity) of the device may also be adjusted, to distribute the forces applied, while allowing clearance between the palate and the device, and/or allowing clearance for the user's tongue.

A series of palatal expanders as described herein may be configured to expand the patient's palate by a predetermined distance (e.g., the distance between the molar regions of one expander may differ from the distance between the molar regions of the prior expander by not more than 2 mm, by between 0.1 and 2 mm, by between 0.25 and 1 mm, etc.) and/or by a predetermined force (e.g., limiting the force applied to less than 100 Newtons (N), to between 8-100 N, between 8-90 N, between 8-80 N, between 8-70 N, between 8-60 N, between 8-50 N, between 8-40 N, between 8-30 N, between 30-60 N, between 30-70 N, between 40-60 N, between between 60-200 N, between 70-180 N, between 70-160 N, etc., including any range there between). These devices and apparatuses may be configured to limit the movement and/or forces applied to within these ranges.

In any of the apparatuses described herein (and methods of fabricating them), the expanders may be formed out of a polymer and/or a metal material, including stainless steel, nickel titanium, copper nickel titanium, etc. In particular, described herein are laminated apparatuses, in which the apparatuses are formed for layers of material that may be formed and/or adhered together (e.g., to form a unitary device); different layers may have different mechanical and/or chemical properties, and may include different thicknesses or regions of thickness. For example, an apparatus may include laminated materials that are bonded together.

The apparatuses and method of forming them may include fabricating one or more of the expanders by direct fabrication techniques. For example, an apparatus (including a series of palatal expanders) may be digitally designed and fabricated by a direct printing (e.g., 3D printing); alternatively or additionally the fabrication method may include 3D printing of models of the teeth, gingiva and palate that have been digitally configured to form one or more of the series applying the palatal expansion.

Also described herein are methods of expanding the palate of a patient using any of the apparatuses described herein, which may include positioning each expander in a series of expanders in position to expand the palate, leaving the expander in position for a period of time and replacing the expander with the next expander in the series until the desired palatal expansion has occurred and then applying a palatal expander that is configured to retain the palate in the final position at the target desired breadth. Any of the methods of forming a series of palatal expanders describe herein may generally include: dividing a digital model of a patient's upper jaw into a left maxillary side and a right maxillary side; forming a plurality palatal expansion models of patient's upper jaw, wherein for each palatal expansion model, the left maxillary portion and the right maxillary portion are progressively translated relative to their original position; and generating a series of palatal expanders, wherein each palatal expander in the series corresponds to one of the palatal expansion models, further wherein each palatal expander comprises a tooth engagement region configured to be removably worn over the patient's teeth, and a palatal region.

Any of the methods of forming a series of palatal expanders described herein may include: dividing a digital model of a patient's upper jaw into a left maxillary side and a right maxillary side; forming a plurality palatal expansion models of patient's upper jaw from the digital model, wherein for each palatal expansion model, the left maxillary portion and the right maxillary portion are progressively translated relative to their original position in the digital model, wherein forming the plurality of palatal expansion models further comprises morphing the digital model to reflect an orthopedic expansion of the patient's midline suture; and generating a series of palatal expanders, wherein each palatal expander in the series corresponds to one of the palatal expansion models, further wherein each palatal expander comprises a tooth engagement region configured to be removably worn over the patient's teeth, and a palatal region.

For example, a method of forming a series of palatal expanders may include: dividing a digital model of a patient's upper jaw into a left maxillary portion and a right maxillary portion; forming a plurality of palatal expansion models of the patient's upper jaw, wherein for each palatal expansion model, the left maxillary portion and the right maxillary portion are progressively translated and rotated relative to their original positions (e.g., with respect to a mid-sagittal plane and/or a line passing through the mid-sagittal plane); generating a series of palatal expanders, wherein each palatal expander in the series corresponds to one of the palatal expansion models, further wherein each palatal expander comprises a tooth engagement region configured to be removably worn over the patient's teeth, and a palatal region. In any of these methods, forming the plurality of palatal expansion models may comprise translating and rotating the left maxillary portion and the right maxillary portion so that an anterior gap formed between the left maxillary portion and the right maxillary portion is different than a posterior gap formed between the left maxillary portion and the right maxillary portion.

As used herein, rotation of a left and/or right maxillary portion relative to a plane such as the mid-sagittal plane may refer to rotation of the left and right maxillary portions relative to a line or point laying in the mid-sagittal plane, such as an expansion axis as described in greater detail herein. This rotation may be symmetric between the left and right maxillary portions, or it may be asymmetric.

In general, progressively translating the left and right maxillary sides (side portions) may result in an anterior space between the left and right maxillary sides expanding faster than the gap between the left maxillary portion and the right maxillary portion. For example, described herein are methods of forming a series of palatal expanders comprising: forming a plurality palatal expansion models of patient's upper jaw, wherein for each palatal expansion model, a left maxillary portion and a right maxillary portion are progressively translated relative to an expansion axis extending in a plane through a midline of the upper jaw so that an anterior gap formed between the left maxillary portion and the right maxillary portion is larger than a posterior gap formed between the left maxillary portion and the right maxillary portion; generating a series of palatal expanders, wherein each palatal expander in the series corresponds to one of the palatal expansion models, further wherein each palatal expander comprises a tooth engagement region configured to be removably worn over the patient's teeth, and a palatal region configured to be worn adjacent to the patient's palate. The method may also include dividing a digital model of a patient's upper jaw into a left maxillary portion and a right maxillary portion. Dividing the digital model of the patient's upper jaw into the left maxillary portion and the right maxillary portion may comprise dividing the digital model of the patient's teeth and palate about the plane through the midline of the upper jaw. Forming may be digitally forming (e.g., forming, in a processor performing the steps or with the aid of a processor performing these steps). As used herein, the left maxillary portion may refer to the left maximally half and the right maxillary portion may refer to the right maxillary half; these halves may not refer to an exact measure of the percent of the maxillary region (e.g., 50% of the maxillary region), but may generally refer to the left side (left half or left portion) and right side (right half or right portion).

Alternatively, in any of the methods and apparatuses described herein, translating the left and right maxillary sides (side portions) may result in an anterior space between the left and right maxillary sides expanding slower than the gap between the left maxillary portion and the right maxillary portion. This may be desirable, for example, to minimize a diastema (space) between the anterior teeth that may otherwise form when expanding the patient's palate.

In general, forming the plurality of palatal expansion models may comprise progressively tipping the left maxillary portion about the expansion axis in a first direction and progressively tipping the second maxillary portion about the expansion axis in a second direction. For example, the left maxillary portion and a right maxillary portion may be progressively translated by both moving in an x direction (e.g., left-right direction) relative to the expansion axis, and rotational translation as the left and right sides tip about the expansion axis.

Any of these methods may also include determining a final expanded position for the patient's upper jaw before forming the plurality palatal expansion models, wherein in the final expanded position the anterior gap between the left maxillary portion and the right maxillary portion is larger than a posterior gap between the left maxillary portion and the right maxillary portion.

Forming the plurality of palatal expansion models may comprise including a plurality of attachments on the patient's teeth, wherein the tooth engagement region of each of the plurality of palatal expanders is configured to mate with the plurality of attachments.

Any of the methods may include preparing digital files for manufacturing, directly or indirectly, the palatal expanders (e.g., "shell" palatal expanders, such as those described herein that are worn over the teeth and adjacent to the palate once inserted by the user or caregiver over the teeth). Generating a series of palatal expanders may comprise generating a plurality of data files, wherein each data file in the plurality of data files corresponds to one of the palatal expanders of the series of palatal expanders. Generating the series of palatal expanders may comprise directly fabricating the series of palatal expanders from the plurality of data files, e.g., by 3D printing or related techniques.

Generating the series of palatal expanders comprises, for each palatal expander, digitally modeling a bottom surface using the corresponding palatal expansion model, digitally modeling a top surface that is offset from the bottom surface by a thickness, and adjusting the thickness so that an average thickness of the palatal region is different than (e.g., greater than) an average thickness of an occlusal region of the tooth engagement region, and an average thickness of a buccal region of the tooth engagement region is different than (e.g., less than) the average thickness of the occlusal region.

As will be described in greater detail herein, any of these methods may include digitally smoothing the top surface.

Forming the plurality palatal expansion models of patient's upper jaw may comprise, for each palatal expansion model, morphing a digital model of the patient's palate as the left maxillary portion and the right maxillary portion are progressively translated.

The tooth engagement region may comprise an occlusal side and a buccal side, further wherein the occlusal side may have a different thickness (e.g., may be thinner) than the palatal region, and the buccal side may have a different thickness (e.g., may be thinner) than the occlusal side.

Any of these methods may include receiving the digital model of the patient's upper jaw, either directly (e.g., from an intraoral scanner) or indirectly, e.g., by scanning a model or cast of the patient's teeth.

For example, a method of forming a series of palatal expanders may include: dividing an initial digital model of a patient's upper jaw into a left maxillary portion and a right maxillary portion; determining a final expanded position for the patient's upper jaw, wherein in the final expanded position an anterior gap between the left maxillary portion and the right maxillary portion is larger than a posterior gap between the left maxillary portion and the right maxillary portion; forming a plurality of intermediate palatal expansion models of the patient's upper jaw between the initial digital model of a patient's upper jaw and the final expanded position of the patient's upper jaw, wherein for each intermediate palatal expansion model, the left maxillary portion and the right maxillary portion are progressively translated relative to an expansion axis extending in a plane through a midline of the upper jaw so that an anterior gap formed between the left maxillary portion and the right maxillary portion is larger than a posterior gap formed between the left maxillary portion and the right maxillary portion; generating a series of palatal expanders, wherein each palatal expander in the series corresponds to one of the intermediate or final palatal expansion models, further wherein each palatal expander comprises a tooth engagement region configured to be removably worn over the patient's teeth, and a palatal region configured to be worn adjacent to the patient's palate.

Also described herein are series of palatal expanders configured to be sequentially worn by a patient to expand the patient's palate, wherein the patient's upper jaw comprises a left maxillary portion and a right maxillary portion. For example, the series of palatal expanders may comprise, for each palatal expander in the series: a left tooth engagement region configured to be removably worn over the patient's teeth in the left maxillary portion, a right tooth engagement region configured to be removably worn over the patient's teeth in the right maxillary portion, and a palatal region configured to be worn adjacent to the patient's palate, wherein a ratio of an anterior-most distance between the left tooth engagement region and the right tooth and the posterior-most distance between the left tooth engagement region and the right tooth engagement region increases with the series, so that palatal expanders configured to be worn earlier in the series have a lower ratio than palatal expanders configured to be worn later in the series.

For each palatal expander, a top surface of the palatal expander may be offset from a bottom surface by a thickness such that an average thickness of the palatal region is greater than an average thickness of an occlusal region of the left and right tooth engagement regions, and an average thickness of a buccal region of the left and right tooth engagement regions is less than the average thickness of the occlusal region.

In any of these series, a tilt angle between the left tooth engagement region is and the right tooth engagement region may increase with the series, so that palatal expanders configured to be worn earlier in the series have a lower tilt angle than palatal expanders configured to be worn later in the series, further wherein the tilt angle is an angle relative to a plane through a midpoint of the teeth of the patient's upper jaw in an initial position of the patient's teeth in the upper jaw.

For each palatal expander in the series, a top surface may be configured to face the patient's tongue when the palatal expander is worn is smoother than a bottom surface configured to face the patient's palate when worn. Each palatal expander may comprises a monolithic palatal expander. Further, for each palatal expander in the series, the left tooth engagement region may comprises a left buccal extension region configured to extend at least partially over the patient's gingiva when the palatal expander is worn by the patient. Each palatal expander in the series may comprise a visible identification marking on a flat posterior surface, wherein the identification marking encodes one or more of: a patient number, a revision indicator, an indicator that the apparatus is a palatal expander or a retainer, and the stage of treatment.

Any of the methods and apparatuses described herein may be configured so that a physician's input (e.g., orthodontist, dentist, etc.) may be included as part of the design parameters (e.g., design characteristics) when designing the palatal expanders. For example, any of the methods described herein may permit user (e.g., physician) input to be included in the design of the individual and/or series of palatal expanders. For example a user interface may present the user with a graphic display of the digital model of the arch (upper and/or lower arch) from an initial position of the teeth and arch, allow the user to modify the digital model to generate or select the final position, and/or the sequence or series of palatal expanders. The user interface may also allow the user to select parameters such as the number and location of attachments, the size (e.g., width, thicknesses, etc.) of the palatal region of the palatal expander, the separation between the palatal expander and all or portions of the patient's palate when the apparatus is worn, the force (e.g., maximum force) applied by the palatal expander, the presence and/or extent of any detachment region (e.g., on the buccal side), etc.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 7 is an example of an expander including a cut-out region (shown here as a slit) that is not connected to an opening.

FIGS. 8A-8H illustrate a variety of examples of openings and cut-out regions and attachments between an expander and a patient's teeth or an attachment on a patient's teeth (e.g., connections between the patient's teeth and an expander appliance), including openings having different sizes and/or shapes.

FIG. 9B shows a section through line A-A of FIG. 9A.

FIG. 11B shows the non-uniform expansion of the mid-palatal suture in which the anterior region separates more than the posterior region. FIG. 11C is a front view of the maxilla shown in FIG. 11B, illustrating tipping of the right and left maxillary halves.

FIG. 11D shows the teeth before palatal expansion and FIG. 11E shows the same teeth after palatal expansion.

FIGS. 13A-13D illustrate partitioning a digital model of a patient's oral cavity into different regions (e.g., tooth, gingiva, palate).

FIGS. 14A-14D illustrate movement of portions of a digital model of the patient's oral cavity (e.g., palate and/or teeth) about an expansion axis.

FIG. 15A is not expanded and FIG. 15B show the palate expanded by rotation about an expansion axis.

FIG. 16A is not expanded and FIG. 16B is expanded about an expansion axis.

FIGS. 19A and 19B show an example of expansion of a middling region of the palate from an unexpanded view (FIG. 19A) to an expanded view (FIG. 19B) by rotation about an expansion axis.

FIGS. 20A and 20B illustrate a gap created in the digital model when expanding the palate (from an unexpanded view in FIG. 20A to an expanded view in FIG. 20B).

FIGS. 21A-21C illustrate one method of morphing the palate region to fill in a gap formed by palatal expansion.

FIGS. 22A and 22B show views of a digital model of a patient's oral cavity before (FIG. 22A) and after (FIG. 22B) simulated expansion, showing morphing of the palate after expansion in FIG. 22B.

FIGS. 24A-24C illustrate adjusting the shape of a palatal expander (e.g., the palatal region or TPA) as described herein.

FIGS. 25A and 25B illustrate another method of designing and/or forming an expander as described herein.

FIG. 34A shows a schematic showing calculation of offsets. FIG. 34B shows an example of a portion of a palatal expander formed from the schematic of FIG. 34A.

FIGS. 36A and 36B illustrate smoothing of a palatal center region of an expander.

FIG. 37 illustrates one smoothing method that may be used to smooth a surface (e.g., the tongue-facing surface) of a palatal expander.

FIG. 39A shows the un-smoothed surface, while FIG. 39B illustrates an intermediate step in smoothing and FIG. 39C shows the smoothed final surface.

DETAILED DESCRIPTION

Figure 1:
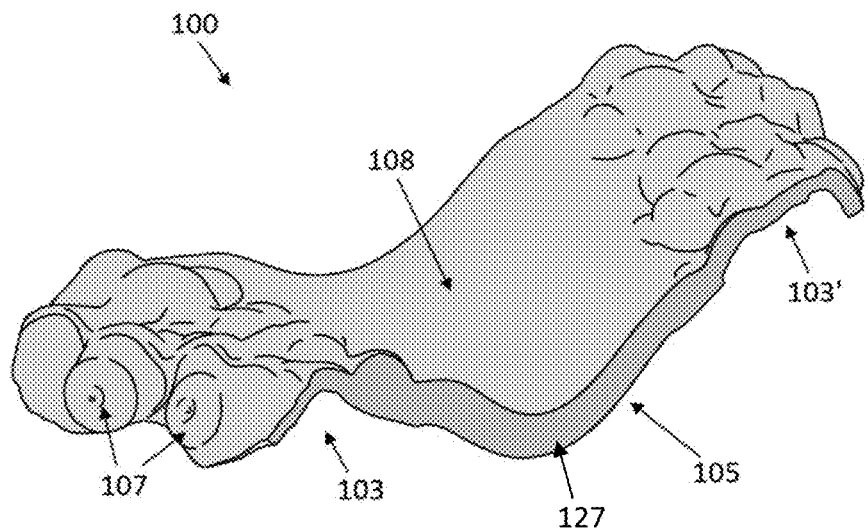
FIG. 1 illustrates one example of a palatal expander including an enclosed attachment that may aid in retention within the oral cavity.

In general, the palatal expansion apparatuses described herein are worn as a series of expanders by a patient. These palatal expanders may be configured to apply force within the patient's mouth to expand the patient's maxilla. In particular, described herein are apparatuses, e.g., devices and/or systems, including individual palatal expanders and/or a series or sequence of palatal expanders, and methods of making and using such apparatuses. The methods and apparatuses described herein include methods and apparatuses (e.g., systems, including software, hardware and/or firmware) for planning and generating a sequence of palatal expanders that may more comfortably and efficiently move the patient's left and right maxillary halves. These methods may limit the force and/or rate of movement delivered by each palatal expander in a sequence of expanders. Any of these methods and apparatuses may also account for translation and tipping of the left and right maxillary halves as treatment progresses, and may also optionally account for tipping of the teeth, and changes in the shape (morphology) of the palate as treatment progresses.

Described herein are methods of forming palatal expansion apparatuses. These apparatuses may be configured to apply between 8-120 N of force to expand the patient's palate. These apparatuses may be considered 'slow' expansion apparatuses (e.g., applying around 8-10 N of force between the molars on either side of the upper jaw of the mouth), or 'rapid' expansion apparatuses (e.g., applying greater than 60 N for higher speed expansion, e.g., between 70 and 160 N). In some variations, the apparatuses may be configured to drive displaced and/or force. For example, any of these apparatuses may be configured to drive displacement of between about 0.25 mm/day (when worn for a 24 hour wear time). These apparatuses (e.g., devices) may form a series of devices that may be used to displace the palate, expanding it and causing transverse force between the molars on either side of the mouth.

In general, the devices described herein may include an offset between the upper surface of the mouth (the palatal surface) and the palatal expander. This offset may be, for example, between 0.1 mm and 10 mm (e.g., between 0.2 mm and 9 mm, between 0.3 mm and 9 mm, between 0.5 mm and 8 mm, between 1 mm and 7 mm, between 2 mm and 5 mm, etc., including any region or sub-regions there between). This gap may prevent soft tissue irritation. The gap may extend over 50% of the portion of the apparatuses that are positioned opposite of the patient's palate, when worn by the patient (e.g., over 60%, over 70%, over 80%, over 90%, over 95%, etc.). The gap may be centered in the mid-palatal region (e.g., along the mid-palatine suture, etc.). In some variations, the shape of the palatal portion of the expander (e.g., the portion opposite the patient's palate when worn by the subject) may be contoured on the patient-facing side) to match the contour of the patient's palate (either with or without an offset, as just described) and may include ridges, channels, etc. In contrast, the opposite surface of the palatal region (e.g., the lingual, tongue-facing side) may be smoothed and may have a very different As will be described in greater detail below, the shape of the apparatus (e.g., the expander), and therefore the load (e.g., force) applied by the apparatus when worn, may be controlled and selected during the fabrication process. It may be particularly advantageous to provide a digital planning process in which a digital model of the patients upper jaw (e.g., teeth, palate and gingiva), and in some cases the subject's lower jaw (e.g., teeth and/or gingiva) may be modified to plan the series of expanders that morph between the patient's initial anatomy to an expanded configuration in which the final expanded configuration is described. Designing an accurate and effective series of palatal expanders should ideally accurately model the palatal expansion to include both linear translation (e.g., in an xy plane) and tipping (e.g., rotational translation) of the right and left maxillary halves, and optionally include translation of one or more of the teeth, including tipping of the teeth due to the forces applied by the palatal expander. Optionally, as described herein, the design of a series of palatal expanders may also include an effect on the lower jaw, and in particular the interaction between the lower and upper jaw (e.g., intercuspation). Superior results may be achieved by accurate digital modeling of the teeth, gingiva and palate of the upper jaw (and in some variations the teeth of the lower jaw), and by controlling the planned movement (e.g., expansion of the palate, which may be expressed as the separation between the molars) and the forces acting on one or more of the teeth, palate and/or gingiva. In addition, the palatal expanders may also be digitally modeled, including modeling both the shape (dimensions, including thickness, curvature, attachment points, etc.) and the material(s) used. Thus, the expander(s) in a series of expanders may be accurately and in some cases automatically, configured so that they achieve the desired palatal expansion within predetermined (or user/physician/technician) adjustable parameters such applied expansion force (e.g., between x and y N, less than y N, etc., where x is about 5, 6, 7, 8, 9, 10, 15, 20, 25, 30, 35, 40, 45, 50, 60, 70, etc. and y is about 10, 20, 30, 40, 50, 60, 70, 80, 90, 100, 110, 120, etc. and is less than x), the location of applied forces in the patient's mouth (e.g., upper lateral portion of the molars, mid-lateral portion of the molar, lower lateral portion of the molars, gingiva, palate, etc.) and/or portions of the patient's mouth to avoid contact (e.g., gingiva, palate, mid-palate, lateral palate, etc.).

Expander Features

The palatal expanders described herein may include a tooth engagement region for engaging at least a portion of the teeth in the patient's upper jaw, in particular the molars, and a palatal region extending between the tooth engaging region that is configured to be positioned adjacent and opposite from the patient's palate when the device is worn by the patient. For example, FIG. 1 shows an example of a palatal expander 100 that includes a pair of tooth engagement regions 103, 103' on either side of the device, connected by a palatal region 105. In this example, the palatal expander also includes a pair of attachment regions 107 that may each enclose an attachment connector that is bonded to the patient's teeth, e.g., on either side of the device (on a buccal side of the patient's teeth; only one pair is visible). The attachment connector (also referred to herein as a connector, pin, attachment, or the like) may be secured to the teeth in a position that allows it to couple (e.g., removably couple) to the attachment region(s) on the expander. An attachment connector may be bonded (glued, etc.) to the teeth as part of an initial step prior to wearing the series of expanders. In the apparatus shown in FIG. 1, the palatal region has a convex upper surface 127 that is opposite the concave lower surface 108. The lower surface is a lingual (tongue-facing) surface; the upper surface faces the palate.

The tooth engagement regions may be formed of the same material(s) as the palatal region, or they may include different materials. The thickness of the tooth engagement regions and the palatal regions may be different or the same. In particular, the palatal region may be thicker than the tooth engagement region. The thickness of the tooth engagement region may be thicker along the lateral (e.g., buccal and/or lingual) sides of the device and thinner (or removed from) across all or a portion of the top of the tooth engagement region. The palatal region may have a non-uniform thickness. For example, the palatal expander may be thicker near the midline of the device. Any of the palatal expanders may include ribs or other supports (e.g., extending transversely between the tooth engagement regions and/or perpendicular to the tooth engagement regions). These ribs may be formed of the same material as the rest of the palatal region (e.g., but be thicker and/or shaped to have a cylindrical cross-sectional profile).

The inner (cavity) portion of the tooth engagement region is typically configured to conform to the outer contour of the patient's teeth, and to rest directly against the teeth and/or a portion of the gingiva (or to avoid the gingiva) to apply force thereto. The upper surface of the palatal region which is positioned adjacent to the palate when worn by the patient may be contoured to match the actual or predicted shape of the patient's palate. As mentioned above, all or a significant portion of the palatal region may be separated or spaced from the patient's palate when worn, which may enhance comfort and minimize disruption of speech.

In some variations, a portion of the palatal region extending between the opposite tooth engagement regions on either side of the device (e.g., a portion of the palatal region extending approximately z % of the distance between the tooth engagement regions, where z is greater than about 30%, 40%, 50%, 60%, 70%, 80%, 90%, etc.) may be flat or straight, rather than curved, so that it does not necessarily follow the contour of the patient's mouth. This portion may be one or more transverse ribs, struts or supports, or it may be the flat sheet. Such a flat or straight portion may provide increase force. Alternatively or additionally, the palatal region (e.g., one or more ribs, the sheet, etc.) may be curved in an arc similar to the arc of the patient's palate, but may have a much larger radius of curvature (appearing as a shallower concavity) than the patient's palate.

Any of the palatal expanders described herein may include one or more attachment regions or sites (also referred to herein as attachment opening, attachment couplers, etc.) for coupling to an attachment connector on the patient's teeth. In particular, it may be helpful to use one or more (e.g., a pair) of attachment regions on each side of the device. Furthermore, the attachment sites may preferably be openings through the expander. An open structure (attachment site) on the orthodontic expander may interact with attachments (attachment connectors) located on teeth to improve the overall retention of the appliance and in some cases may be used to generate advantageous force features for teeth alignment, including limiting or preventing rolling of the teeth buccally as the palate is expanded. Such features may be helpful, in particular, when included as part of a directly fabricated (e.g., 3D printed) device for rapid (e.g., phase 1) palatal expansion. Described in FIGS. 2-9B are examples of attachments (e.g., attachment connectors/attachment sites) that may be used as part of any expander. Further, although the attachment connector is typically bonded to one or more teeth and projects into a complimentary opening or cavity on the expander, this configuration may be revered in some or all of these; for example, the protruding attachment connector may be part of the expander which may insert into an opening/cavity bonded to the user's teeth.

Any appropriate attachment region may be used, and in particular any appropriate size and/or shape may be used. As mentioned, the attachment region may preferably be an open structure on the appliance which may improve retention of the appliance over the attachments and possibly include force features for teeth alignment. For example the attachment region may comprise a round, oval, square, rectangular, triangular, etc. opening through the expander (e.g., at a lateral, e.g., buccal, side of the tooth regaining region of the expander. The attachment region may be keyed relative to the attachment connector; in general the attachment connector may be configured to mate with the attachment region in one or a particular orientation.

An open attachment region may reduce non-compliance of the appliance to poorly cured attachments. The open structures may enable complete coverage over a pre-determined attachment shape and size. Any of these attachment region/attachment connector couplings may incorporate biomechanical force features with this appliance/attachment interaction, including, as described above, keyed regions that transmit rotational force in the plane of the opening (e.g., against the surface of the tooth), for example. In some variations the attachment connector may snap or couple into the attachment region in a manner that requires a force to disengage the coupling.

Figure 2:
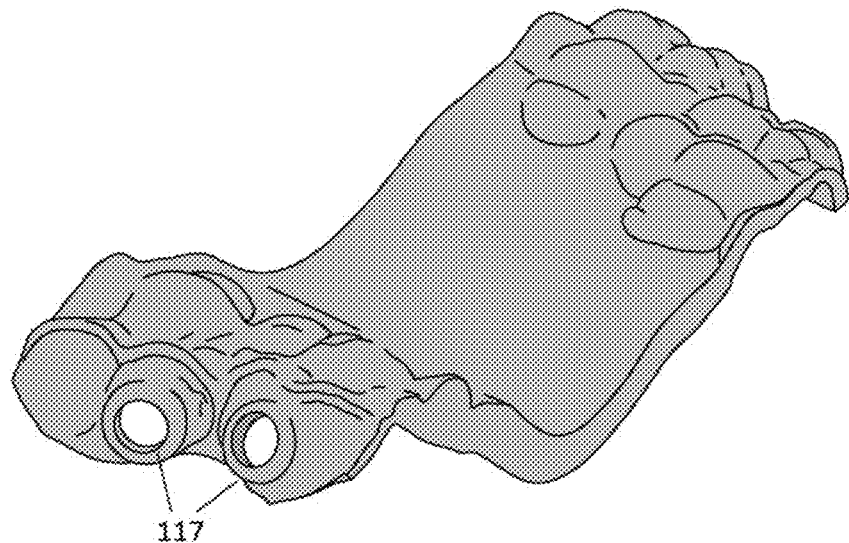
FIG. 2 is an example of a palatal expander having open attachments for retention and application of force.

As shown in FIG. 1, a conventional appliance design may enclose the attachment that helps maintain retention in the oral cavity. Alternatively, the variability in the size of these attachment regions due to appliance fabrication (e.g., thermoforming, direct fabrication, etc.) may be reduced by creating an open structure, as shown in FIG. 2. In FIG. 2, the separator is otherwise quite similar to what is shown in FIG. 1, but includes two open attachment regions 117.

Figure 3:
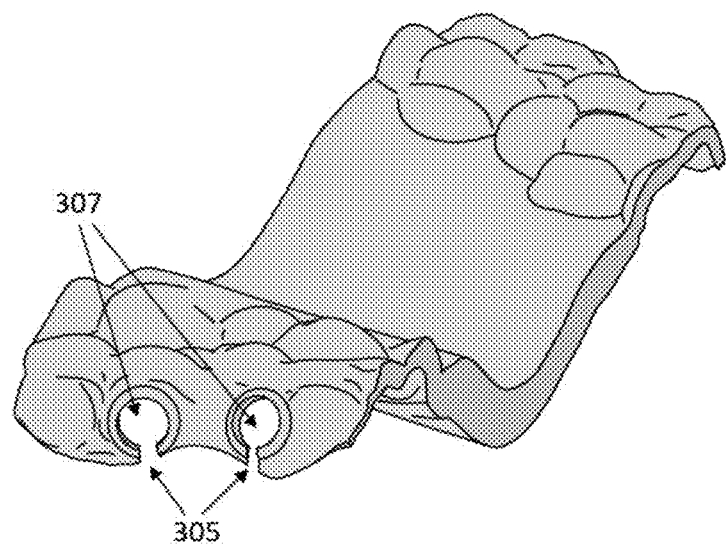
FIG. 3 shows an example of a palatal expander including open attachments and cut-out regions (shown here as slits into the open attachments).

In any of the apparatuses described herein, the device may also include one more cut-out regions in which the cut-out region (e.g., slot, slit, etc.) opens to a side or edge of the apparatus. A cut-out feature such as this may increase the flexibility of the adjacent region, such as the buccal surface. When connected to or adjacent to the attachment region opening, as shown in FIG. 3, this configuration may increase or decrease the retention to the attachment. In FIG. 3 cut-out region (slits 305) have been added to the open structures 307 to increase the flexibility of the appliance over the attachments.

Figure 4:
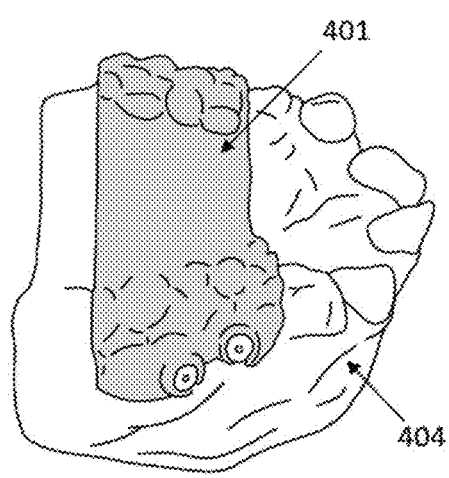
FIG. 4 is another example of an apparatus including slits connected to the open attachments in the expander, shown coupled to attachments (pins) on a mode of a patient's teeth.

FIG. 4 illustrates another example of a cut-out region (slit) between an opening (attachment region) adapted to couple with an attachment connector. In this example the attachment connector and coupling region are connected to secure the expander 401 to a (model of) patient's teeth 404.

Figure 5:
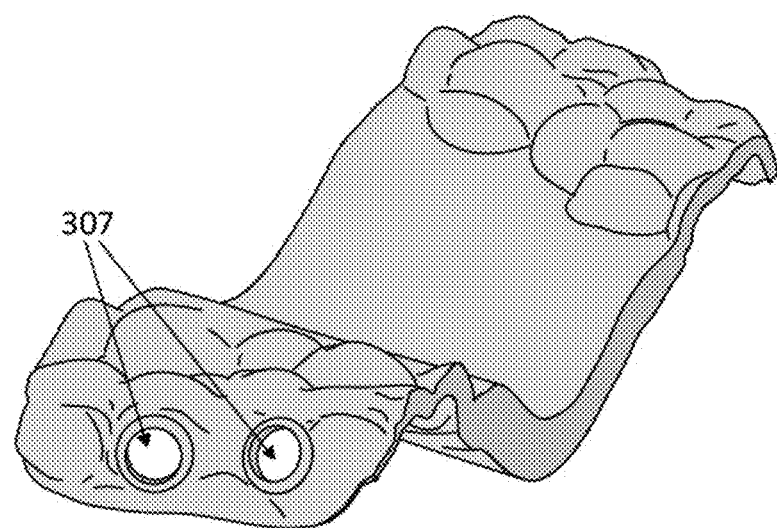
FIG. 5 is an example of an expander having open attachments that are positioned further from the edge of the apparatus (e.g., either by moving the bottom edge, or cut-line, closer to the gingiva or by moving the openings further up the teeth).

Another example of an expander with attachment regions comprising opening through the expander on the buccal side is shown in FIG. 5. The attachment regions may be formed at any location of the expander, including in particular the buccal side of the tooth engaging region. In FIG. 5, the openings are arranged up from the edge region of the buccal side of the tooth engagement region, so that the "cut-line" (when forming as a direct fabrication piece) above or at the gingival edge has been lowered to increase the mechanical strength around the open holes 307 to increase retention.

Figure 6:
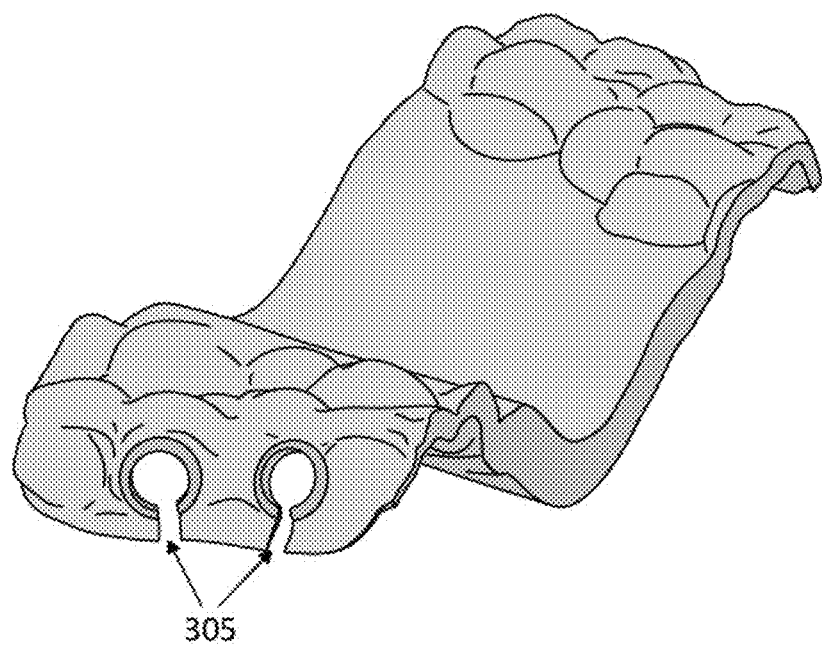
FIG. 6 shows an example of the apparatus of FIG. 5 including cut-out regions that may enhance flexibility and/or ease of application.

FIG. 6 shows the example of FIG. 5 with the addition of slits 305 to increase flexibility of the device at the edges (but not the palatal region) which may make it easier and faster to put on and/or remove. In FIG. 7, a slit between the open holes are added to created another dimension of flexibility that is different from that shown in FIG. 6. In FIG. 7 the slit is located between the two open attachment regions 30; alternatively or additionally slits (which typically run perpendicular to the edge of the device) may be located on one or both sides of the opening and/or into the openings, as shown in FIG. 6.

Figure 8I:
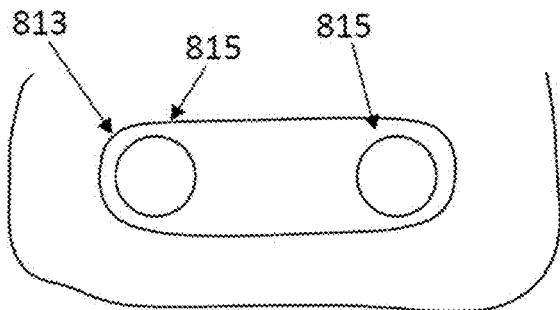
FIGS. 8I-8N illustrates further examples of openings, cut-out regions and attachments on a patient's teeth (e.g., connections between the patient's teeth and an expander appliance).
Figure 8J:
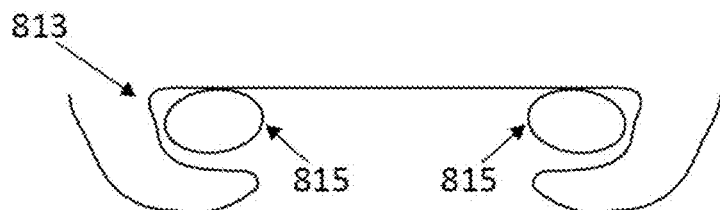
Figure 8K:
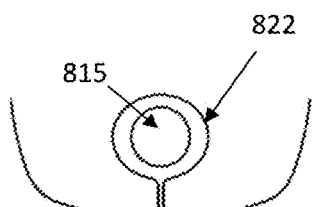
Figure 8L:
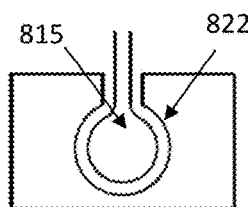
Figure 8N:
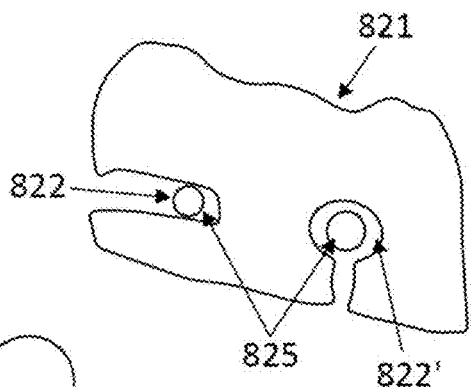
Figure 8M:
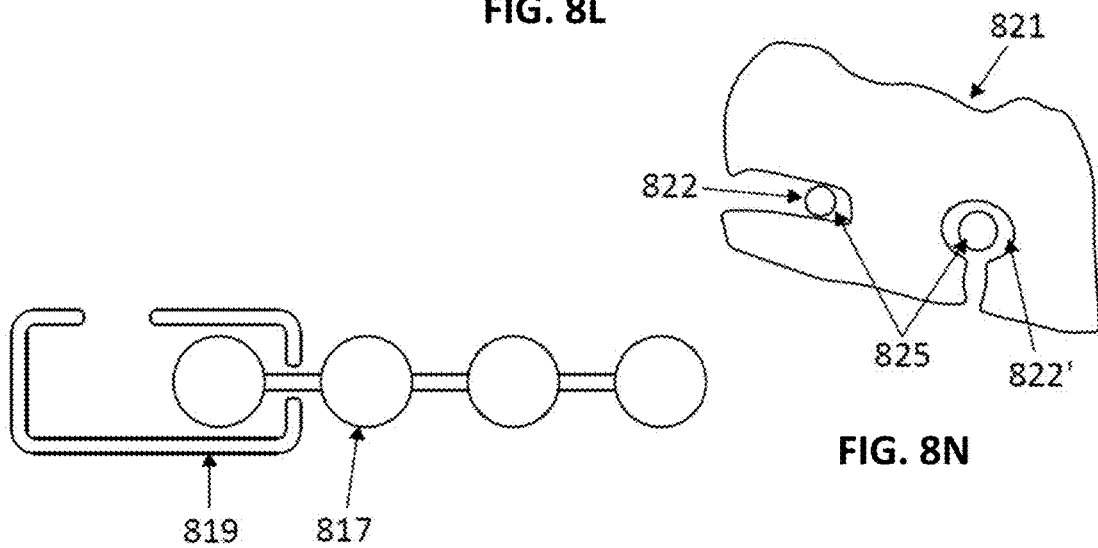

FIGS. 8A to 8N illustrate a variety of examples (unordered) of attachment sites. In some variations the attachment site is configured as a hook 803 (see FIG. 8B) attaching around an attachment connector 805 (e.g. post, protrusion, etc. connected to the tooth 804). Alternatively the attachment site may be a channel 807' (FIG. 8C) or a keyed region 807 (FIG. 8A) in the palatal expander body 802 (e.g., the buccal side of the palatal expander) for engaging the attachment connector 805. Alternatively or additionally, the attachment site 809 on the palatal expander may be configured to snap onto the attachment connector 806 (e.g., FIGS. 8E-8H), which may be tapered as it approaches the tooth surface. Any of the attachment connectors/attachment sites shown maybe configured so that multiple attachment connectors 815 couple with one attachment site 813. In some examples, the attachment site and/or attachment connector may be configured to allow adjustment/readjustment of to tighten/loosen the connection. For example, a plurality of attachment connectors 817 (e.g., FIG. 8M) may connected together in a manner that allows the user or patient to select which of the plurality of attachment connectors engage with the attachment site (or sites) 819. Alternatively or additionally the device 821 may include a plurality of attachment sites 822, 822' (e.g., FIG. 8N) that are oriented with slots/slits in different directions so that the two or more attachment connectors 825 can be inserted and allow a torquing or other directional forces (rotational, etc.) to be applied by the device against the teeth. As shown in FIGS. 8A to 8N, extended open hole structures 813, 807 may be present between attachment connectors, and/or the coupling sites may be configured as dual and single hook 803 systems. In coupling attachments in which the coupling region includes a hole and slit may be modified so that the slit is tapered to increase retention. Examples of key and lock systems in different geometries are also shown. As mentioned, the attachment region may be alternatively positioned on the tooth and the attachment connector may be on the appliance (device). Any of these designs may be used to control moments and forces for teeth movement.

Figure 9A:
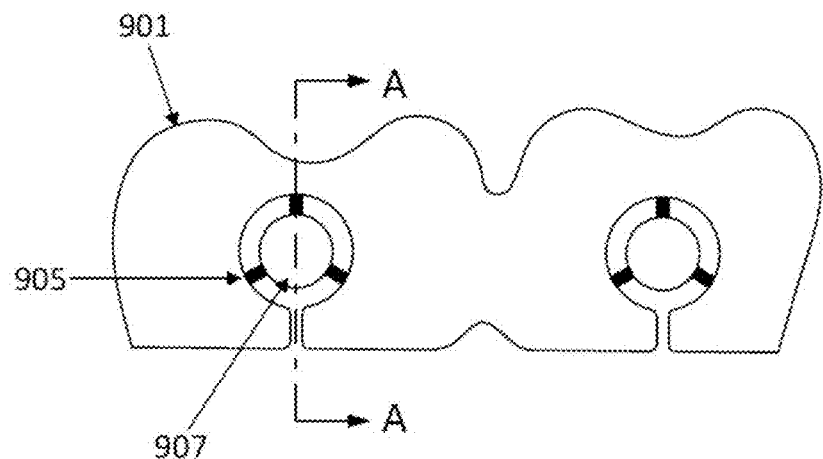
FIGS. 9A and 9B illustrate a portion of a palatal expander including a plurality of openings to connect to attachments on the patient's teeth; in this example the openings of the expander initially include the attachment to be bonded to the patient's teeth, which are connected by one or more tabs that can be disconnected, broken, or removed to leave the tab behind on the patient's tooth. This may be useful for properly attaching the connector attachment to the patient's tooth.
Figure 9B:
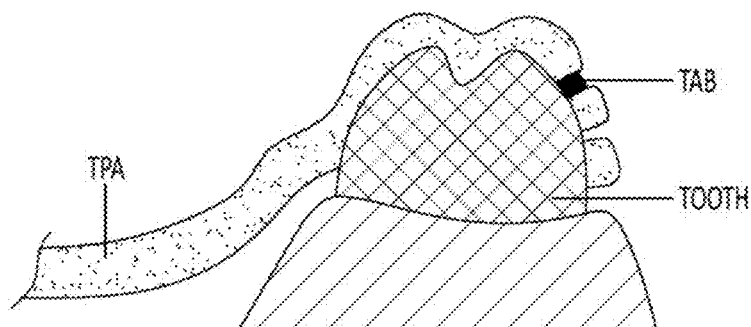
Figure 10:
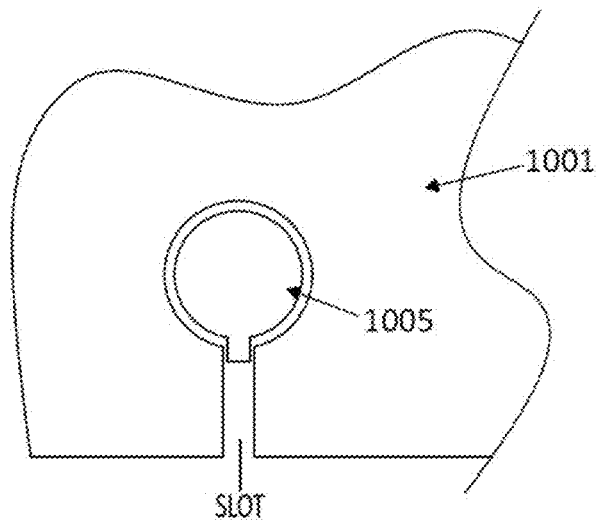
FIG. 10 is another example of an expander including an attachment that can be included as part of the expander (shown here as a separate element held within the opening of the palatal expander) for application to the teeth as a guide or template.

In variations in which the attachment connector (e.g. post) is bonded to the patient's tooth, the connector may be attached using an exemplary expander (the expander maybe provided as a "zero" expander in the sequence, in which the palate is not yet being expanded). This expander may act as a template to position the attachment connectors on the teeth, as illustrated in FIGS. 9A, 9B and 10. In FIG. 9A, the attachment connector(s) are included together with the palatal expander 901 which may be used as the placement vehicle (template). The attachment connector 907 may be printed with the expander (including the attachment region), such that one or more tabs 905 (e.g., removable, frangible, severable, etc. tabs) extend from the attachment region having an opening (hole) feature in the palatal expander 901 to an attachment connector. The tab in this example is a small tabs or sliver of material. The tabs will be cut/removed after bonding the attachment connector 707 to the teeth. The tabs may be made of a dissimilar material than the palatal expander (or of the same material) and/or the attachment connector 907 may be made of the same or a different material as the expander and/or the tabs. The attachment connector may be designed with a custom buccal surface contour to make the buccal fit more precise.

FIG. 10 illustrates another example of an apparatus including an attachment region that is an opening or hole feature in the palatal expander 1001; this example may also act as a bond template for a preformed attachment connector 1005, which in this example is not attached to the expander/template with tabs. In this example, the attachment connector(s) may be fabricated separately (out of another material and/or process, or out of the same material and/or process) but the expander may include a customized connector region (hole feature) that includes a positioning feature to orient the attachment connector 1005 so that the patient's buccal surface contour lines up. The attachment connector may be designed so that the buccal surface contour and positioning feature align for accurate placement.

Palatal Expander Series

A series of palatal expanders may be customized by digitally modeling the patient's oral cavity and automatically, semi-automatically or manually manipulating the digital model to plan the series of palatal expanders to be worn to achieve a desired final configuration of the patient's upper arch at the end of the palatal expansion treatment. In some variations, the final position may be determined as an endpoint for the palatal expansion, and the stages of palatal expanders used to achieve this final configuration may be determined. The stages may be referred to as intermediate positions. A customize expander may be generated for each intermediate position and for the final endpoint (including a maintenance device to be worn for a period of time, e.g., 1 month, 2 months, 3 months, 4 months, 5 months, 6 months, etc.) after expansion of the palate. The methods and apparatuses described herein may be configured to design each expander, including the stiffness and/or shape of the expander (and in particular the palatal region, referred to herein as the IPA or interpalatal arch) by modeling both the orthopedic movement of the arch and the orthodontic movement of teeth in the jaw bone, and applying constraints on the movements of the palate, teeth and/or gingiva in the jaw, including constrains (e.g., limits) on one or more of: the rate of movement of the two sides of the palate, the rate of expansion between the teeth (e.g., molars on opposite side of the patient's upper jaw), an amount of force applied to the patient's oral cavity, a rate of dental movement of the patient's teeth, and a rate of change of an angle between a left and a right portion of the palate. These constraints may be expressed as a limit on an increment of change of these movements. The patient's age may also be used to model or simulate movement of the palate and/or teeth.

In general, palatal expanders customized to a particular patient may be based on manipulation of a digital model of the patient's oral cavity that includes both orthopedic (e.g., palatal expansion) and optionally orthodontic (e.g., tooth movement within the jaw) movements to create a series of expanders.

For example, described herein are methods and apparatuses for designing and fabricating customized palatal expanders (e.g., rapid palatal expanders) based on a digital model. In general, any of these methods may include taking/ receiving a digital model of patient's oral cavity, include the patient's palate surface. For example, a digital scanner may be used to scan the patient's oral cavity (e.g., teeth, gingiva, palate, etc.). Optionally, the digital model may be segmented into tooth, gingiva and palate models. Segmenting may be helpful when separately modeling tooth movement within the jaw (orthodontic movement) and palatal movement (orthopedic movement). Alternatively, orthopedic and orthodontic movements may be modeled together (though even if modeled using separate components, the two may interact so that movement of the jaw may inform movement of the palate, and/or vice versa). The method and apparatus may determine a final position of the palate and/or teeth to be achieved by the series of expanders, including staging orthopedic and orthodontic movement to achieve the final position. This modeling may then be used to design a customized rapid palatal expander for a specific patient. Thus, in any of the methods and apparatuses described herein, the digital model may be used to predict both orthopedic (palate expansion) and orthodontic (dental) movement, and the model may be used to determine a final position setup and to define the movement/velocity of the palatal expansion and/or teeth.

As part of the modeling, the palatal surface being remodeled may be morphed for treatment simulation, prediction and expander design. Accurate morphing of the palate during modeling and simulation may allow the custom expanders (and particularly the palatal regions) to be accurately designed, including providing appropriate or desired spacing from the patient's palate, or in some variations a snug fit against the patient's palate.

The expanders described herein may be rapid palatal expanders. The method and apparatuses for designing these customized rapid palatal expanders may include controlling force and stiffness based on treatment stage, age, arch shape and other information.

FIG. 11 illustrates an exemplary method of designing and/or forming a series of customized palatal expanders. In FIG. 11, the method, or an apparatus (e.g., a device or system, including software, hardware and/or firmware) performing this method, receives a digital model of the patient's oral cavity 1101. This method and/or apparatus may be used to automatically or semi-automatically design one or more, e.g., a series, of palatal expanders which may be fabricated by any of the techniques described herein and worn by the patient. When configured to operate semi-automatically the apparatus may operate interactively with a user, such as a dental technician, physician, dentist, orthodontist, etc., so that the at least some of the design parameters and decisions may be guided by the user, who may be provided immediate feedback, including visual feedback and modeled feedback on the forces acting on the simulated expander and patient's dentation.

In general any of the methods and apparatuses configured to perform these methods described herein may be performed by a dedicated apparatus, which may include digital inputs (digital file inputs and user inputs, such as keyboards, etc.), one or more processors, at least one visual output (e.g., screen, printer, etc.) and one or more digital outputs, including a digital file output for use in fabrication, such as direct (e.g., 3D printing) fabrication. Alternatively or additionally, the method and an apparatus performing the method may be performed by a general-purpose device executing the specific and/or specifically adapted control logic. Thus, in any of these variations, the apparatus may be configured as control logic (e.g., software, firmware, etc.) that causes a processor (microprocessor, etc.) to perform the various functions recited. Any of the apparatuses described herein may comprise non-transitory computer-readable storage medium storing a set of instructions (control logic) capable of being executed by a processor, that when executed by the processor causes the processor to perform operations ultimately forming one or more customized expanders. The control logic may be specifically adapted to operate on a processor of a local or remote computer (laptop, desktop, etc.), remote server, smartphone, pad, wearable computer (smartwatch, etc.).

Returning to FIG. 11, the method or apparatus configured to perform this method receives the digital model of the patient's oral cavity 1101. This digital model may be provided by one or more sources, including in particular digital scanning systems, including intraoral scanners, such as those described in U.S. Pat. No. 7,724,378, US 2016/0064898, U.S. Pat. No. 8,948,482, US 2016/0051345, US 20160003610, U.S. Pat. No. 7,698,068, US 20160163115, U.S. Pat. No. 9,192,305 and US 2015/0320320, which may be used to determine topographical representations of a subject's teeth and/or gingiva and/or palate. The patient's mouth may be directly or indirectly scanned (e.g., scanning a model or impression of the patient's mouth). Other scanning systems may include scanning trays or the like (see, e.g., U.S. Pat. No. 8,520,925). The digital model may be multiple digital models of different portions or regions, for example, separately including the teeth, gingiva and palate, or separately including different regions of all three that may be combined into a single digital image of the entire oral cavity or relevant part thereof. In any of these apparatuses and methods, both the upper and lower jaws may be digitally scanned and provided. In particular, the teeth of the lower jaw may be included, as well as the teeth, gingiva and palate of the upper jaw.

Optionally, the digital model may be segmented 1103 into separate tooth/teeth, and/or gingiva and/or palate models that together form a digital representation of the patient's oral cavity, including the palatal surfaced. This digital representation can then be used to model the orthopedic movement of the palatal expansion and the orthodontic movement of the teeth. The user can provide the targeted final position and/or use or adjust the model to predict orthodontic movement of the teeth. The digital model may adjust from the initial position to a final position in which the palate is expanded 1105. The digital model may be morphed to reflect an orthopedic expansion of the patient's midline suture and an orthodontic movement of the teeth within the patient's jaw 1107. In general, when modeling the incremental palatal expansion to stage the palatal expansion, the movement of the palate (e.g., the right side of the palate and the left side of the palate, on either side of the midline suture) may be based or approximated from anatomical constrains. For example, the movement of the right and left sides of the palate may be rotational moved relative to an expansion axis 1107 that extends in an axis away from the patient's face, at an angle (e.g., of between 5 degrees and 85 degrees, e.g., between 5 degrees and degrees, between 10 degrees and 70 degrees, etc.) relative to an xy plane through the midpoint of the teeth in the upper arch, e.g., in a mid-plane of the patient's face extending between the patient's nose and a back of the patient's upper jaw. Other method constraining the movement of the palate and/or jaws and/or teeth may be applied instead or in addition to rotation about an expansion axis.

In FIG. 11, once the final position of the palatal expansion is determined automatically, manually or semi-automatically, the sequence of palatal expanders needed to accomplish this final position may be generated using the digital model. Any number of steps or stages, each corresponding a removable palatal expander that may be applied and/or removed by the patient or more likely the patient's caregiver (as the patients may typically be children between the ages of 7 and 12 years old), may be calculated. For example, the method or an apparatus configured to perform the method may generate a plurality of intermediate positions of upper arch, and from this model a palatal expander model corresponding to each intermediate and the final position 1109. For example, the method or apparatus may determine each stage (each intermediate position) based on a stiffness of the palatal expander and a limit on an one or more of the rate of movement of the patient's teeth when the palatal expander corresponding to that stage is worn, and/or a limit on the force(s) applied by the palatal expander to the patient's oral cavity or regions of the oral cavity. For example the method or apparatus may determine intermediate positions based on an increment of change in at least one of the patient's palate and teeth, where the increment of change is one or more of: a rate of expansion between the molars, an amount of force applied to the patient's oral cavity, a rate of dental movement of the patient's teeth, and/or an angle between a left and a right portion of the palate 1111.

Figure 11A:
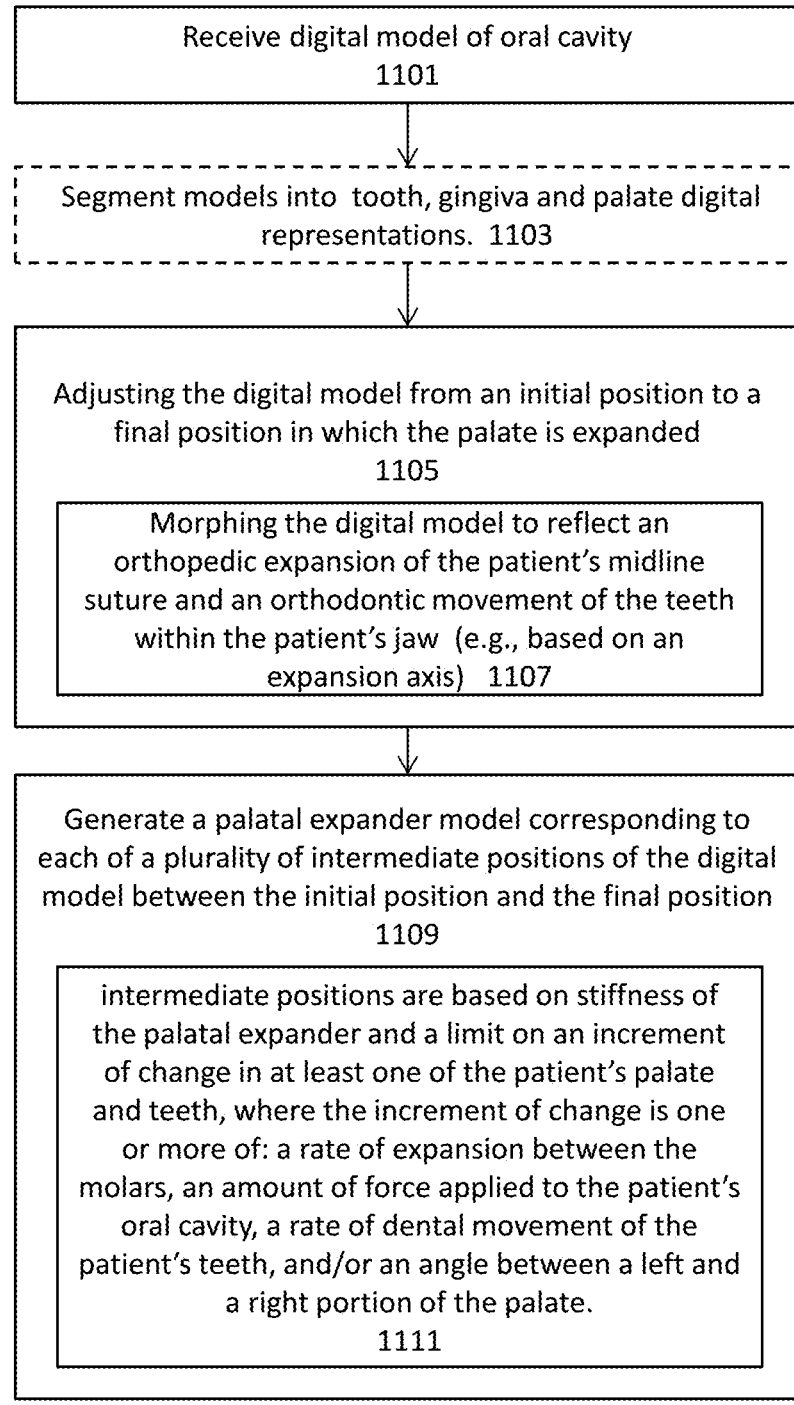
FIG. 11A illustrates one example of a method of forming a series of customized palatal expanders as described herein.
Figure 11B:
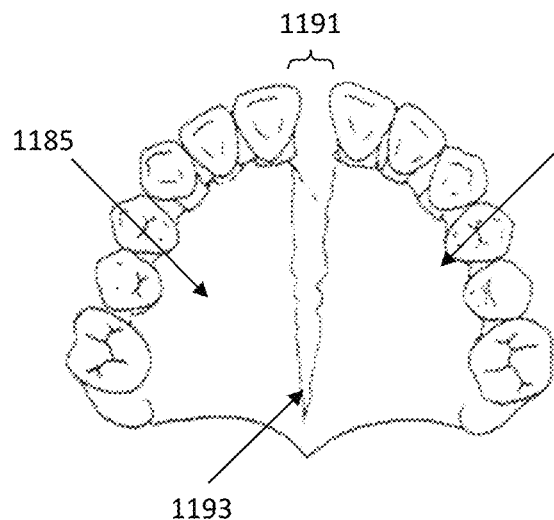
FIGS. 11B and 11C illustrate translation and tipping of a typical dental arch during treatment to expand the palate.
Figure 11C:
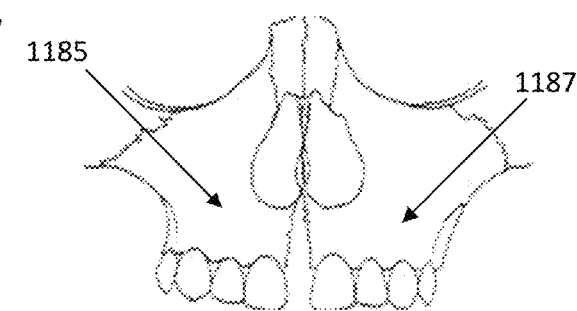
Figure 11D:
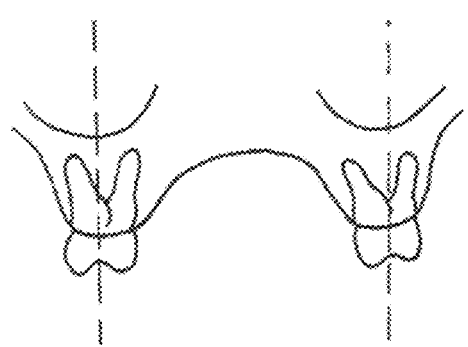
FIGS. 11D and 11E illustrate tipping of the teeth during palatal expansion.
Figure 11E:
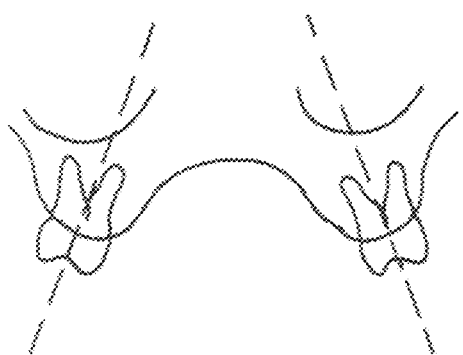

In any of these methods and apparatuses, the final and incremental positons may be modeled to include both the translational and rotational (e.g., tipping) movement of the left and right maxillary halves. This is illustrated in FIGS. 11B and 11C. In general, palatal expansion with the apparatuses and methods described herein does not uniformly separate the right 1185 and left 1187 palatal regions. For example left anterior portion (front) of the palate will expand more than the more posterior region, resulting in a triangular separation of the mid-palatal suture, as shown in FIG. 11B. In addition, as will be described in greater detail below and shown in FIG. 11C, the right 1185 and left 1187 maxillary halves of the palate will tip about an axis that extends away from the patient's face at an angle (e.g., of between 5 degrees and 85 degrees, e.g., between 5 degrees and 50 degrees, between 10 degrees and 70 degrees, etc.) relative to an xy plane through the midpoint of the teeth in the upper arch. Thus in modeling the intermediate and final position of the palate during the expansion described herein, these methods and apparatuses may model both the translational movement (e.g., in the xy plane) as well as tipping (e.g., rotation) about this axis. Specifically, the methods and apparatuses described herein may model and account for the more anterior separation of the palate 1191 (compared to more posterior regions 1193) and tipping in an axis extending at an angle to the plane of the upper teeth. In addition, any of these methods and apparatus may also account for tipping of the teeth, as shown in FIGS. 11D and 11E. Movement of the palate by applying forces may result in tipping of the teeth, both due to tipping of the arch (e.g., FIG. 11C) during expansion, but also due to force applied by the palatal expanders on the teeth. In FIG. 11E the teeth are tipped outwardly compared to the original position shown in FIG. 11D.

Figure 11F:
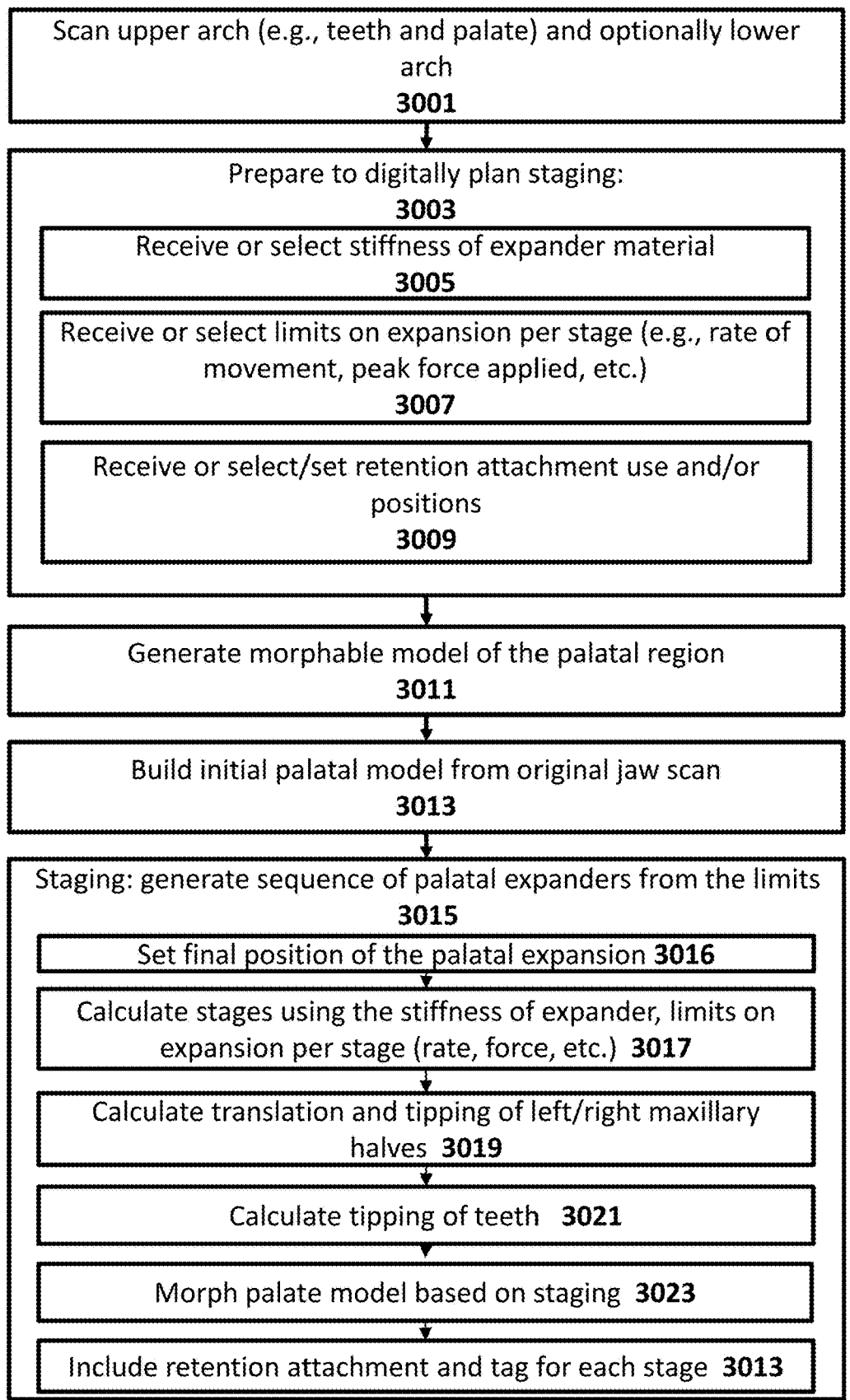
FIG. 11F is another example of a method of forming a series of customized palatal expanders.

FIG. 11F illustrates another example of a method of generating a series of palatal expanders to treat a patient. This method may be performed by a processor (on a computer, tablet, smartphone, etc.) that is configured to execute these steps and may also control fabrication of the resulting series of palatal expanders. All of the palatal expanders may be designed and fabricated for delivery to be worn by the patient together. As described above a digital model of the patient's teeth may be provided 3001 to the processor. The method (or a processor configured to perform the method) may then prepare for planning the stages of the palatal expanders 3003. A user interface may interactively allow control of the design of the series of palatal expanders. For example, a user interface may allow the user to select the material from which the palatal expander is going to be formed, and therefore the material properties of the apparatus 3005. Alternatively or additionally, this information may be recalled as a default (e.g., from a memory accessible by the processor). Similarly, the user may input or select what limits on expansion are to be used in staging the palatal expander: rate of expansion, and/or peak or maximum force to be applied, etc. 3007. Alternatively or additionally, this information may be recalled as a default (e.g., from a memory accessible by the processor). Optionally, the user interface may also allow the user to select and/or position attachments on the patient's teeth 3009. Alternatively or additionally, this information may be recalled as a default (e.g., from a memory accessible by the processor).

A morphable model of the patient's teeth may then be generated from the digital model of the patient's palate. This is described in greater detail below. The morphable palatal model may provide a more accurate approximation of the shape of the palate during the course of the palatal expansion procedure. During treatment, the gingiva and palatal surface are moved and change shape. The morphable palatal model may be used during treatment to predict the shape of the palate over the course of the treatment. This may be particularly helpful when designing the palatal expanders so that there is clearance (e.g., space) between the patient's palate and the top surface of the palatal expander in each stage. Thus, the method may leave clearance between the palate and the apparatus sufficient to prevent contact while limiting the space so that food does not get trapped between the appliance and the palatal surface.

Returning to the method described in FIG. 11F, the method may optionally include building an initial palatal model from the original scan of the jaw (e.g., upper arch) 3013. The palatal model may include a model of the palate, gingiva and may also include the positions of the teeth. The initial position may then be modified by the staging steps 3015, during which a sequence of palatal expanders are generated using the defined parameters or limits. For example, the final position may be determined (at this step or earlier) 3016. As discussed above, the final position may be automatically generated by the software, or manually (or semi-automatically, e.g., assisted by the software) generated. For example the processor may provide a user-interface that displays the digital model of the patient's dental arch (e.g., teeth, gingiva and palate) and provides tools for a dental practitioner or technician to manipulate the digital model to create the proposed final position of the expanded palate. The processor may automatically adjust the rotation of the arch, as described herein, to create the final proposed position. Alternatively, the processor may receive a final position of the palate.

Figure 40A:
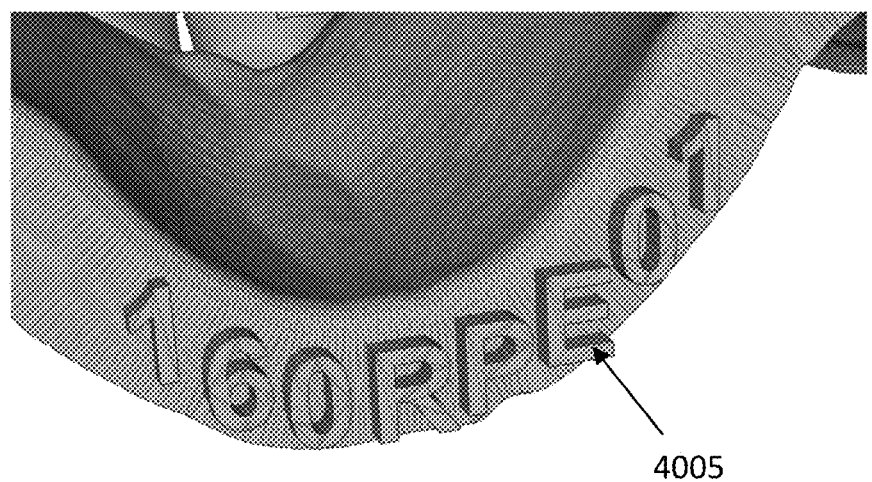
FIG. 40A shows one example of a tag on a posterior-facing side (edge) of a palatal expander.
Figure 40B:
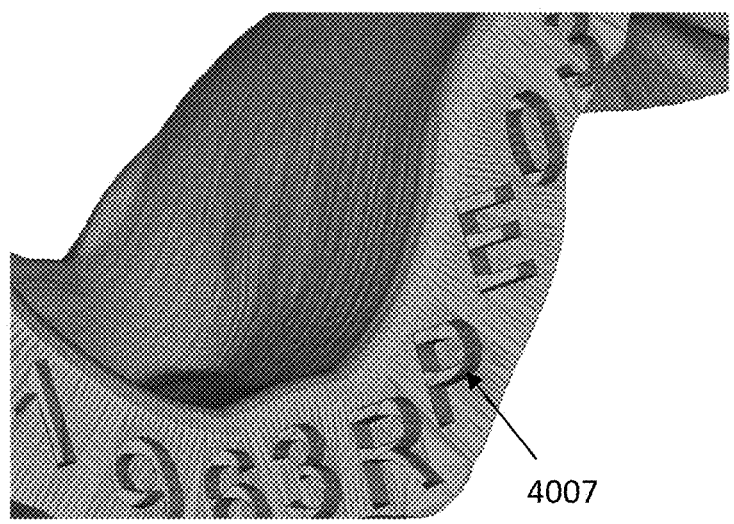
FIG. 40B is another example of a tag on a posterior-facing side (edge) of a palatal expander.

The processor may then use the initial position and the proposed final position and may apply the constraints defined to the processor to generate the sequential stages corresponding to individual palatal expanders. For example, for each stage, the processor may set the palatal expander configuration (e.g., the position of the tooth engagement regions that attach over the molars of the right and left maxillary halves, and the size and thickness of the palatal region, etc.) to generate a maximum amount of force and/or movement (e.g., 0.25 mm, etc.) at each stage based on the material properties (e.g., stiffness) of the palatal expander 3017, while translation and rotating the left and right maxillary halves 3019 about an expansion axis. The processor may also determine the tipping of patient's teeth 3021 so that the palatal expander may properly fit and seat over the teeth at each stage. For each stage, the morphable model may be morphed to allow accurate prediction of the palate. The morphable model may be morphed using any appropriate morphing algorithm, including but not limited to a thin plate spine procedure. The positions of the teeth (e.g., tipping) may be determined as well (e.g., based on tooth crown and/or centers to determine tooth movement. The suture opening may be modeled in the morphable model by, e.g., including a plurality of suture points defining the suture opening. Thus, for each stage, the morphable model may be morphed based on the staging 3023. In addition, as will be described in greater detail herein, the processor may include any retention attachments, and may also tag each stage 3013. Once the entire sequence is generated, the processor may then fabricate, or transmit the electronic file(s) describing each stage, for fabrication. Any appropriate fabrication technique may be used, including 3D printing. The sequence may then be provided to the patient for use. FIGS. 40A and 40B also illustrate examples of tags (e.g., PID tags) that may be directly formed into each palatal expander in a series of palatal expanders. As mentioned and described, the tag may be an alphanumeric or any other uniquely identifying tag, and may be formed into the material of the expander. In FIG. 40A, the tag is a PID string that identifies the stage and (e.g., last two digits) and/or a patient or treatment identifier. In FIG. 40A the tag 4005 is embossed (projects out of) the posterior end of the palatal expander. In FIG. 40B the tag 4007 is engraved (e.g., projects into) the posterior end of the palatal expander.

Figure 12:
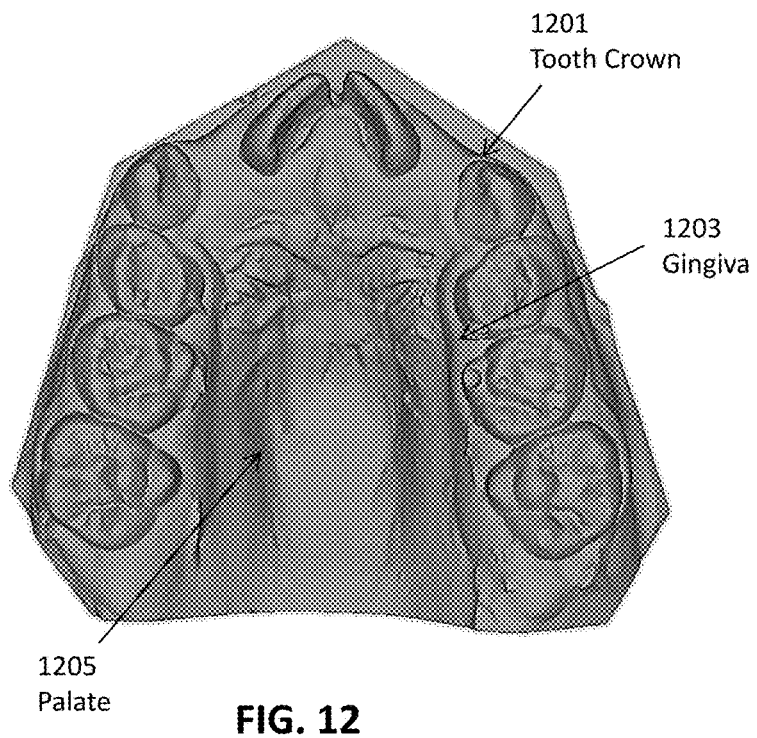
FIG. 12 shows an example of a rendering of a bottom view of a digital model of a patient's oral cavity.

A digital mode of the patient's oral cavity may be acquired from any appropriate source, such as an intraoral scanner. When acquiring a digital model of patient's oral cavity, the digital model may include upper and lower jaws, including tooth crown, gingiva and maxillary palatal surfaces. FIG. 12 illustrates an example of a rendering of a bottom view of a digital model of a patient's oral cavity (including just the upper jaw; in other variations the upper and lower jaw may be included). In FIG. 12, the model includes the tooth (tooth crown) 1201, the gingiva 1203 and the palate 1205 of the patient, showing the initial position. The digital model captures the patient's oral cavity. As mentioned, it may include both upper and low jaws; for the maxillary jaw, crown, gingiva and palate surface may be included. In FIG. 12, the ridges, channels and other non-smooth structures on the patient's palate are visible.

Figure 13A:
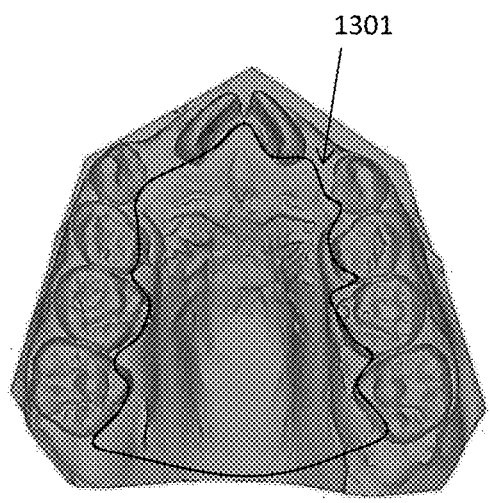

Optionally, the digital model of the patient's oral cavity may be segmented into two or more segments. For example, the cavity may be segmented into three portions, including the teeth, gingiva and palate. All of the teeth may be included in the teeth portion or only some (e.g., the back four molars) may be included. FIGS. 13A-13D illustrates a method of segmenting the digital model of the patient's oral cavity. In FIG. 13A, the digital model is divided up by a lingual gingival curve 1301, while in FIG. 13C, the three segmented regions are shown, including the tooth model 1305, the solid palatal model 1307 and the gingiva model 1309.

The tooth and gingival models may be built using a process that determines the boundary between these two regions; the palate model may be built by getting the gingival lines of the teeth, and linking them to create the "lingual gingival curve" (see FIG. 13A), selecting only shapes/vertices inside of the lingual gingival curve, and rebuilding a solid palate model (FIG. 13C) or a surface (FIG. 13D).

The digital model (or segmented digital model) may then be manipulated either automatically or manually to set a final expanded configuration of the palate and/or teeth. The digital model may allow manipulation of the components (including the right and left sides of the palate, about one or more palatal sutures, such as the mid-palatal suture (e.g., midline suture, intermaxilary suture, etc.), transverse suture (interpalatine suture, transverse palatine suture, etc.), pre-maxiliary suture, etc., and in particular the mid-palatal suture. The manipulation may be constrained, so that when the digital model is moved to expand the palate, the movements are based on one or more physiological constraints guiding the relative movements of the different palatal regions. In some variations, a rapid palatal expansion model to determine expansion of the palate, including determining a final (expanded) position, may be based on rotation about an expansion axis. Thus, the digital model may be constrained to simulate and predict rapid palatal expansion treatment outcome, with both orthopedic and dental movement, which includes orthopedic expansion (e.g., the expansion of the midline suture, and inclination changes of the left and right maxillary halves) and dental movement (e.g., dental movement of tooth inside the bone). The manipulation of the model can be constrained obtained the anatomy of jaw and bone, and/or by measurement and data analysis of real treatment outcome and/or published literature.

As mentioned above, in setting the final position and/or the intermediate positions (stages), the left and right maxillary halves may be moved so that the left and right maxillary halves (including teeth, gingiva and palatal regions) are tipped about an expansion axis that projects out from patient's head anteriorly, at an angle to the plane of the teeth. The plane may be the crown center plane of all of the upper teeth, for example, with the y-axis extending down the midline of the paired crown centers. Expansion of the palate (e.g., expansion between the left and right maxillary halves) may result in movement of the teeth in the x direction. This movement may be constrained by the methods and apparatuses described herein so that the movement is coordinated about the expansion axis, resulting in an angled (e.g.

v-shaped) separation between the left and right maxillary halves, with rotation (tipping) in opposite directions around the expansion axis.

One example of such a constraint and method of modeling movement of the palate is the "expansion axis" mentioned above, and illustrated in FIGS. 14A-18. In any of these methods and apparatuses, the left and right maxillary jaw and palatal surface may be modeled as two moving parts. When determining the orthopedic and orthodontic movements of the patient's oral cavity from the digital model, each part can be rotated around one expansion axis, forming an expansion angle. The expansion angle is the angle between the left and right maxillary halves (including the left and right palatal regions, respectively). The expansion axis is typically located above the roof of the upper jaw, projecting anteriorly. For example, the expansion axis may be located in the middle plane of jaw/face, and roughly pass a point near nose, and at the back of upper jaw.

FIGS. 14A-14C illustrate palatal expansion about an expansion axis, forming an expansion angle. FIG. 14A shows the separation of the left and right palatal regions when rotating about an expansion axis 1405 (shown in FIG. 14C) forming an expansion angle 1403. The movement of formerly central (along the midline suture) points based on the rotation angle is shown. FIG. 14A shows a view up to the upper jaw, while FIG. 14B shows a front view of the same digital representation of the jaw. FIG. 14C shows a perspective view with the expansion axis 1405 labeled.

Figure 13B:
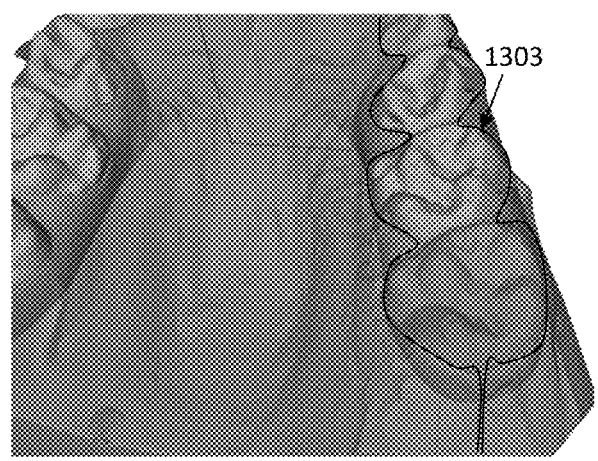
Figure 14D:
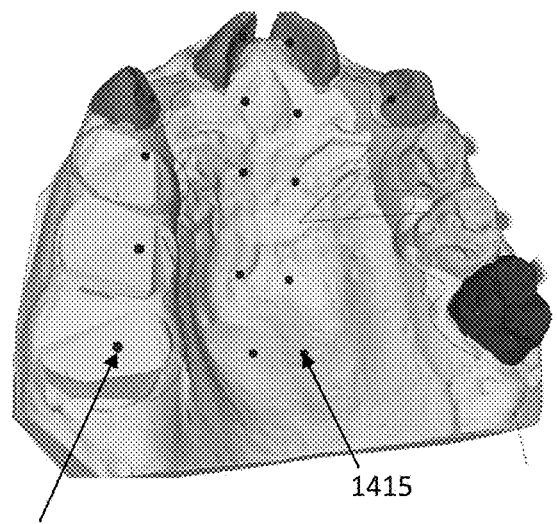

In modeling the final and intermediate positions for palatal expansion, the digital model of the patient's teeth that includes the palate (which may be referred to herein as a morphable palatal model) may be generated and manipulated. For example, the morphable palatal model may be formed by segmenting and removing the crown portion of the teeth (as described above). The teeth are rigid bodies that are not typically morphable. Lingual and buccal split curves from the gingival lines of the teeth may be formed (see, e.g., FIG. 13A, showing the lingual gingival curve 1301; a similar buccal curve may be determined on the buccal side, as shown in FIG. 13B). The initial palatal model may be created by mapping the three-dimensional vertex into a two-dimensional point. A mesh may be created by triangulation from the 2D projections taken from the 3D dataset, and mapped back to create a full 3D model that may be manipulated, including the palatal region and teeth. This 3D model may be morphed using any appropriate technique, including, e.g., Thin Plane Spline techniques. Morphing may be regulated by control points; for example control points may be placed on the teeth (crowns and/or centers) to control tooth movement and/or suture points to control the suture opening. This is described below in greater detail in reference to FIGS. 21A-21C. Movement of these control points may be regulated by clinical constraints, as mentioned above. For example, the direction and extent of movement may be limited or modified based on the relative location within the palate. FIGS. 14A, 14B and 14D illustrate suture control points 1415 and crown control points 1417 that may be used when morphing the model. In some variations, morphing the model at the final and intermediate stages may include getting the control point(s) for each stage, morphing each vertex in the full palatal model (e.g., a digital model that does not include the crowns) then using the morphed model to build the full model (new shape including the crowns) and assign it to that stage. A palatal expander may then be built from this full stage. The steps for generating the palatal expander are described in greater detail below in reference to FIGS. 30-33.

Figure 15A:
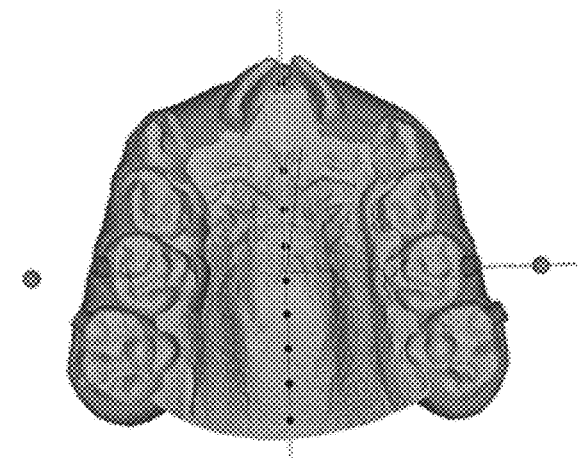
FIGS. 15A and 15B show another view of a simulated expansion model of the upper palate.
Figure 15B:
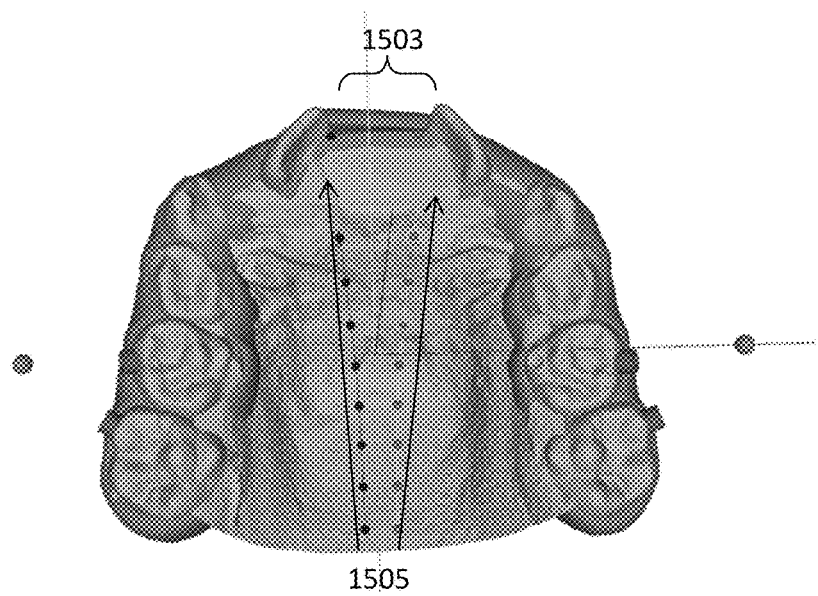
Figure 16A:
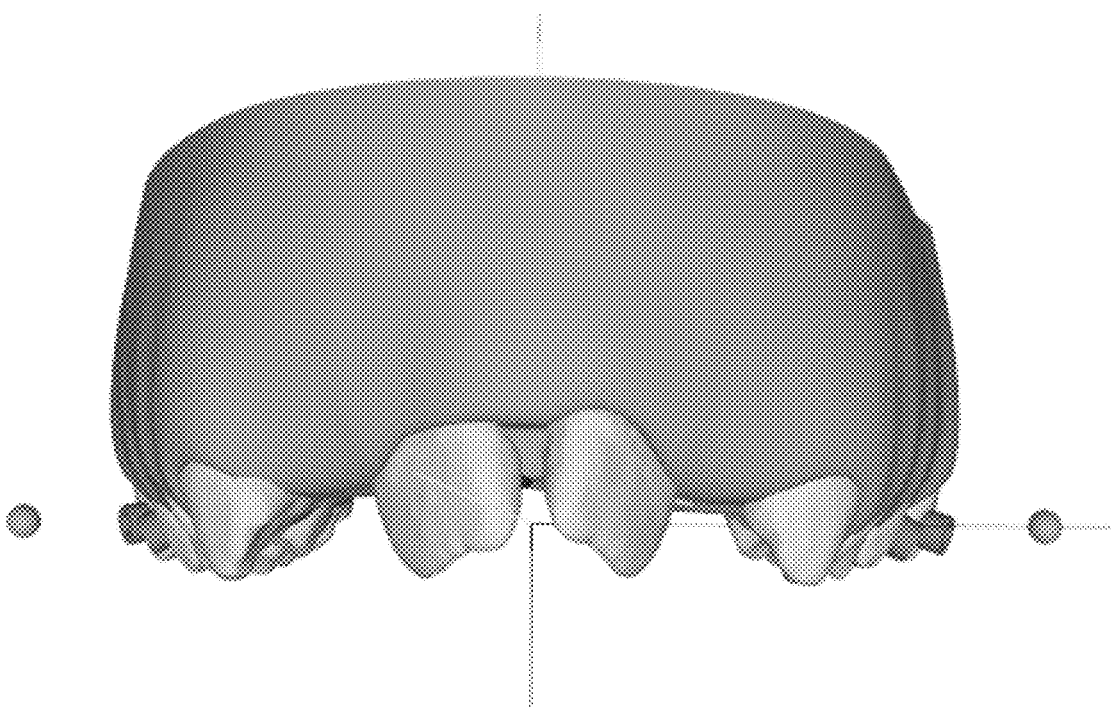
FIGS. 16A and 16B show frontal views of a simulated expansion model of the upper jaw.
Figure 16B:
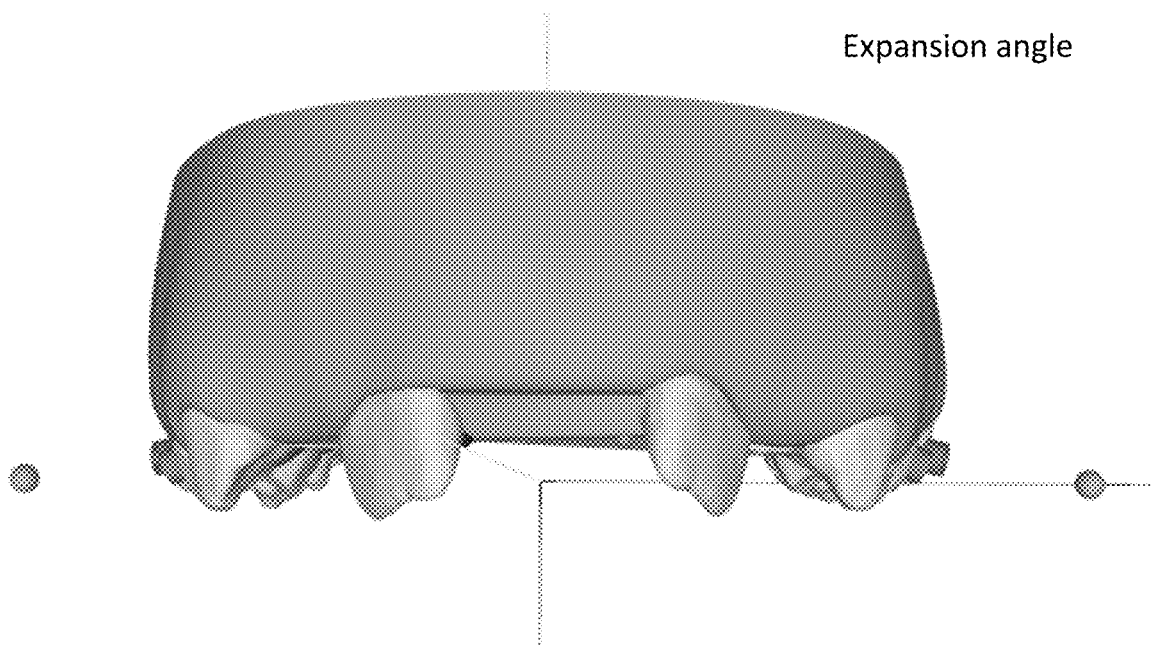

FIGS. 15A and 15B show another view of a simulated expansion model of the upper palate. The original (starting) digital model of the upper jaw is shown in FIG. 15A; in FIG. 15B the left and rights palatal regions (and associated/connected jaw/tooth regions) have been rotated about the expansion axis, resulting in expansions and opening of the midline suture 1503 about an expansion angle 1505. FIGS. 16A and 16B show frontal views of before (FIG. 16A) and after (FIG. 16B) rotation of the left and right maxillary halves about the expansion axis in digital model.

Figure 17A:
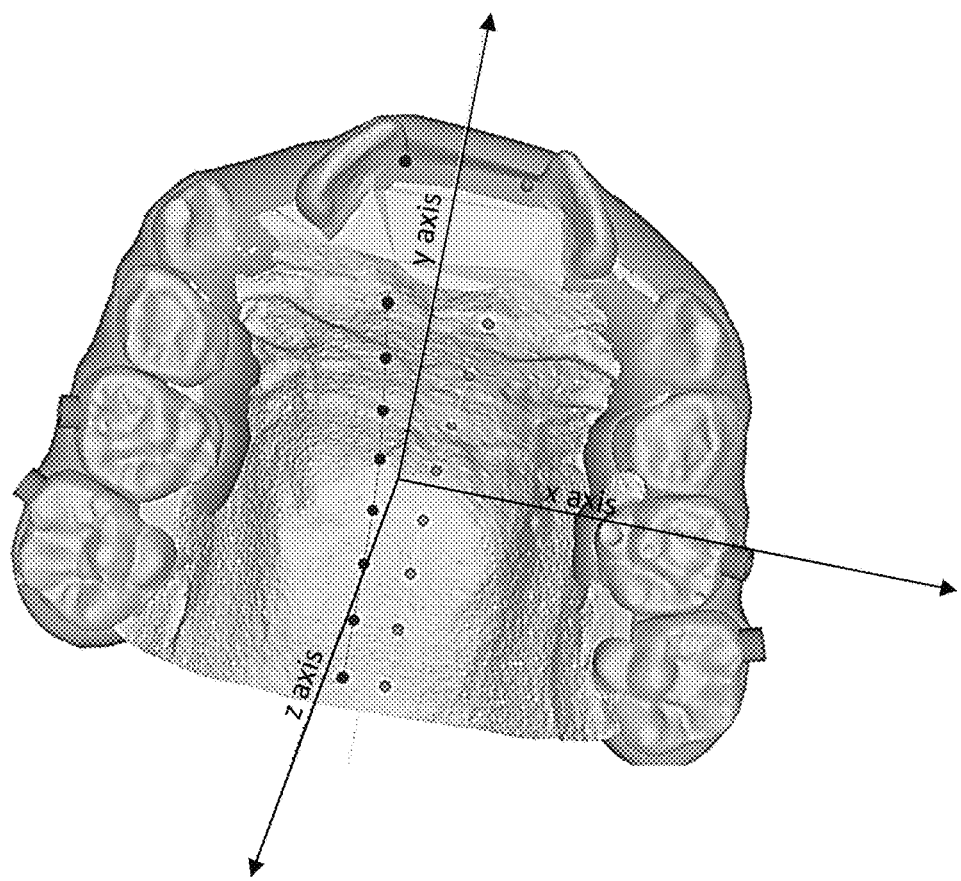
FIGS. 17A and 17B illustrate identification of axes (x, y, z) that may be used to determine an expansion axis.
Figure 17B:
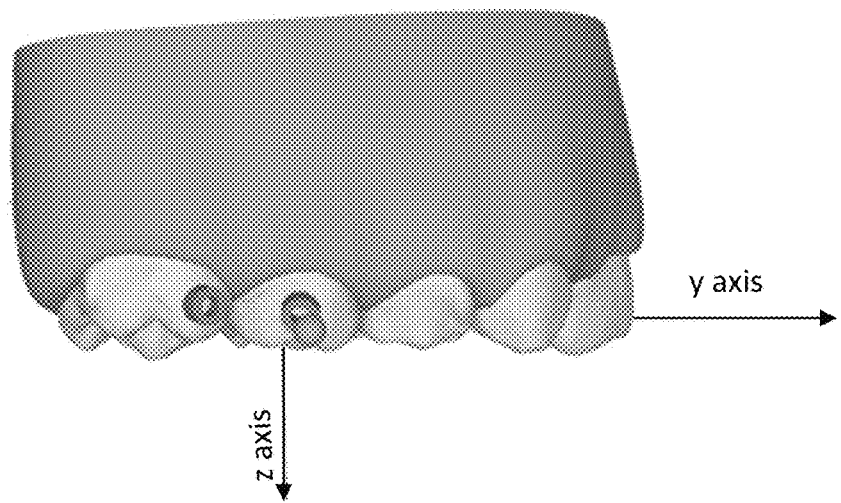
Figure 18:
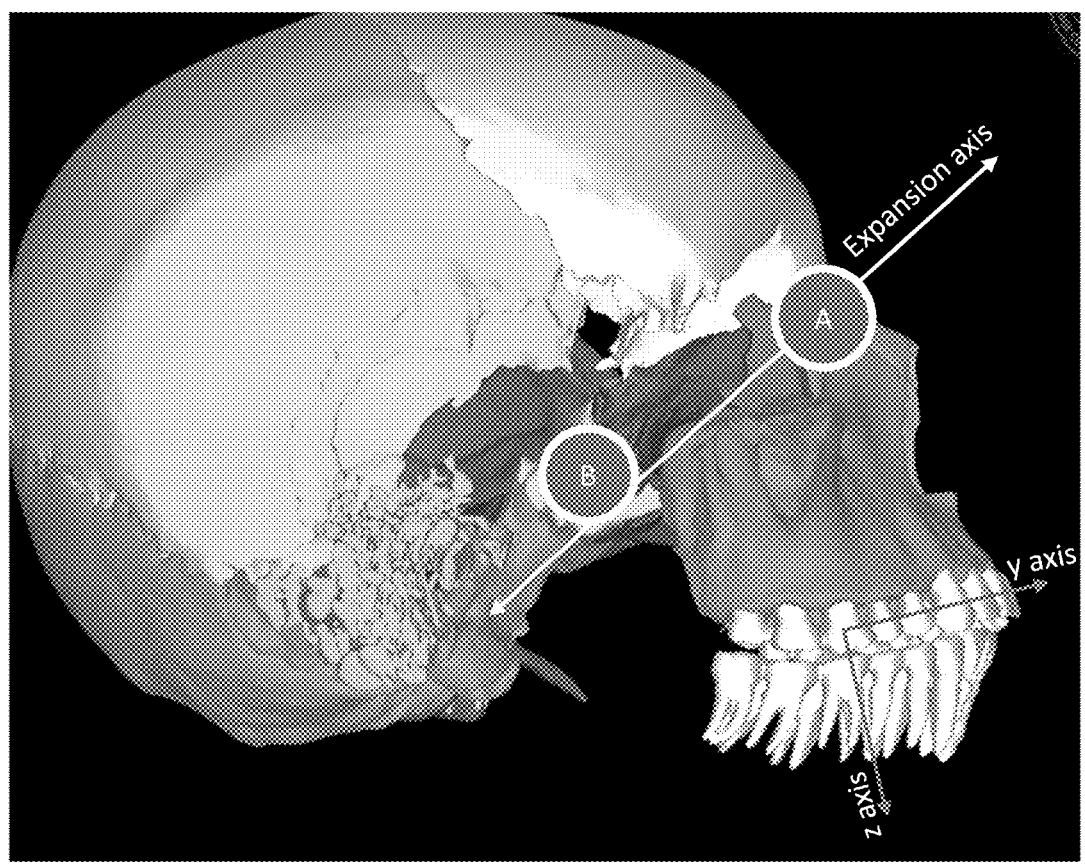
FIG. 18 illustrates an exemplary method of determining an expansion axis.

The expansion axis may be determined for a particular patient based on landmarks from the oral cavity (e.g., using digital model) and/or additional physiological markings from the patient. For example, the expansion axis may be determined for a particular patient (or a class of patients) by the anatomy of jaw and bone. As illustrated in FIGS. 17A and 17B, the expansion axis may be determined by identifying a jaw basis, where the x axis passes the left and right molars, y is the middle plane of all teeth and z axis is the occlusal plane. The expansion axis may be located at a middle plane (YZ plane of the jaw basis), and may be determined by the anatomy of the bone. As shown in FIG. 18, it may pass point A, where the maxillary bone joints with front bone, and point B, where maxillary bone joints with ethmoid bone. The expansion axis may be estimated from an average angle (e.g., between about 5 degrees 70 degrees, between about 5 degrees and 60 degrees, between about 5 degrees and 50 degrees, between about 5 degrees and 45 degrees, between about 5 degrees and 40 degrees, between about 10 degrees and degrees, between about 10 degrees and 60 degrees, between about 10 degrees and 50 degrees, between about 10 degrees and 40 degrees, between about 10 degrees and 45 degrees, etc.) relative to the xy plane.

Another way to determine a patient's expansion axis is by an analysis of treatment scans from the patient (including before/after treatment 3D scans). For example, the expansion axis may be determined by scanning a before treatment geometry of a patient's maxillary jaw, include teeth, gingiva and palate surface, segmenting the upper jaw into left and right maxillary portion models, both with crown, gingiva and palate, scanning after treatment of rapid palatal expansion, matching the before treatment left/right portion model with after treatment scan, to determine the transformation between left and right, and then finding the rotation axis of the transformation between left and right. Thus, an initial (even small) movement of the palate may provide sufficient information to isolate a patient's expansion axis from clinical data. Alternatively, scans taken over time (e.g., over a 3 month, 6 month, 9 month, 12 month, etc.) period may similarly provide information sufficient to determine the patient's expansion axis.

In general, there may be relatively little dental movement of teeth by rapid palatal expansion, typically because of the short treatment time (e.g., 2 weeks). However, when the expansion speed is slowed (e.g., to 1 month or more), there may still be dental movement. In particular, when the expander is rigid and stronger, the root of tooth may be tipped buccally and straight. Anterior teeth, like canine and incisors, may be tipped back to center because of the force from the face muscles. This may reduce the gap (diastema) caused by the expander. As mentioned above, the dental movement may also be included in the expansion model and final position setup. For example, left and right teeth may be expanded by the expansion axis and expansion angle as described above. The distance of movement between molars may be measured (e.g., 8 mm), and based on the expansion speed (e.g., 0.5 mm/day, 0.4 mm/day, 0.3 mm/day, 0.25 mm/day, 0.2 mm/day, etc.), the total time can be estimated, for example, 16 days or 32 days. The maximum total root tipping distance can then be determined and/or limited (e.g., mm for 16 days or 0.5 mm for 32 days, etc.).

For example, a method for determining a series of rapid expanders may include taking the prescription from the user (e.g., orthodontics), for example, for 10 mm expansion, and adjusting the expansion model to meet the requirement. The expansion model may be adjusted, for example, by adjust the expansion angle, so that the expansion between molars meets the prescription. Then estimating the treatment time may be determined by the speed of expansion, for example, 16 days or 32 days. Minor adjustments to the dental movement may be determined to help straighten the teeth, so the root movement may be limited, for example to between about mm or 1.0 mm. For anterior teeth, the method or apparatus may predict the dental movement. For example, the diastema between central incisor may be closed if the expansion speed is slow (e.g., 0.25 mm/day and total 32 days); if it's rapid expansion (e.g., 0.5 mm/day), the diastema may still exist. The method or apparatus may provide a prediction and setup of the final position of the palatal and/or teeth after an appropriate "retention" period (3 month or more), where more dental movement can be achieved, and anterior diastema will be closed.

Figure 19A:
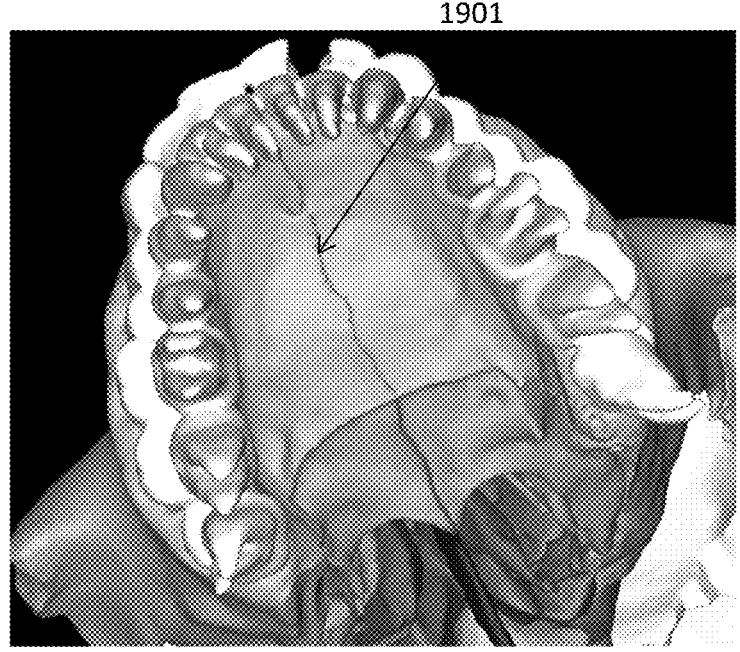

In general, staging of the orthopedic and dental movement may be determined once the final configuration (expansion) has been determined, and may be based on stiffness of the palatal expander and/or suture expansion speed. For example, after the final position is determined, the tooth/jaw movement from initial position can be staged into a series of intermediate positions for which expanders can be determined and made. Because there are both orthopedic and orthodontic tooth movements, several velocity limits may be applied when staging, to make the treatment safe and stable. For example, the speed of molar crown expansion may be limited (e.g., for example about 0.25 mm/day (or stage), e.g., about 0.1 mm/day, about mm/day, about 0.20 mm/day, about 0.3 mm day, about 0.35 mm/day, etc., between about mm/day and about 0.5 mm/day, between about 0.2 mm/day and about 4 mm/day, etc.). Any of the "per day" rates described herein may refer to "per stage". Alternatively or additionally, the opening speed of midline suture, which can be measure by the maximum expansion distance of the midline at each stage, may be limited, for example to about 0.25 mm/day (e.g., about 0.1 mm/day, about 0.15 mm/day, about 0.20 mm/day, about 0.3 mm day, about 0.35 mm/day, etc., between about 0.1 mm/day and about 0.35 mm/day, between about 0.15 and about 0.30 mm/day, etc.). Alternatively or additionally, the change in angle change between the left and right palatal regions may be limited, for example to about 1 degree/day (e.g., about 0.3 degrees/day, 0.4 degrees/day, 0.5 degrees/day, 0.6 degrees/day, 0.7 degrees/day, 0.8 degrees/day, 0.9 degrees/day, 1.1 degrees/day, 1.2 degrees/day, 1.3 degrees/day, 1.4 degrees/day, 1.5 degrees/day, 1.6 degrees/day, 1.7 degrees/day, 1.8 degrees/day, 1.9 degrees/day, 2.0 degrees/day, 2.2 degrees/day, etc., between about 0.05 degrees/day and 1.2 degrees/day, etc.). The speed of dental movement of the teeth may be limited, for example to less than 0.5 mm/2 weeks (e.g., 0.030 mm/day, 0.025 mm/day, 0.015 mm/day, 0.010 mm/day, 0.005 mm/day, mm/day, 0.045 mm/day, 0.050 mm/day, between 0.001 and 0.050 mm/day, between about mm/day and 0.040 mm/day, etc.). FIGS. 19A and 19B illustrate the midline suture 1901 and the maximum expansion of the midline suture 1905.

In determining the final and any incremental positions of the patient's palate, the expanded region of the palate may be estimated by morphing the palatal region. This morphing may be performed as accurately as possible, both to provide a predictive model that may assist in estimating the impact (s) of the palate and overall shape of the patient's oral cavity, but also in designing accurate and expanders. For example, either during and/or after the final position and staging (intermediate positions) are completed, the palatal surface may be morphed to match the expansion. This morphed palatal surface may be used for simulation and visualization of the change of palate, so user (e.g., doctor) and/or patient (including patient's guardian) may know what to expect after treatment. As mentioned, the morphed palatal surface may also be used to design the rapid palatal expander device for each stage. In some variations the palatal expander may be configured so that it sits close to, but does not touch the palate, which may prevent sores, discomfort and/or trapping food between the palate and the expander, yet may retain sufficient room for tongue.

In general, the digital model of the patient's oral cavity may be manipulated in any appropriate manner when designing the expanders or otherwise planning a treatment including expansion. For example, separating the two halves of the palate may be performed, so that each half may be moved by following an expansion model. This is illustrated, for example, in FIGS. and 20B, which show a change of palatal surface after expansion (from FIG. 20A before expansion to FIG. 20B, after expansion). However, by this method, there is gap between left and right halves 2003. One method of filling this gap (morphing the surface) is to use a morphing method such as described above, and further illustrated in FIGS. 21A-21C. In this example, the surface is morphed to follow control points 2105. The closer a point is to a control point, the more it follows the control point; when a point is far from any control point, it's less morphed. To simulate palatal expansion, the control points selected may include the crown center and root center of all teeth and/or sample points in the midline/middle plane (see, e.g., FIG. 21C). FIGS. 22A and 22B illustrate a view of a digital model of a patient's oral cavity before (FIG. 22A) and after (FIG. 22B) simulated expansion, showing morphing of the palate 2201 after expansion in FIG. 22B (tipping left and right maxillary halves).

Palatal Expander Design

Once the final and intermediate stages for the palatal expansion has been determined, as described above, the palatal expanders may be designed using the digital models of the stages. In some variations, the palatal expanders may be fabricated directly (e.g., using a 3D printing, etc.). In some variations, the palatal expanders may be fabricated by creating models (e.g., casts) of each stage, from which the palatal expander may be fabricated by a molding or forming technique. For example, a mold of the palatal expander may be made by forming a mold using 3D printing, and then molding (e.g., injection molding, etc.) the palatal expander.

The palatal expanders described herein may be configured to generally include a pair of tooth engagement regions connected by a palatal region. The pair of tooth-engaging regions are typically on opposite sides of the jaw (e.g., left and right side). In some variations instead of two tooth engaging regions connected by the palatal region, a single tooth engaging region (e.g., spanning the right and left sides) may be used. The tooth engaging regions may include an occlusal side and a buccal side a lingual side that is continuous with (or forms part of) the palatal region.

In the design of the palatal expander, it may be particularly beneficial to control the thickness of the different regions of the palatal expander (thereby controlling the strength and/or forces applied by the appliance), as well as the ability to put on and remove the appliance. For example, the occlusal side of the tooth engagement regions may be thinner than the palatal region, and the buccal side may be thinner than the occlusal side. Related to the thickness, the smoothness of the upper surface (e.g., the palatal surface, facing and/or worn against the palate) and the smoothness of the lower surface (e.g., the lingual surface, facing the tongue) may be determined and configured so that the device is both comfortable, safe and easy to wear, without disrupting the patient's speech.

Figure 30:
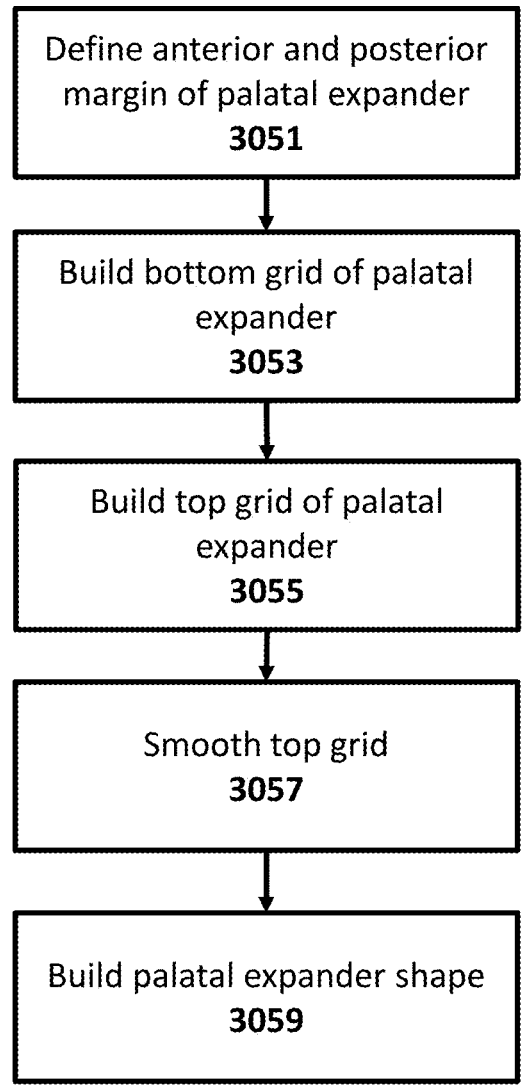
FIG. 30 illustrates one example of a method for designing a palatal expander (or a series of palatal expander) using the stages determined as described herein.
Figure 31A:
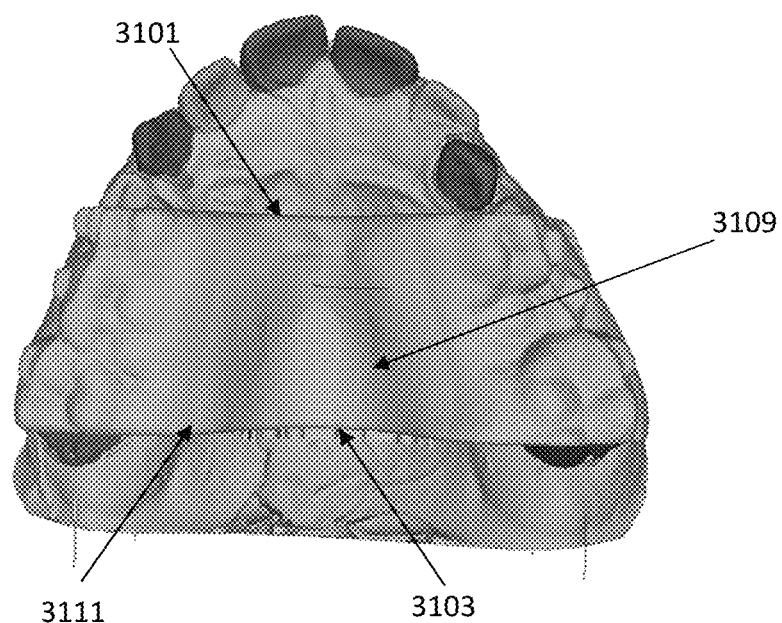
FIGS. 31A-31B illustrate an example of a palatal expander having defined anterior and posterior margins, showing top and posterior views, respectively.
Figure 31B:
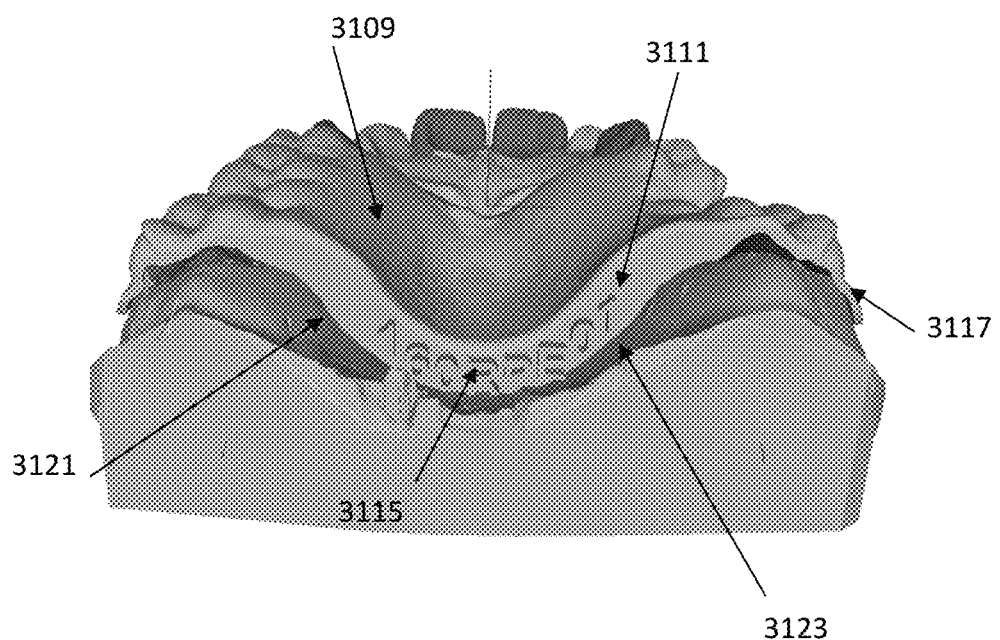

As mentioned above, any of the palatal expanders described herein may be generated using the apparatuses and methods described herein including by an apparatus (e.g., software, firmware, etc.) configured to automatically generate a digital model of the palatal expander, from which the actual palatal expander may be fabricated. For example, FIG. 30 schematically illustrates a method of designing the palatal expander using the stages determined as described above. In FIG. 30, for example, a method or apparatus for modeling a palatal expander based on the determined palatal expansion stage (from a series of stages) may initially include defining an anterior an poster margin for the palatal expander corresponding to that stage 3051. This is illustrated in FIGS. 31A and 31B, and described in more detail below. Once the anterior and posterior margins of the expander are defined, the apparatus or method may then determine the bottom grid for the palatal expander. The bottom grid may correspond to the palatal-facing surface of the expander, described above. This may include determining a clearance from the palatal region. Once the bottom grid is complete, the top grid (corresponding to the lingual-facing surface) may be determined 3055, and smoothed 3057, as described above. Finally the palatal expander shape maybe determined 3059, and finished. The process of FIG. 30 may be repeated for each of the stages, including the final stage. Once the digital model for each stage is complete, it may be fabricated, as described above, for example, by direct fabrication (e.g., 3D printing, etc.) or by indirect printing (e.g., molding, etc.).

Figure 32:
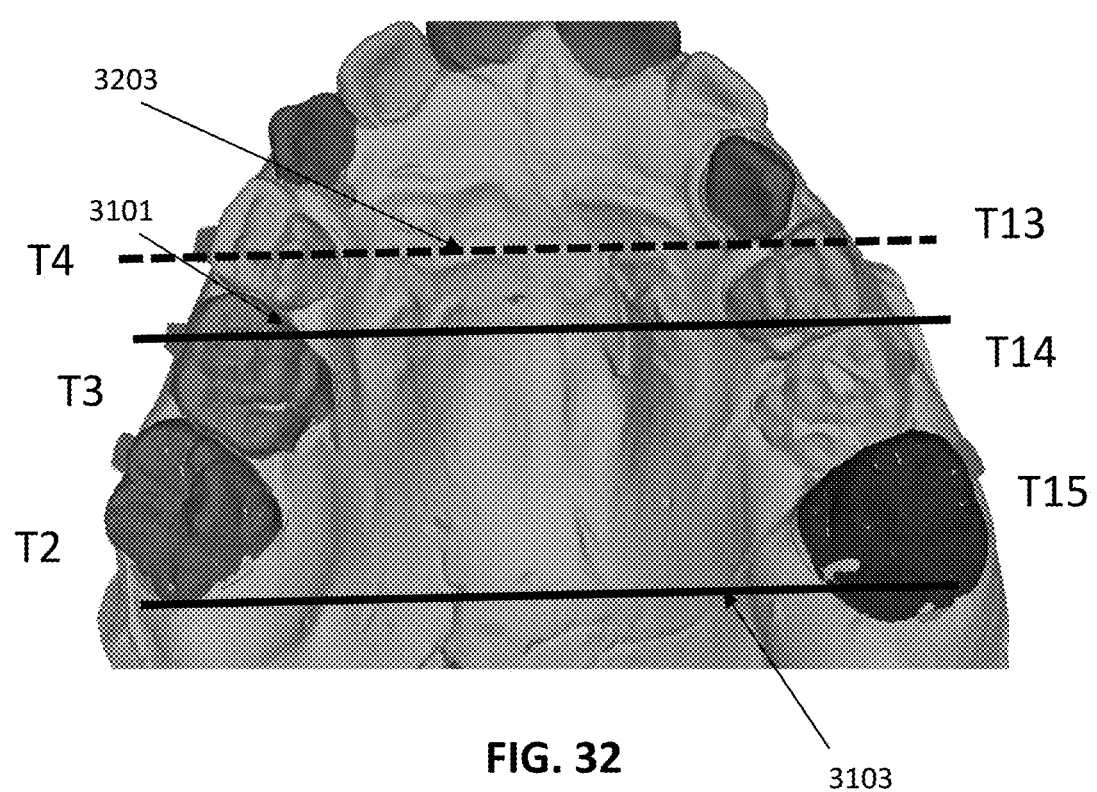
FIG. 32 shows an example of the anterior and posterior margin for some variations of palatal expanders as described herein.

FIGS. 31A and 31B illustrate the steps of defining the anterior and posterior margins of the palatal expander. In FIG. 31A, the anterior margin 3101 falls between the premolar and molar (T4 and T3 on the right side, between T13 and T14 on the left side). As shown in FIG. 32, in practice the anterior margin may cover as much as possible of the T3 (molar) and T14 (molar), and may cover at least some of the T4 and T13 (premolars). The posterior margin may cover as much as possible of the permanent molars T2 and T15, but not extend beyond them. The palatal expander may extend beyond. The dashed line 3203 between T4 and T13 may represent a maximum anterior extent of the palatal expander, either or both the palatal region or the tooth-enclosing region. The expander may include an offset (e.g., 2 mm) relative to these anterior and posterior margins, however the anterior margin may be limited so as not to extend beyond the maximum anterior line (covering T4, for example, but not the canines).

In FIG. 31A, the lingual-facing (top) surface 3109 may be smoothed, as described above and in additional detail below. Further, the edges of the margin may be rounded 3111. FIG. 31B shows a posterior view of the digital model of the expander appliance on the model of the teeth at a predetermined stage. In this example, the model show the thickened posterior region having a variable thickness (e.g., thicker in the palatal region, smoothly transitioning to a thinner occlusal region, then a buccal region, including a buccal extension 3117, that is thinner than the occlusal region). The palatal (bottom) surface 3121 includes a clearance 3123 from the palate, so that the majority of force applied by the apparatus to the maxilla is on the lateral regions (e.g., the teeth and/or in some variations, the lateral sides of the palate). This example also shows a tag or identifier 3115 on the posterior edge of the expander.

Figure 33:
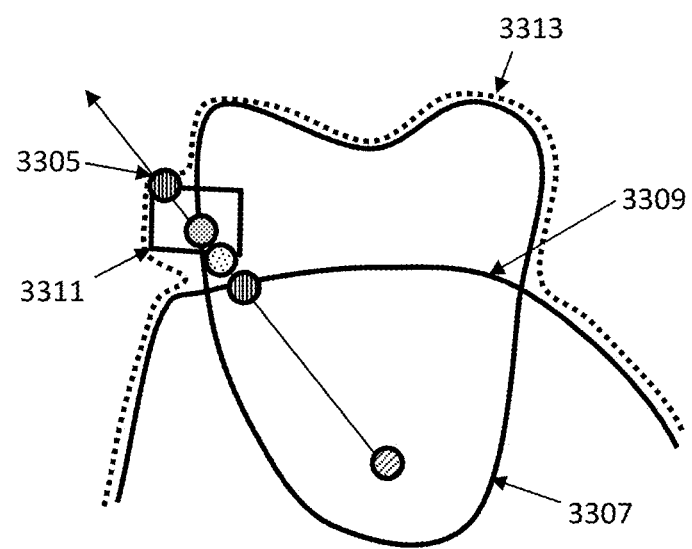
FIG. 33 illustrates a method of automatically determining a bottom surface of a palatal expander.

Once the lateral edges are determined, the bottom and top surfaces may be generated by creating a bottom grid and a top grid from the stage information. In general, this may be performed by scanning the palate, crowns and attachments (if included), adding clearance, and cutting and smoothing (e.g., the interproximal regions). Initially, the various segments (regions) of the arch may be defined, either automatically, manually or semi-automatically. For example, the central and crown regions may be identified and used to map from the 3D model to a 2D model. The center axis may be the middle and above the occlusal plane, and a crown scan axis may be near the crown center. The distance to the crown may be adjustable. Buccal and lingual side curves may also be identified, and used to segment the crown and palate. The bottom grid may then be built from the scanned teeth, palate and attachments. For example, a 3D vertex may be projected into 2D points. The shape of the palatal model, tooth crowns and attachment may be scanned and projected onto the bottom grid. To avoid overlap between the shapes (including between attachments and crowns), only the outermost of the vertex may be kept, uniting these component parts into a unified grid/surface. A minimum scan radius may be used to prevent the shape being too small. For example, FIG. 33 shows keeping only the outmost point 3305 on the attachment is kept, compared to other points when combining the crown shape 3307, palate shape 3309 and attachment shape 3311, resulting in a line 3313 for the palatal expander. The palatal expander may cover the central palate, crown, and may cover at least some of the buccal side of the patient's teeth and may extend further from the buccal line (the line between the teeth/crown and the gingiva), so that the palatal expander extends at least partially beyond tooth, over the gingiva. This buccal extension on the buccal side may make the palatal expander stronger and provide better attachment (e.g., engaging with attachment(s) on the teeth). The extension beyond the buccal side line (e.g., over the gingiva) may extend some extension angle (e.g., 1 mm) and the transition between the buccal side and over the gingiva may be smooth. The bottom surface of the expander (facing the gingiva/teeth) may be separated from the gingiva by a minimum distance (e.g., 0.05 mm, 0.1 mm, etc.). Thus, clearance (buccal clearance) may be added to prevent or minimize contact with the soft tissue on the jaw. The anterior/posterior convers of the grid (and therefore the edges of the palatal expander) may be rounded.

Figure 34A:
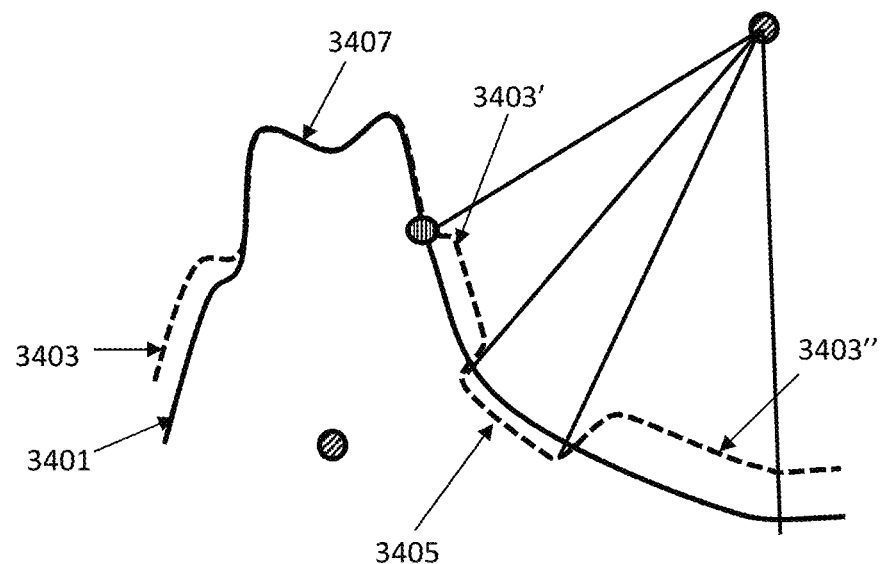
FIGS. 34A-34B illustrate examples of offsets (positive and negative) that may be included in any of the palatal expanders described herein.
Figure 34B:
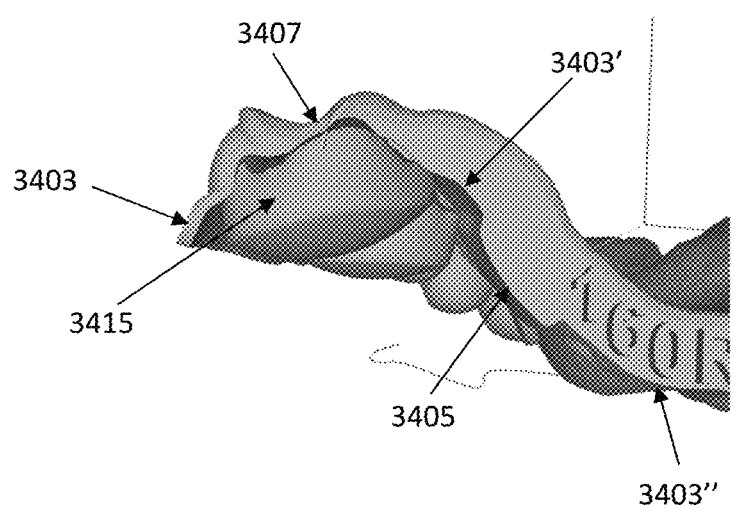

In general, clearance (both negative and positive) may be added or included in the bottom grid to provide either separation between the palatal expander or contact (and applied pressure) between the palatal expander and the teeth, palate or gingiva. For example, FIG. 34A illustrates an outline of the bottom grid 3401 and the modified to include positive clearance 3403, 3403', 3403" and/or negative clearance 3405. In FIG. 34A, the positive clearance on the buccal side 3403 provides buccal clearance that may prevent the palatal expander from touching the soft tissue on this side of the arch, and may also enhance removal of the apparatus; providing a ledge or lip that may be used to allow the finger (fingernail) or a tool to remove the expander more easily. On the lingual side, positive clearance adjacent to the crown region 3403' (palate crown clearance) may be included. The crown region 3407 of the palatal expander may contact the teeth (e.g., zero or very low clearance if a looser fit is desired). A negative clearance 3405 (palatal lingual clearance region) may be included so that the palatal expander contacts and pushes the side wall of the palate, e.g., for expanders that apply force to the tissue instead or in addition to the crown of the teeth. A palatal center clearance 3403" region may extend across the midline region of the palatal expander, and may also minimize or prevent irritation of the palate. The separation may be less than a maximum separation, particularly at the edge regions of the apparatus (e.g., 0.5 mm or less, 0.6 mm or less, 0.7 mm or less, 0.8 mm or less, 0.9 mm or less, 1 mm or less, 1.1 mm or less, 1.2 mm or less, 1.3 mm or less, etc.) which may prevent material such as food particles from getting trapped between the palatal expander and the palate. A minimum separation of this same region may be, e.g., 0.01 mm, 0.02 mm, 0.03 mm, 0.04 mm. 0.05 mm, 0.06 mm, 0.07 mm, 0.08 mm, 0.09 mm, 0.1 mm, 0.2 mm, 0.3 mm, 0.4 mm, etc. In FIG. 34B, the bottom grid 3401 maps to a palatal expander 3411 shown over the crowns 3415.

The methods and apparatuses may cut and smooth the region of the palatal expander that extends between the teeth (the interproximal region), so that this region is not too thin or fragile, and provide a smooth radiused edge.

Figure 35:
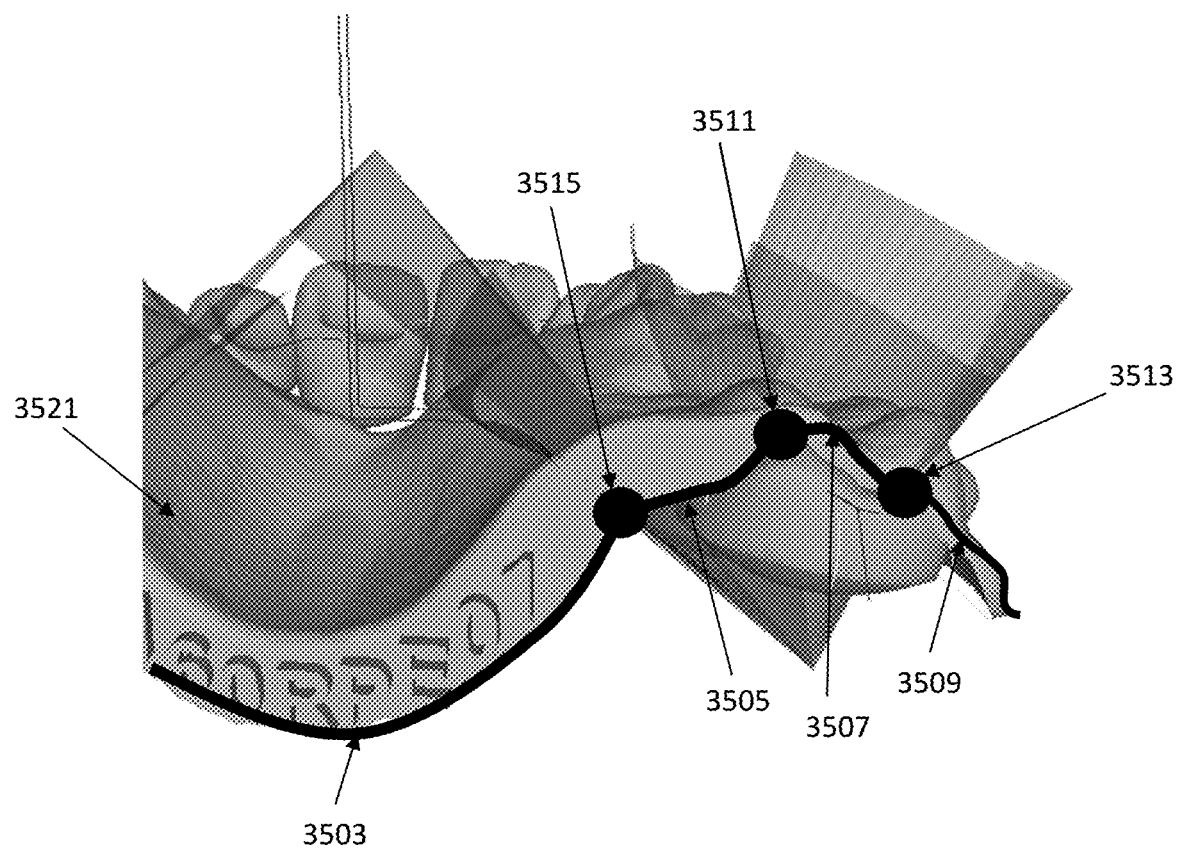
FIG. 35 illustrates the thicknesses of various sub-regions (e.g., palatal center region, lingual gingival region, occlusal side, and buccal side (including buccal extension).

The top (e.g., tongue-facing side) of the expander may then designed by building a top grid. The top may be formed so that the expander has different thicknesses in different areas, including in particular the palatal, buccal and occlusal regions. These areas may be determined by determining buccal and lingual ridges, e.g., finding and connecting ridge points on the buccal side, then on the lingual side (and connecting the lingual ridge points by a smooth curve, and connecting buccal ridge points by a smooth curve). For example, the top grid may be a copied, but offset version of the bottom grid, e.g., assuming a thickness which is then adjusted. The thickness may be adjusted based on the region. As mentioned, the different regions may be defined automatically, manually or semi-automatically (manually adjusted/corrected from the automatic determination). FIG. 35 illustrates an example of the different regions and their thicknesses. In FIG. 35, the palatal center region 3503 may be set to a thickness (e.g., 2 mm or greater, 2.2 mm or greater, 2.4 mm or greater, 2.5 mm or greater, 2.6 mm or greater, 2.8 mm or greater, 3 mm or greater, 3.2 mm or greater, 3.4 mm or greater, 3.6 mm or greater. 3.8 mm or greater, 4 mm or greater, etc. including between 2.1 mm and 7 mm, between 3 mm and 6 mm, etc.). The thickness selected may depend in part on the material used, in order to provide sufficient rigidity and Young's modules to expand the palate in the desired time period at the desired rate (e.g., 0.25 mm per day, 0.5 mm per week, etc.). The lingual gingival region 3505 may be set, for example, so that the thickness smoothly transitions from the palatal center region thickness to the occlusal side 3507 thickness. The occlusal side thickness 3507 is typically less than the palatal central region thickness, and may be, for example, between about 1 mm and about 3 mm (e.g., about 1.5 mm) and may be set so that this region can withstand biting, chewing and food eating. The palatal center region 3503 may transition into the lingual gingival region 3505 at the lingual transition curve 3515; the lingual gingival region 3505 may transition to the occlusal region 3507 at the lingual ridge 3511; and the occlusal region 3507 may transition to the buccal side 3509 at the buccal ridge 3513. The thickness of the buccal side 3509 is typically less than the occlusal side 3507, and the buccal gingival side may have a thickness of between about 1 mm and 0.5 mm (e.g., about 0.75 mm), and may generally be sufficiently flexible to aid insertion and removal of the palatal expander 3521. As mentioned above, this buccal gingival region may be hinged, or may include slits, slots, cut-out regions to permit all or a portion to be pulled away from to help in insertion/removal.

In any of these apparatuses, the thickness of the palatal expander may be modified based on the anterior/posterior location. For example, when the palatal expander covers 3 or more teeth, the anterior section may appear bulky and may be more noticeably contacted by the patient's tongue, which may cause some discomfort or speech impairment. This may be addressed by gradually reducing the central palatal thickness 3503 from the posterior to anterior regions (e.g., the thickness in the anterior region may be less than the thickness in the poster region). For example, the anterior thickness may be between 30% and 95% of the posterior region thickness (e.g., between 35% and 95%, between 45% and 95%, between 55% and 95%, between 75% and 95%, etc.).

The thickness of the central palatal region 3503 may refer to an average or maximum thickness. The thickness of the central palatal region may include region of lesser or greater thickness in addition to (or instead of) the general anterior-to-posterior gradient mentioned. For example, the top surface of the palatal expander may be smoothed to remove protrusions or bumps. For example, after adjusting the thickness (e.g., the spacing between the top grid/top surface and the bottom grid/bottom surface) as described above, the top, tongue-facing side, may be smoothed by adjusting the local thicknesses to remove rapid changes in the topology due to sharp bends, grooves, ridges, etc. that may be on the bottom grid/bottom surface. Such rapid transitions may be weak points when the palatal expander is worn, and compressed. Smoothing may involve filling in such sharp bends, as shown in FIGS. 36A and 36B. For example a relatively sharp bend 3605 (in FIG. 36A) may be smoothed by filling in the center of these bend regions 3606, as shown in FIG. 36B.

FIG. 37 illustrates one method of smoothing the top of the palatal expander (e.g., the portion facing the patient's tongue when worn). For example, the top grid may be smoothed by fitting a smooth thin plate spline surface from the top central (palate) region of the top grid. In this example, the original surface 3701 includes a number of rapid changes (ridges/peaks, etc.). A smoothed surface 3703 may be formed from the original surface, the original and smoothed surface may be combined to form a final surface 3705 that fills in grooves, but does not cut into the thickness of the central palatal region of the expander; thus the thickness is not reduced and the resulting expander remains strong. For example, in FIG. 37, grooved regions 3713 are filled, while the peaks of the ridges 3715 may be kept.

Figure 38A:
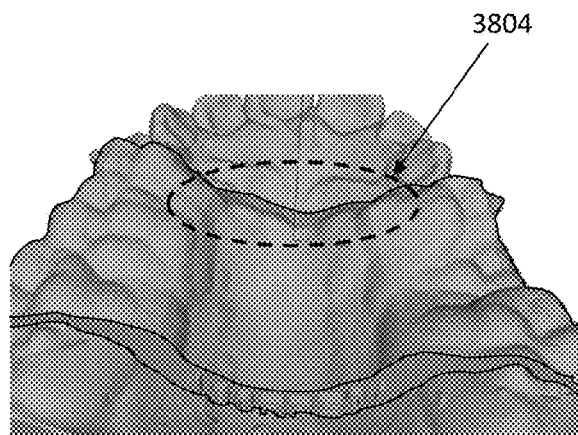
FIGS. 38A-38B illustrate smoothing of the anterior region (e.g., the anterior-most 0-20 mm) of one surface of a palatal expander.
Figure 38B:
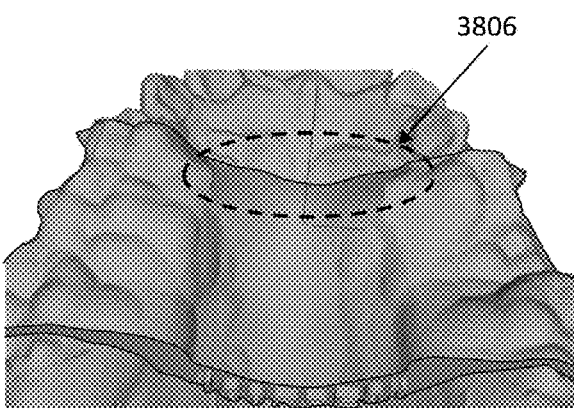

Additional smoothing may be applied in the anterior portion of the palatal expander in particular. For example, when the anterior thickness is recued significantly compared to the posterior thickness (e.g., from 4.5 mm posterior to 1.5 mm anterior) bumps may be created, even when using the general smoothing technique described above; these bumps may be irritating and may be further smoothed. This is illustrated in FIGS. 38A and 38B. In FIG. 38A, the anterior bumps 3804 may be smoothed 3806 by applying the technique described above (and illustrated in FIG. 37), e.g., interpolating and smoothing (for example using a thin plate spline) the surface, but lifting the restriction that prevents reducing the ridges (e.g., the "fill only" limitation illustrated in FIG. 37). Thus the anterior region (e.g. the region from 0-1.2 cm from the anterior margin) may be smoothed to allow reducing the ridges, thereby further thinning the central palatal region, while the region posterior of this to the posterior margin may be limited to filling only (expanding, but not reducing, the thickness) to provide a smooth surface.

Figure 39A:
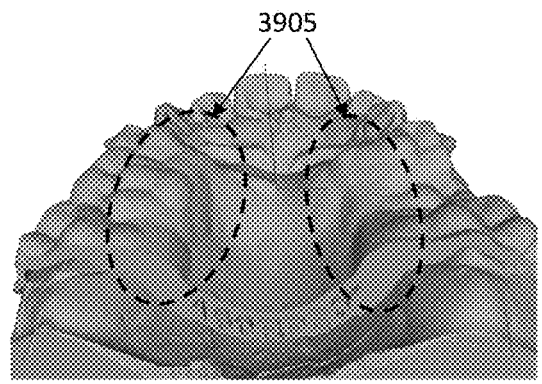
FIGS. 39A-39C illustrate another example of a method of smoothing lateral side portions of a palatal region of an expander.
Figure 39B:
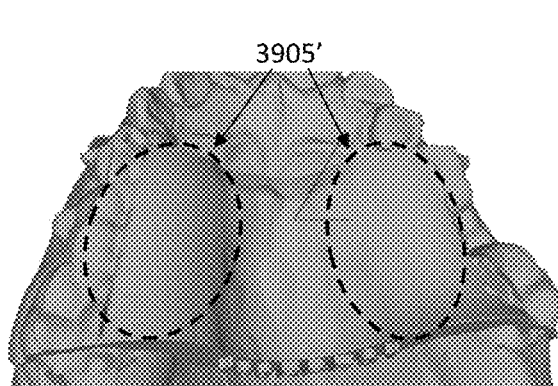
Figure 39C:
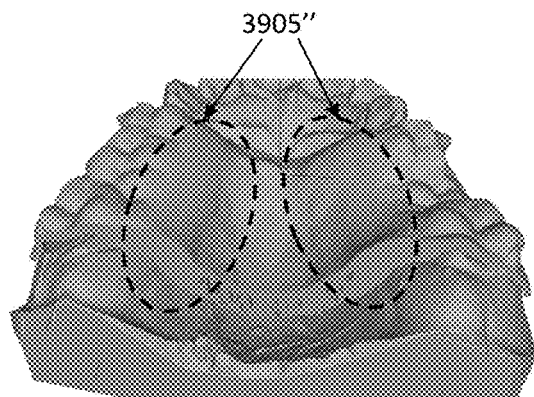

The lingual side portions of the rapid palatal expander may also be smoothed and otherwise modified to create additional space for the tongue, and remove rough edges, enhancing comfort. FIG. 39A shows an example of a lingual (top) side of a palatal expander that includes bumps/protrusions 3905 that may be uncomfortable for a patient. These lateral regions may be smoothed, for example, similarly to the top central palatal region smoothing described above. As illustrated in FIGS. 39B and 39C, the lateral regions 3905 may be smoothed by first fitting the top lingual sides to a smooth surface (e.g., by a thin plate spline or polynomial smoothing/interpolation) 3905', as shown in FIG. 39B. This over-smoothed region may then be blended 3905" with the original surface, as shown in FIG. 39C. For example, the original thickness may be used for regions that are closer to the crown and/or for regions that a closer to the anterior and/or posterior edges, while the smoothed surface may be used for other regions.

As mentioned above, the anterior and posterior edges may be smoothed/rounded (e.g., by having a rounding radius of between about 0.4 mm and about 1.2 mm, e.g., between 0.5 mm and 1 mm, etc.).

In general, for each stage of the palatal expansion, a palatal expander shape may be created as described, e.g., based on the tooth positions and palatal position determined. For example, bottom and top grids may be projected from 3D to 2D, and triangulated to get the mesh. Anterior and posterior edges may also be triangulated. The resulting palatal expander shapes for all of the stages may be used to form the sequence of expanders by direct or indirect fabrication.

Figure 23A:
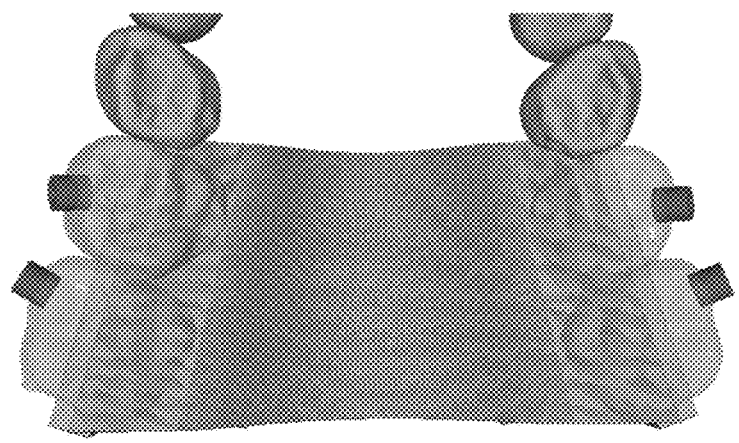
FIGS. 23A-23C illustrate an example of a fabrication technique for fabricating a palatal expander using any of the digital models described herein.
Figure 23B:
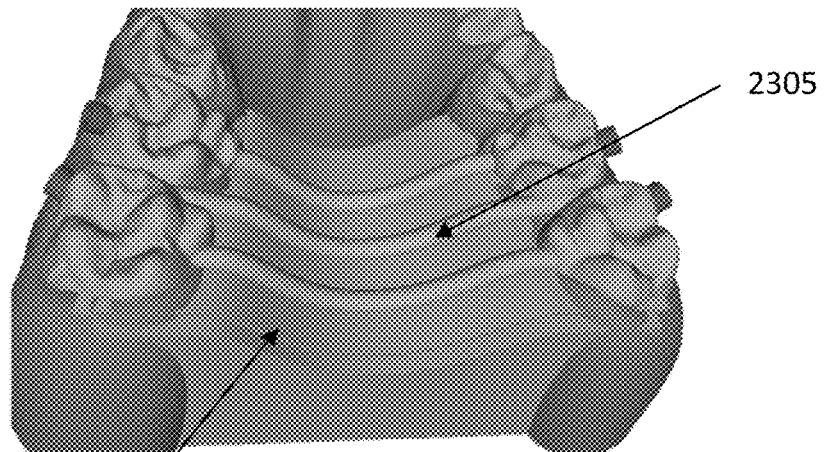
Figure 23C:
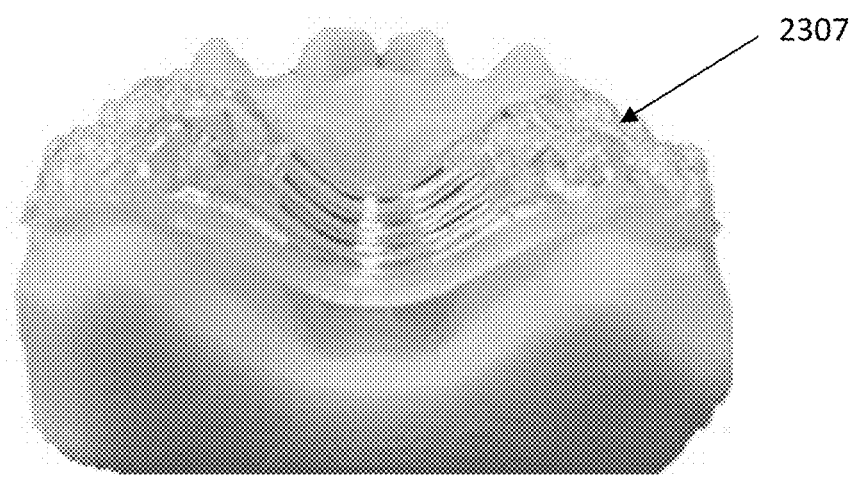

Thus, once the palatal expanders have been designed from the final and intermediate positions of the digital model ("staging" the treatment as described above), the series of palatal expanders may be formed by any desired procedure, including molding, lamination, and/or direct fabrication methods, described in more detail below. Thus, after the treatment is staged, the movement of palatal halves (left and right jaw) and dental movement of tooth is defined. The palate surface may be morphed according to the movement of teeth and midline suture, as discussed above. Retention attachments (such as the attachment connectors discussed above) may be added into each tooth, to hold the expander firmly on the crown. Typically, a palatal expander may be designed for each stage. For manufacture processes using thermoforming, like lamination, the fabrication may include: getting the tooth position of last two molars at each stage, creating a trans-palatal arch (TPA) portion, which links the left and right side of molars, adding ribs to strength the expander and/or walls to support the arch; creating a mold of all crown, gingiva and TPA (e.g., using SLA or other 3D print technology), thermoforming one or several layers of plastic shell on the mold, and/or cutting the expander from the mold. An example of this is shown in FIGS. 23A-23C, showing a trans-palatal arch portion 2303, ribs 2305 and walls and final expander 2307. The trans-palatal arch portion may be smooth (rather than including ribs, as described above), and the methods and apparatuses described herein may adjust the shape of the TPA portion. Adjustment points may be added. For example, the user may move adjustment points to change the shape of TPA. Alternatively or additionally, the user may adjust the shape to match the "morphed palatal surface" (or the shape may be automatically adjusted). As mentioned, the expander may be positioned close to the palate, but still with some clearance or space. FIGS. 24A-24C illustrate adjustment of a smooth TPA shape (also showing a morphed palatal surface), indicating the user-controlled or semi-automatic adjustment of the TPA shape by moving one or more points 2403, 2403'. The method or apparatus may automatically constrain the types of adjustments based on the constraints and considerations described above, including limiting the force applied, the rate of expansion, etc. The method and/or apparatus may automatically or semi-automatically adjust the thickness of the expander as the user or apparatus adjusts the morphology (e.g., increasing/decreasing the thickness, etc.).

In some variations the expander may touch all or the majority of the palate, or may have a predetermined clearance from the palate, as described above. In this case, the expander may be based on the morphed (e.g., offset) palatal surface. The apparatus and/or method may resample the surface and build a height map, add some clearance (for example 0.25 mm on the height map), build the TPA surface from the height map, and may add ribs and walls for better manufacture. FIGS. 25A and 25B illustrate one example of this method, showing the formation of an expander 2505 from an intermediate configuration of the digital model. In both FIGS. 24A-24C, 25A and 25B the models include the attachment connectors on the model of the teeth, which may be generally be included or added to the digital model.

Figure 26A:
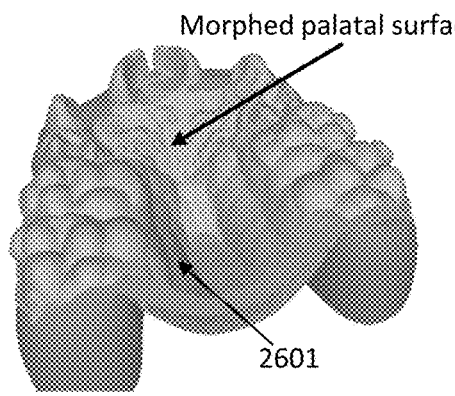
FIGS. 26A-26D illustrate another method of designing and fabricating an expander as described herein.
Figure 26B:
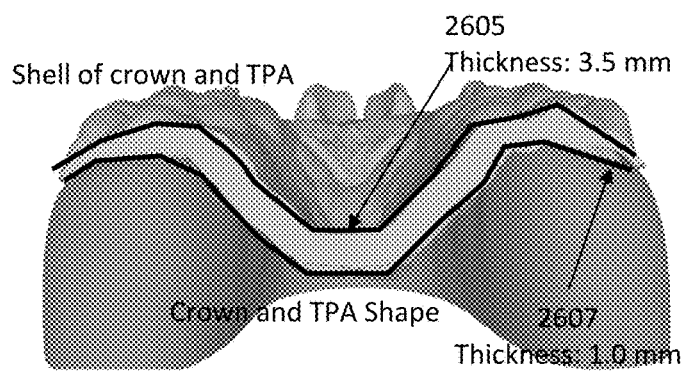
Figure 26C:
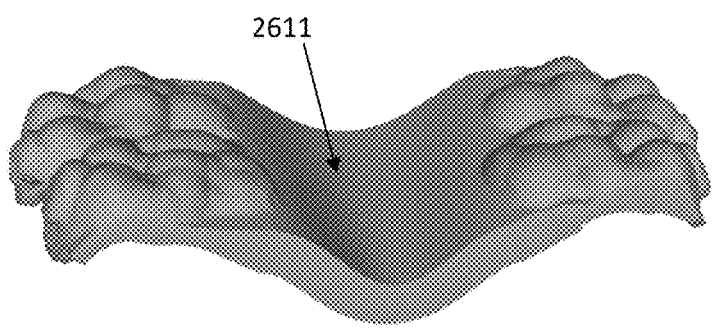
Figure 26D:
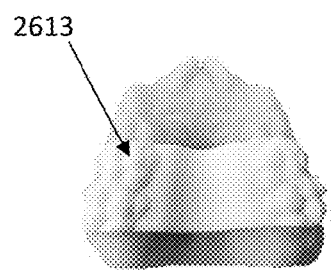
Figures 27A, 27B, 27C:
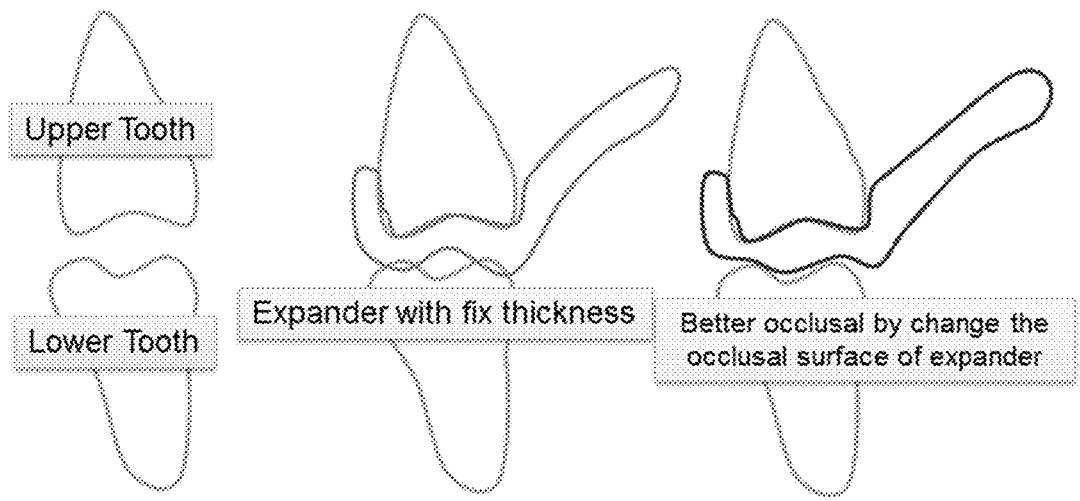
FIGS. 27A-27C describe one method of adjusting the occlusal of an expander.

FIGS. 26A-26D illustrate an example of fabrication of an expander 2601 of a set of expanders formed using the methods and apparatuses described herein. In this example, the expander may be fabricated by a direct fabrication (e.g., 3D printing) method, by: getting the crown shape of each molar, getting the shape of the TPA (e.g., smooth or based on palate surface) from the model, and forming a shell (tooth retainer region and palatal region) for the crown and TPA surfaces. The thickness of this shell may be different at different regions. For example, the thickness of the TPA region 2605 (e.g., center) may be about 3.5 mm, the thickness near the buccal side of crown 2607 may be only about 1.00 mm, as shown in FIG. 26B. FIGS. 26C and 26D show a design model of an expander (digital model of the expander) 2611, and a final fabricated version 2613, respectively. The shape of the expander can also be controlled or adjusted for better occlusal between upper and lower jaw, which may help patient bite and chew better, prevent grinding of expander, and speak normally. For example, the digital model of the patient's oral cavity may include the lower jaws (teeth) or this may be provided separately. Once the expander shape has been created (e.g., having the same thickness at occlusal surface or different thicknesses), the occlusion may be checked either automatically or semi-automatically, (e.g., checking the occlusion between the expander to lower teeth). The thickness of the expander over the occluded region may be reduced, where the expander collides with lower teeth, and may be increased if there is space. This is illustrated schematically in FIGS. 27A-27C, showing the adjustment of the occlusal surface of expander for better occlusal between upper and lower jaw. In FIG. 27A, upper and lower teeth (including the occlusal or intercuspation spacing between them) are shown. FIG. 27B shows the teeth of FIG. 27A with an expander having a fixed thickness between them, showing regions of overlap where the expander may non-uniformly separate the teeth. FIG. 27C shows an expander having adjusted occlusal thicknesses. Another design may provide a flat occlusal surface, so there is no "cusp to cusp" contact.

In general, a rapid palatal expander designer may be designed by the methods and apparatuses described herein based on biomechanics and biological knowledge, as discussed above. Clinically, the rapid arch expander may behave quite differently from normal orthodontic treatments. Expanders may be mostly used for children (e.g., from age 8-12) and applied only on maxillary jaw (upper jaw). By using somewhat larger forces (e.g., between about 70 N to 160 N), compared to normal braces (which typically exert about 1-2 N), rapid expansion may be achieved over the course of days, opening the midline suture of the maxillary jaw. In typical expanders, expansion speeds may be about 0.5 mm per day, and treatment may last around 2-3 weeks, compared to the braces having a treatment time of 1-2 years. After expansion treatment, there may be about a 3 to 6 month of "retention" period; big gaps (e.g., a 1-2 mm diastema) between upper central incisors may be created.

To achieve better outcomes, faster treatment, greater safety and comfort, the rapid palatal expanders described herein may be designed based on biomechanical and clinical knowledge, including modeling based the expansion angle, or other biomechanical constraints including those discussed above. Further, the forces and stiffness of the expander may be adjusted during the design process (including automatic or semi-automatic adjustments). For example, by digitally modeling and designing the expanders as described herein, there are many ways to adjust the force, or stiffness of the devices, including increasing the thickness or width of the TPA, using different or compound materials, such as metal, carbon fiber, Kevlar fiber, etc., changing the shape of TPA, adding ribs on the shape, etc. The methods and apparatuses described herein may allow one or more of these techniques (or others) to be modeled and selected automatically or by a user, and may allow adjustment for other parameters to keep the stiffness and/or force and/or rate of movement constraints on the devices within predetermined or settable parameter ranges.

For example, one way to adjust the force, but not the stiffness, of an expander is by adding more expansion distance on the expander. For example, a planned expansion distance at one stage 0.25 mm and the device may create only 30 N force; if this is not sufficient to open the suture at initial treatment (which may be set to between 60-160 N), the expander can be designed and fabricated based on a 0.5 mm expansion, which will create 60 N force and enough to open the suture.

Figures 28A, 28B:
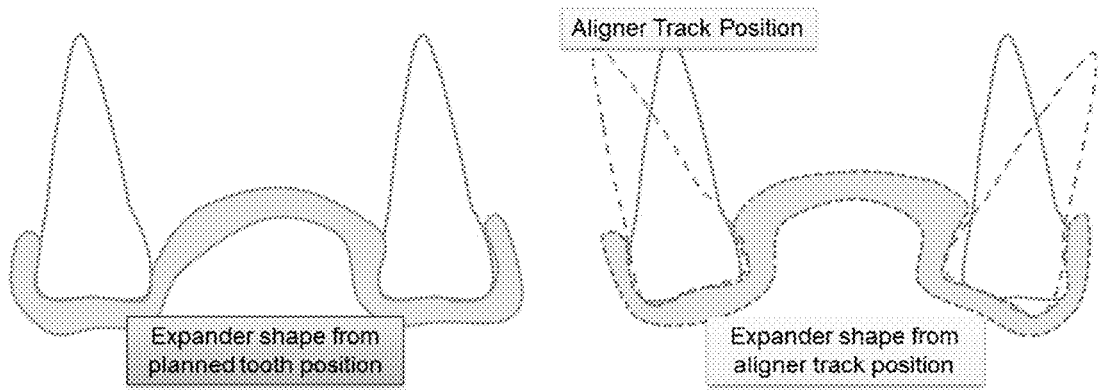
FIGS. 28A and 28B illustrates a first method of providing anti-tipping torque to an expander as described herein.

After rapid expansion, not only is the midline suture is opened, but the left and right maxillary bones may also be tipped buccally, so that the teeth may not be straight (also called buccally inclined). To control the crown tipping, the expander can be designed to add some "anti-tipping" torque one the tooth, by using align track activation or active attachments. For example, to use aligner track to add torque, at each stage, the apparatus or method may get the planned tooth position, and may adjust the tooth position by rotate the root buccally, which is called the aligner track position. This aligner track tooth position may then be used to create the expander, as illustrated in FIGS. 28A and 28B.

Figures 29A, 29B:
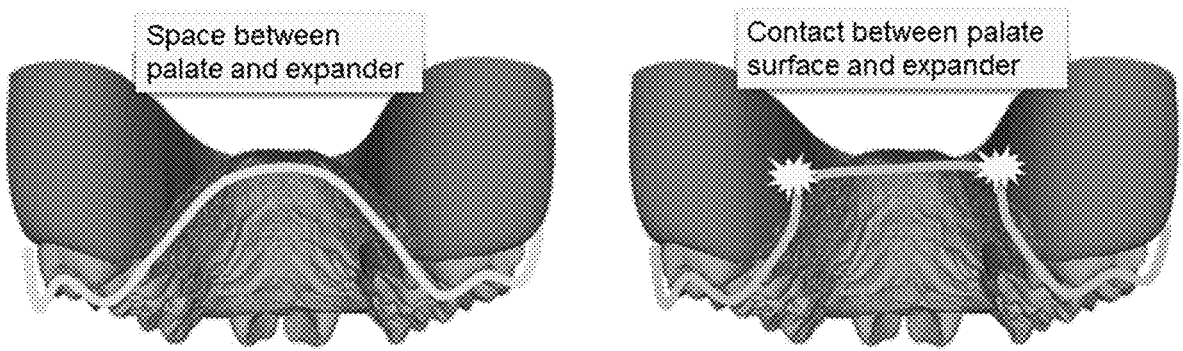
FIGS. 29A and 29B shows another example of a method of providing anti-tipping torque to an expander.

Another way to add more "anti-tipping" torque is by design the shape of expander, so that it contacts with the palate surface and can push the palate near the midline suture, as shown in FIGS. 29A and 29B. In this example, the space between the palate and expander is adjusted to apply force at a lateral contact point on the lingual side of the palate.

In any of these methods and apparatuses, the force applied by the expander may be controlled or adjusted based on the treatment stage. For example, the force created from the expander can be controlled and/or adjusted by the treatment stage. At the beginning of treatment, a large force may be needed to open the suture. To achieve a bigger force, the expander can be designed with higher stiffness. For example, by increasing the thickness of the central part of expander (TPA). At the middle of treatment, the force can be reduced, but the expansion velocity can be increased. For example, the thickness of TPA can be reduced to 50%, and the speed can be improved to, e.g., 0.50 mm/day. This may enhance the comfort and ease of insertion/removal, and may provide additional room for the patient's tongue. Closer to the end of the treatment, the expander may be stiffer and the velocity reduced, which may help stabilize the expansion. Thus, in general, the series of expanders may be configured so that the expanders to be worn later in treatment are stiffer (particularly the palatal region) and provide less force between the teeth compared to earlier expanders.

In addition, the patient's age may influence the design parameters for the expanders. When the patient is young (e.g., <7 years) old, the force needed to open suture and expansion may be smaller. So the stiffness of expander can also be reduced. For adult patients (who may also use surgical techniques to open suture in addition to the expanders described herein), the expansion force may be much bigger than for younger patients. The expander may also be stiffer.

The force and stiffness of the expander may be based at least in part on the arch shape and/or size. When the arch is narrow and deep, the expander using the palate shape may also be narrow and deep. Thus, the expander may be less stiff. In this case, the clearance between the expander and the palate may be increased, making the shape flat and stiffer. Additionally or alternatively, the thickness of TPA region may be increased to increase stiffness. When the patient's arch is wide, the stiffness of the expander may be small, and thus the thickness of TPA region may be increased.

In general, the digital models design method and apparatuses of using them described herein may allow additional clinical information to be used to improve the treatment and safety of the expanders. For example CT scans may be used to check the bone density and maturity of midline suture, and/or the forces needed to open suture, which may be used for these designs. For example, when a midline suture is not matured, the force and stiffness can be reduced. For an adult patient, implant tooth, crown and/or bridge teeth can be marked, and the expander may be designed to avoid those teeth.

Once a series of palatal expanders is designed, including digitally (or in some variations, manually), the individual devices forming the series may be fabricated. Described herein are a variety of fabrication methods that may be used. Any of these fabrication methods may be combined or modified in view of the other fabrication methods or parts of these fabrication methods. Different expanders in a patient series may be fabricated by the same method or by different methods.

Fabrication Methods

Once the series of palatal expanders has been planned, as described above, they may be fabricated; fabrication may be performed all at once or in batches (e.g., provided as a complete or partial set, such as days 1-4) or separately, and provided to the patient. Each expander may be marked to separately identify it, including marking to indicate a preferred order (e.g., first, second, etc.).

The palatal expanders described herein may be fabricated directly, for example by digitally designing the expander and fabricating the digital model using a 3D printer or other direct fabrication technique. Alternatively or additionally, the palatal expanders described herein may be fabricated indirectly, for example, using a physical model of the patient's dentation (e.g., a ceramic, plastic, plaster, etc. model), onto which materials are applied to form the palatal expander. Indirect fabrication methods may include lamination, in which the palatal expander is formed from laminated layers or portions. Indirect fabrication methods may also include direct fabrication of the model using a direct fabrication technique (e.g., 3D printing, etc.). Hybrid fabrication methods, in which a portion of the expander is directly fabricated, and then combined with additional elements (including layers or supports), with or without the use of a model of the patient's dentition, may also be used.

In any of the indirect fabrication techniques described herein, the expander may be formed on a physical model that has been adjusted (e.g., by moving palate) to a desired position on the way to the final expanded position. The physical model may include attachments (buttons, etc.) for coupling to attachments (e.g., trough-holes, etc.) on the expander, as discussed above.

When a physical model is used (either manually generated from impressions of a patient's teeth or from one or more digital models), the expander may be fabricated by molding a sheet of material over the model. In general any appropriate material may be used for the expander, as long as it is sufficiently biocompatible and possesses the rigidity and physical characteristics necessary (either on its own or in combination with other materials). For example, an expander may be formed of an acrylic material that is applied in a sheet over a physical model, formed (e.g., thermoformed, set) and then cut and/or trimmed. In various examples provided herein, the material may form (including set) by temperature and/or light or other appropriate means. For example, an expander may be formed of a thermoplastic curable polymer.

As discussed above, direct fabrication may be used to make any of the expanders described directly, using as input a digitally designed expander (e.g., a digital file specifying the geometry. Thus, these apparatuses may be formed without the need for a physical model of the patient's teeth/gingiva/palate. Direct fabrication may include 3D printing or additive manufacturing (e.g., extrusion type, light polymerization type, powder bed type, lamination type, powder fed type, etc.).

Any of the expanders described herein may be formed by one or more lamination processes in which multiple layers are sequentially or simultaneously attached together to form the expander. A lamination method may generally include using thermoplastic layers of various thicknesses and combining them to form various layers.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature. Thus, adjacent may include against (e.g., next too) or contacting, including pressed against.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A series of palatal expanders comprising a plurality of palatal expanders configured to be sequentially worn by a patient to expand the patient's palate, the series of palatal expanders comprising, for each of a first and second palatal expander in the series:
   a left tooth engagement region configured to be removably worn over the patient's teeth in a left upper jaw region, the left tooth engagement region having a left occlusal region comprising a polymer shell, the polymer shell in the left occlusal region having a first inner occlusal surface and a first outer occlusal surface and a thickness therebetween;
   a right tooth engagement region configured to be removably worn over the patient's teeth in a right upper jaw region, the right tooth engagement region having a right occlusal region comprising the polymer shell, the polymer shell in the right occlusal region having a second inner occlusal surface and a second outer occlusal surface and a thickness therebetween; and
   a palatal region between the left tooth engagement region and the right tooth engagement region,
   wherein the first and second inner occlusal surfaces are shaped to conform to a geometry of corresponding teeth surfaces of the patient's upper jaw,
   wherein the first and second outer occlusal surfaces of each of the first and second palatal expanders are shaped to conform to a geometry of corresponding teeth surfaces of the patient's lower jaw as the respective palatal expander is worn, so as to provide occlusion between the first and second outer occlusal surfaces and the corresponding teeth surfaces,
   wherein the left and right tooth engagement regions of each of the first and second palatal expanders are configured to be worn on the teeth in the patient's upper jaw region and wherein the thicknesses between the inner and outer occlusal surfaces vary in the corresponding left and right occlusal regions to cause cusps of corresponding teeth of the lower jaw to be laterally offset from cusps formed by the first and second outer occlusal surfaces when the first and second outer occlusal surfaces of the respective palatal expander are engaged with the corresponding teeth of the lower jaw, and
   wherein the second palatal expander in the series of palatal expanders is configured to further increase separation between the left tooth engagement region and the right tooth engagement region relative to the first palatal expander.

2. The series of palatal expanders of claim 1, wherein for at least one of the first and second palatal expanders, a first portion of the left occlusal region has a greater thickness with respect to a second portion of the left occlusal region, wherein the first portion with the greater thickness is laterally offset from cusps of corresponding teeth of the lower jaw.

3. The series of palatal expanders of claim 1, wherein for at least one of the first and second palatal expanders, in a first portion, a thickness between the first outer occlusal surface and the first inner occlusal surface is less than a thickness of an adjacent second portion, wherein the first portion is positioned to interface a cusp of the corresponding teeth of the lower jaw.

4. The series of palatal expanders of claim 1, wherein for at least one of the first and second palatal expanders, the palatal region has an average thickness that is different than average thicknesses of the left and right occlusal regions, and average thicknesses of buccal region of the left and right tooth engagement regions are different than average thicknesses of the left and right occlusal regions.

5. The series of palatal expanders of claim 1, wherein for at least one of the first and second palatal expanders, a top surface of the palatal region is offset from a bottom surface of the palatal region by a thickness such that an average thickness of the palatal region is greater than an average thickness of an occlusal region of the left and right tooth engagement regions, and an average thickness of a buccal region of the left and right tooth engagement regions is less than the average thickness of the occlusal region.

6. The series of palatal expanders of claim 1, wherein for at least one of the first and second palatal expanders, a tilt angle between the left tooth engagement region and the right tooth engagement region increases relative to subsequent palatal expanders in the series of palatal expanders, wherein the tilt angle is an angle relative to a plane through a midpoint of the patient's upper jaw in an initial position of the patient's teeth in the upper jaw region when a first palatal expander of the series of palatal expanders is worn by the patient.

7. The series of palatal expanders of claim 1, further wherein, for at least one of the first and second palatal expanders, the palatal region comprises a lingual surface that is configured to face the patient's tongue when the palatal expander is worn is smoother than a palatal surface that is configured to face the patient's palate when the palatal expander is worn.

8. The series of palatal expanders of claim 1, wherein for at least one of the first and second palatal expanders, the left tooth engagement region comprises a left buccal extension region configured to extend at least partially over the patient's gingiva when the palatal expander is worn by the patient.

9. The series of palatal expanders of claim 1, wherein the left tooth engagement region and the right tooth engagement region are progressively rotated in the series of palatal expanders about an expansion axis in a mid-plane relative to the patient's face extending between the patient's nose and a back of the patient's upper jaw.

10. The series of palatal expanders of claim 1, wherein at least one of the first and second palatal expanders of the series of palatal expanders is configured to add torque to rotate a root of at least one tooth buccally to control tipping of a crown of the at least one tooth during palatal expansion.

11. A method of designing a series of palatal expanders comprising a plurality of palatal expanders configured to be sequentially worn by a patient to expand the patient's palate, the method comprising:
receiving a digital model of a patient's oral cavity in an initial position;
adjusting the digital model from the initial position to a final position in which a palate is expanded by morphing the digital model to reflect an orthopedic expansion of the patient's midline suture;
generating a palatal expander model corresponding to each intermediate position of a plurality of intermediate positions of the digital model between the initial position and the final position,
each palatal expander model including a left tooth engagement region having a left occlusal region comprising a polymer shell, the polymer shell in the left occlusal region with a first inner occlusal surface and a first outer occlusal surface and a thickness therebetween, and a right tooth engagement region having a right occlusal region comprising the polymer shell, the polymer shell in the right occlusal region with a second inner occlusal surface and a second outer occlusal surface and a thickness therebetween, and a palatal region between the left tooth engagement region and the right tooth engagement region;
adjusting the thickness of the left occlusal region and the right occlusal region of one or more of the palatal expander models so that the thickness of the left and right occlusal regions are non-uniform and are adjusted to provide an occlusion between the first and second outer occlusal surfaces and corresponding teeth of the patient's lower jaw and so that cusps of the corresponding teeth of the lower jaw are laterally offset from cusps formed by the first and second outer occlusal surfaces when the first and second outer occlusal surfaces are engaged with the corresponding teeth of the patient's lower jaw,
wherein the first and second inner occlusal surfaces are shaped to conform to a geometry of corresponding teeth surfaces of the patient's upper jaw as the palatal expander corresponding to the one or more palatal expander models is worn;
outputting the palatal expander model corresponding to each intermediate position of the plurality of intermediate positions; and
fabricating a series of palatal expanders from the palatal expander model corresponding to each intermediate position of the plurality of intermediate positions.

12. The method of claim 11, wherein adjusting the thicknesses of the left and right occlusal regions comprises forming peaks on the first outer occlusal surface of the left tooth engagement region and the second outer occlusal surface of the right tooth engagement region, wherein the peaks are configured to be laterally offset from peaks of the teeth in the patient's upper jaw when the palatal expander corresponding to the one or more palatal expander models is worn.

13. The method of claim 11, wherein adjusting the thicknesses of the left and right occlusal regions comprises increasing the thickness of a first portion of the occlusal regions of the left and right tooth engagement regions relative to a second portion of the occlusal regions of the left and right tooth engagement regions, wherein the first portion with the greater thickness is laterally offset from cusps of corresponding teeth of the lower jaw, when the palatal expander corresponding to the one or more palatal expander models is worn.

14. The method of claim 11, wherein adjusting the thicknesses of the left and right occlusal regions comprises decreasing the thickness of a first portion of the occlusal regions of the left and right tooth engagement regions relative to a second portion of the occlusal regions of the left and right tooth engagement regions, wherein the first portion is positioned to interface a cusp of the corresponding teeth of the lower jaw when the palatal expander corresponding to the one or more palatal expander models is worn.

15. The method of claim 11, wherein adjusting the thicknesses of the left and right occlusal regions comprises adjusting the thickness of the occlusal regions of the left and right tooth engagement regions to conform to a shape of a tooth surface of a corresponding tooth of the patient's lower jaw when the palatal expander corresponding to the one or more palatal expander models is worn.

* * * * *